United States Patent [19]
Chandler et al.

[11] Patent Number: 5,870,697
[45] Date of Patent: Feb. 9, 1999

[54] CALCULATION OF RADIATION THERAPY DOSE USING ALL PARTICLE MONTE CARLO TRANSPORT

[75] Inventors: William P. Chandler, Tracy; Christine L. Hartmann-Siantar, San Ramon; James A. Rathkopf, Livermore, all of Calif.

[73] Assignee: The Regents of the University of California, Oakland, Calif.

[21] Appl. No.: 610,917

[22] Filed: Mar. 5, 1996

[51] Int. Cl.[6] .................................................. A61N 5/10
[52] U.S. Cl. ........................ 702/179; 378/62; 378/65; 378/97; 378/901; 600/1; 600/410; 600/425
[58] Field of Search .............................. 364/527, 413.13, 364/413.14, 413.19, 413.15, 413.16; 378/65, 97, 901, 62, 92, 153, 159, 207, 8; 128/898; 705/3; 600/425, 410, 509, 1, 407; 395/185.01, 183.13; 250/263, 475.2, 505.1, 580; 702/179

[56] References Cited

U.S. PATENT DOCUMENTS

| | | | |
|---|---|---|---|
| 3,987,281 | 10/1976 | Hodes | 235/151.3 |
| 5,291,404 | 3/1994 | Kurokawa et al. | 364/413.26 |
| 5,297,037 | 3/1994 | Ifuku | 364/413.15 |
| 5,341,292 | 8/1994 | Zamenhof | 364/413.13 |
| 5,418,715 | 5/1995 | Deasy | 364/413.26 |
| 5,418,827 | 5/1995 | Deasy et al. | 378/65 |
| 5,430,308 | 7/1995 | Feichtner et al. | 250/580 |
| 5,513,238 | 4/1996 | Leber et al. | 378/65 |

Primary Examiner—Eric W. Stamber
Attorney, Agent, or Firm—John P. Wooldridge

[57] ABSTRACT

The actual radiation dose absorbed in the body is calculated using three-dimensional Monte Carlo transport. Neutrons, protons, deuterons, tritons, helium-3, alpha particles, photons, electrons, and positrons are transported in a completely coupled manner, using this Monte Carlo All-Particle Method (MCAPM). The major elements of the invention include: computer hardware, user description of the patient, description of the radiation source, physical databases, Monte Carlo transport, and output of dose distributions. This facilitated the estimation of dose distributions on a Cartesian grid for neutrons, photons, electrons, positrons, and heavy charged-particles incident on any biological target, with resolutions ranging from microns to centimeters. Calculations can be extended to estimate dose distributions on general-geometry (non-Cartesian) grids for biological and/or non-biological media.

6 Claims, 48 Drawing Sheets

| PEREGRINE EXECUTIVE (PGXEC) 16 | | | |
|---|---|---|---|
| SUBROUTINE | PROCESS | INPUT | OUTPUT |
| GENERATOR GENXEC 20 | CONSTRUCTS PATIENT-DEPENDENT INFORMATION NECESSARY FOR THE MONTE CARLO TRANSPORT CALCULATION | • CT SCAN DATA ARRAY<br>• NUCLEAR/ATOMIC/ ELECTRON DATA<br>• RADIATION SOURCE SPECIFICATION<br>• USER OPTIONS | • MATERIAL SPECIFICATION ARRAY (MUSCLE, BONE, FAT, ETC.)<br>• MATERIAL DATA (COMPOSITION, DENSITY, ETC.)<br>• PARTICLE DATA (MASS, CHARGE, ETC.)<br>• NUCLEAR AND ATOMIC TRANSPORT DATA ARRAYS<br>• RADIATION SOURCE ANGULAR AND ENERGY DISTRIBUTIONS<br>• ARRAYS DESCRIBING BEAM DELIVERY COMPONENTS |

FIG. 3A

ALL-PARTICLE TRACKER (MCXEC) 22

| SUBROUTINE | PROCESS | INPUT | OUTPUT |
|---|---|---|---|
| BEAMSEL 262 | SELECTS PARTICLE ATTRIBUTES FOR A PRIMARY PARTICLE ARISING FROM AN EXTERNAL RADIATION BEAM | • RADIATION SOURCE ANGULAR AND ENERGY DISTRIBUTIONS<br>• ARRAYS DESCRIBING BEAM DELIVERY COMPONENTS<br>• MATERIAL DATA (INTERNAL) MATERIAL LISTS, ISOTOPE DATA, ETC.)<br>• NUCLEAR AND ATOMIC TRANSPORT DATA ARRAYS<br>• NUMBER AND ENERGY GROUP STRUCTURE FOR EACH PARTICLE TYPE | • ATTRIBUTES OF ONE PARTICLE (ENERGY, LOCATION, DIRECTION, TYPE) |
| BRACHYSEL 264 | SELECTS PARTICLE ATTRIBUTES FOR A PRIMARY PARTICLE ARISING FROM AN INTERNAL (BRACHYTHERAPY) RADIATION SOURCE | • SECONDARY PARTICLE ARRAYS | • ATTRIBUTES OF ONE PARTICLE (ENERGY, LOCATION, DIRECTION, TYPE) |

FIG. 16A

PHOTRAN 270
- TRACKS PHOTON TROUGH TRANSPORT MESH (PATIENT)
- RECORDS ENERGY DEPOSITED BY NEUTRON
- STORES ATTRIBUTES OF SECONDARY PARTICLES PRODUCED IN SECONDARY PARTICLE ARRAYS

- NUCLEAR TRANSPORT DATA ARRAYS
- NUMBER AND ENERGY GROUP STRUCTURE FOR NEUTRONS
- ATTRIBUTES OF ONE PARTICLE (ENERGY, LOCATION, DIRECTION, TYPE)
- SWITCHES FOR CODE CONTROL
- MATERIAL SPECIFICATION ARRAY (MUSCLE, BONE, FAT, ETC.) ASSIGNED TO EACH ZONE
- MATERIAL DATA (INTERNAL MATERIAL LISTS, ISOTOPE DATA ETC.)
- ATOMIC TRANSPORT DATA ARRAYS
- NUMBER AND ENERGY GROUP STRUCTURE FOR PHOTONS

- SECONDARY PARTICLE ARRAYS
- 3-D ENERGY DEPOSIT MAP (ARRAY)

FIG. 17B

ALL-PARTICLE TRACKER (MCXEC) 22

| SUBROUTINE | PROCESS | INPUT | OUTPUT |
|---|---|---|---|
| CPTRAN 272 | TRACKS HEAVY CHARGED PARTICLE THROUGH TRANSPORT MESH (PATIENT) RECORDS ENERGY DEPOSITED BY HEAVY CHARGED PARTICLE, STORES ATTRIBUTES OF SECONDARY PARTICLES PRODUCED IN SECONDARY PARTICLE ARRAYS | • SWITCHES FOR CODE CONTROL<br>• MATERIAL SPECIFICATION ARRAY (MUSCLE, BONE FAT, ETC. ASSIGNED TO EACH ZONE)<br>• MATERIAL DATA (INTERNAL MATERIAL LISTS, ISOTOPE DATA, ETC.)<br>• NUCLEAR TRANSPORT DATA ARRAYS<br>• HEAVY CHARGED PARTICLE TRANSPORT DATA ARRAYS<br>• NUMBER AND ENERGY GROUP STRUCTURE FOR HEAVY CHARGED PARTICLES | • SECONDARY PARTICLE ARRAYS<br>• 3-D ENERGY DEPOSIT MAP (ARRAY) |
| ELTRAN 274 | TRACKS AN PRIMARY ELECTRON THROUGH TRANSPORT MESH (PATIENT) RECORDS ENERGY DEPOSITED | • ATTRIBUTES OF ONE PARTICLE (ENERGY, LOCATION, DIRECTION, TYPE)<br>• SWITCHES FOR | • SECONDARY PARTICLE ARRAYS<br>• 3-D ENERGY DEPOSIT MAP (ARRAY) |

FIG. 18A

ELTRAN1 — 216

Tracks a secondary electron through transport mesh (patient) records energy deposited by electron, stores attributes of secondary particles produced in secondary particle arrays

- Code control
- Material specification array (muscle, bone, fat etc. assigned to each zone)
- Material data (internal material lists isotope data, etc.)
- Electron transport data arrays
- Number and energy group structure for electrons

- Attributes of one particle (energy, location, direction, type)
- Switches for code control
- Material specification array (muscle, bone fat, etc. assigned to each zone)
- Material data (internal material lists, isotope data, etc.)

- Secondary particle arrays
- 3-D energy deposite map (array)

FIG. 18B

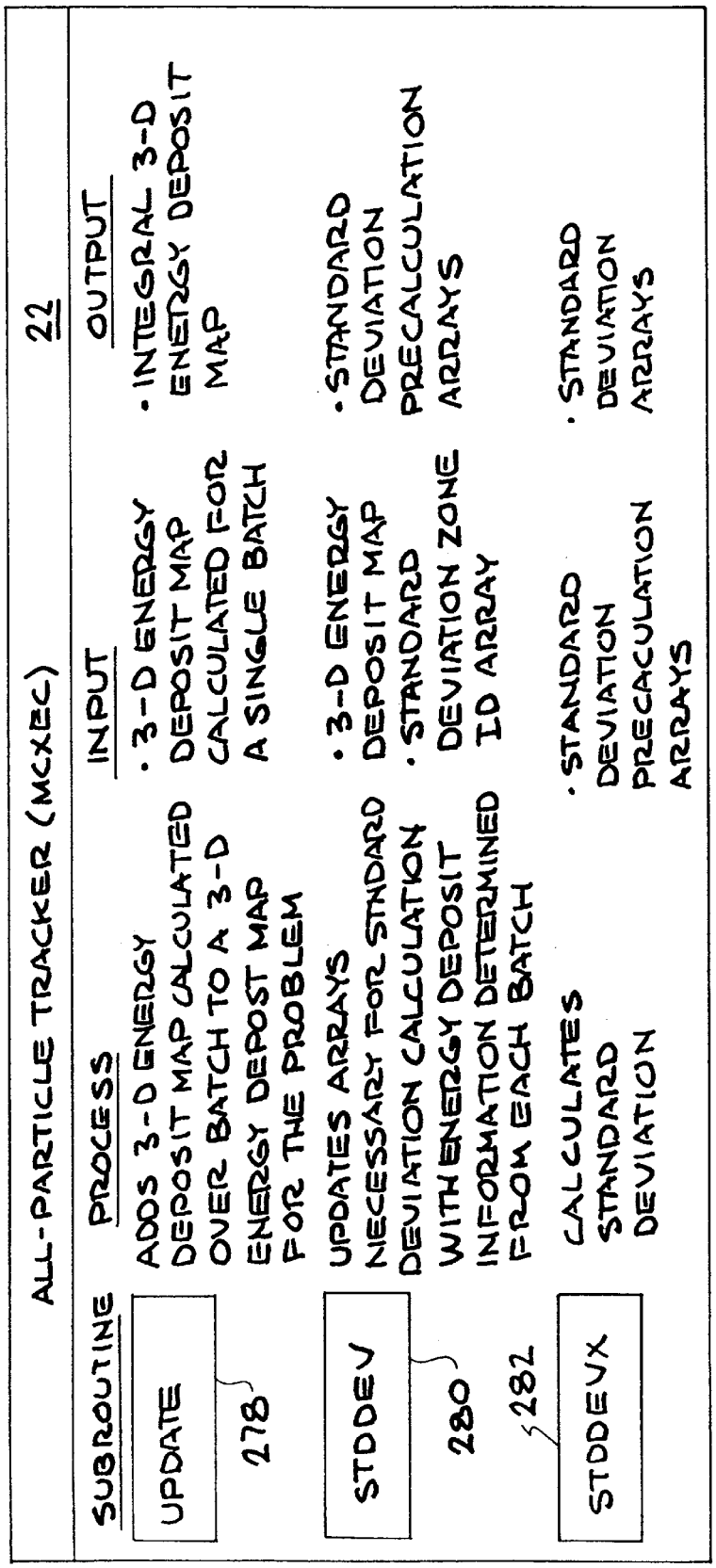

CALCULATION OF RADIATION THERAPY DOSE USING ALL PARTICLE MONTE CARLO TRANSPORT

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to the use of radiation therapy to treat cancer patients, and more specifically, it relates to a method for calculating the radiation dose.

2. Description of Related Art

Currently in the United States, radiation therapy is used to treat about 60% of all cancer patients. Since radiation therapy targets specific areas of the body, improvement in radiation treatment techniques has the potential to reduce both mortality and morbidity in a large number of patients.

The radiation source may be may be in the form of external beams of ionizing particles or radioactive sources internal to the patient. FIG. 1A shows a radiation beam 1 as it is delivered to the patient. External beams are usually produced by machines acting as particle accelerators. The beam delivery system consists of the radiation source 5 (see FIG. 1B), which is mounted on a gantry 2 which can rotate about a 360° arc around the patient. Each beam is shaped by a rotatable collimator 3. The patient lies on a rotatable table 4. The gantry 2 and table 4 both rotate about a single isocenter, as shown in FIG. 1.

External beam radiation therapy is performed with several types of ionizing radiation. Approximately 80% of patients are treated with photons, ranging in maximum energy from 250 keV to 25 MeV. The balance are treated primarily with electrons with energies from 4 to 25 MeV. In addition, there are several fast neutron and proton therapy facilities which have treated thousands of patients worldwide. Fast neutron therapy is performed with neutron energies up to 70 MeV, while proton therapy is performed with proton energies ranging from about 50 to 250 MeV. Boron neutron capture therapy is conducted with thermal and epithermal neutron sources. Most internal radioactive sources irradiate the patient with photons, although some sources emit low energy electrons.

The effects of ionizing radiation on the body are quantified as radiation dose. Absorbed radiation dose is defined as the ratio of energy deposited to unit mass of tissue. Because tumors and sensitive structures are often located in close proximity, accuracy in the calculation of dose distributions is critically important. The goal of radiation therapy is to deliver a lethal dose to the tumor while maintaining an acceptable dose level in surrounding sensitive structures. This goal is achieved by computer-aided planning of the radiation treatments to be delivered. The treatment planning process consists of characterizing the individual patient's anatomy (most often, this is done using a computed tomography (CT) scan), determining the shape, intensity, and positioning of radiation sources, and calculating the distribution of absorbed radiation dose in the patient. Most current methods used to calculate dose in the body are based on dose measurements made in a water box. Heterogeneities such as bone and airways are treated in an approximate way or ignored altogether. Next to direct measurements, Monte Carlo transport is the most accurate method of determining dose distributions in heterogeneous media. In a Monte Carlo transport method, a computer is used to simulate the passage of particles through an object of interest.

SUMMARY OF THE INVENTION

It is an object of the present invention to calculate the radiation dose in the body using three-dimensional Monte Carlo transport.

In the early 1990's, computer workstation technology improved such that the size and cost of computers required for Monte Carlo transport applications made them feasible for widespread use. This technology coupled with LLNL advancements in Monte Carlo transport methods provide a unique opportunity to apply advanced computer modeling technology to Radiation Oncology. The present invention calculates dose in the body using three-dimensional Monte Carlo transport. Neutrons, protons, deuterons, tritons, helium-3, alpha particles, photons, electrons, and positrons are transported in a completely coupled manner, using the LLNL-developed Monte Carlo All-Particle Method (MCAPM). The major elements of the invention include: computer hardware, a digital data file containing the description of the patient (a CT scan), a description of the radiation source, Monte Carlo transport software, and digital output files containing dose distributions.

The user can define the Cartesian transport mesh either manually or from a computed tomography (CT) scan of the patient. If the transport mesh is obtained from a CT scan, the x and y zone dimensions are defined as the dimensions of each pixel on the CT slice, while the z dimension is the spacing between CT slices. Each zone within the mesh is assigned a material number which is associated with a specific atomic composition and density. Materials are assigned using a software thresholding algorithm based on ranges of CT numbers or can be assigned manually.

The radiation source can be defined as a set of external beams or internal radioactive sources. Each element of the radiation source (beam or internal source) is characterized by its shape and position in space, as well as the distribution in energy and direction of particles it emits.

For external beams, the radiation source is defined as a complex beam or set of beams in a standard clinical isocentric gantry and table geometry. The user specifies the accelerator gantry, collimator, and table angles, a well as the (x,y,z) location of the table/accelerator center of rotation (isocenter) in the transport mesh. The energy and direction of each particle are described at a plane in space (the beam definition plane) that is defined to be perpendicular to the ray connecting the radiation source and the gantry/table isocenter. FIG. 1B shows the relationship between the radiation source 5, collimator jaws 7, and beam definition plane 6. Radiation beam 1 from radiation source 5, on gantry 2, passes through beam definition plane 6, collimator jaws 7, compensator 8 and block 9 onto table 4. Particles are transported from the point source to the beam definition plane. The beam definition plane is divided into a series of concentric rings. Each concentric ring may have a different energy and angular distribution associated with it. Depending on where the particle lands on the beam definition plane, it is given a new energy and angle by sampling from energy and angular distributions chosen from digital computer libraries that include monoenergetic, monodirectional options as well as energy and angular distributions derived from Monte Carlo simulations of actual beam delivery systems. The angular distribution(s) chosen by the user modify the trajectory of the particle at the beam definition plane. The field shape is defined as the particles pass through collimator jaws and an optional compensator and/or field-shaping block. Transport of particles through the collimator jaws is accomplished by ray tracing, while Monte Carlo methods are used to transport through the compensator and block. Once each particle exits the beam collimation system (jaws, compensator, and block) it is transported to the patient mesh.

For internal encapsulated sources, particles are produced from point or line sources, with energies determined (sampled) from radioisotope decay data and angles taken from angular distributions determined from Monte Carlo simulations of actual sources. The position and direction of each internal source particle is determined from the user-specified position of the source in the patient.

The invention carries out Monte Carlo transport calculations in the patient coordinate system as follows. First, a particle is selected from the radiation source. Depending on its type, it is passed to the appropriate neutron, photon, electron/positron, or heavy charged-particle transport package, where it is tracked until it undergoes a collision. For charged particles (electrons, positrons and heavy charged particles), energy is deposited by combining the distance traveled with predetermined stopping power (slowing down) information. Each nuclear reaction and photon interaction is handled by calling the Monte Carlo All Particle Method (MCAPM) reaction physics package. Given an incident particle, this package returns the energies and angles of all secondary particles resulting from the collision. These particles are stored in the secondary bank. Control is then returned to the Monte Carlo tracker, which selects a particle from the secondary bank or, when the bank is exhausted, from the radiation source. This process continues until all particles in the source and secondary bank have been followed.

The MCAPM software package is a system of data and algorithms that accomplishes the particle collision physics required for coupled Monte Carlo simulation of many particle types. The nuclear and atomic data libraries mentioned above describe the interaction of neutrons, photons, electrons, and heavy charged-particles with matter. Each interaction may result in the production of any of these particles. Additional data describing electron Coulomb interactions are included in the present invention.

Although neutron and heavy charged-particle cross-sections are averaged over energy groups or bins, each particle possesses a discrete energy value, allowing the collision kinematics to be performed on a continuous energy basis. This scheme exploits the strengths of both the pure continuous energy method (storing as much information as necessary to completely describe the energy dependency of each collision parameter) and the pure multi-group method (storing all collision parameters on an energy group or bin basis), allowing a smaller cross section database and while retaining accurate kinematics. Photon cross-sections are interpolated between discrete energy points. Neutrons and photons are transported using standard analog Monte Carlo methods. Energy transferred to particles that are not being tracked is deposited locally, with expected energy deposition providing variance reduction.

For heavy charged-particles, nuclear reactions and large-angle Coulomb scattering are treated on an event-by-event basis, while all other Coulomb interactions are accounted for with the condensed history method. The condensed history method uses transport physics ideas to combine the effects of multiple interactions as a particle travels a specified distance. In order to account for the multiple Coulomb collisions that occur within a charged particle condensed history step, the particle's energy and trajectory are modified using Gaussian like distributions with variances determined from the Rutherford scattering cross section (energy straggling) and from the Highland approximation to a Moliere distribution (multiple scattering).

Electron and positrons are transported using a traditional Class II condensed history method. Large-angle Coulomb scattering and bremsstrahlung production are modeled on an event-by-event basis, while all other Coulomb interactions are accounted for with the condensed history method. After each condensed history step, the electron's (or positron's) trajectory is modified by sampling from a Moliere distribution. The invention may in the future use the Macro Response Monte Carlo Method as an alternative to condensed history.

The Monte Carlo transport package calculates the energy deposited from the radiation source, creating a three-dimensional Cartesian map of energy deposited in the patient. When the Monte Carlo calculations are complete, the energy deposition map is converted to a map of absorbed dose, and is reported back to the user (client treatment planning code).

Input (description of the patient and radiation sources, and user options for code control) and output (a three-dimensional dose map) are read and written in a set of files that conform to the Specifications for Tape/Network Format for Exchange of Treatment Planning Information, Version 3.00 (Jan. 10, 1994), currently maintained by the NCI Prostate Collaborative Working Group RTOG 3D QA Center, Washington University in St. Louis. These files will be referred to as AAPM standard files. The form of input and output data may change in the future in order to accommodate new industry standards or to allow more direct linkage to commercial patient treatment planning system.

BRIEF DESCRIPTION OF THE DRAWINGS

FIGS. 16 through 19 describe the subroutines that make up the All-Particle Tracker (MCXEC) 22.

DETAILED DESCRIPTION OF THE INVENTION

The invention calculates the radiation dose in the body using three-dimensional Monte Carlo transport. Neutrons, protons, deuterons, tritons, helium-3, alpha particles, photons, electrons, and positrons are transported in a completely coupled manner, using the Lawrence Livermore National Laboratory (LLNL) developed Monte Carlo All-Particle Method (MCAPM). The major elements of the invention include: computer hardware and software, a digital data file containing the description of the patient (a CT scan), a description of the radiation source, nuclear and atomic interaction databases, Monte Carlo transport software, and digital output files containing dose distributions.

An example of the type of computer hardware usable in accordance with the invention includes: a generic UNIX based workstation with one or more Central Processing Units (CPUs) operating under UNIX (the invention is currently operational on the following: Sun Microsystems SPARC series, Silicon Graphics SGI-R4000 series, IBM RS6000 series, etc.), 128 Mbytes of random access memory available to each processor, a 1 Gbyte internal hard disk to store input/output information required and generated by the invention, a color monitor to view the CT scan and dose results (preferably at least 17 inches) and a standard keyboard for program execution and control.

Figure 1A:
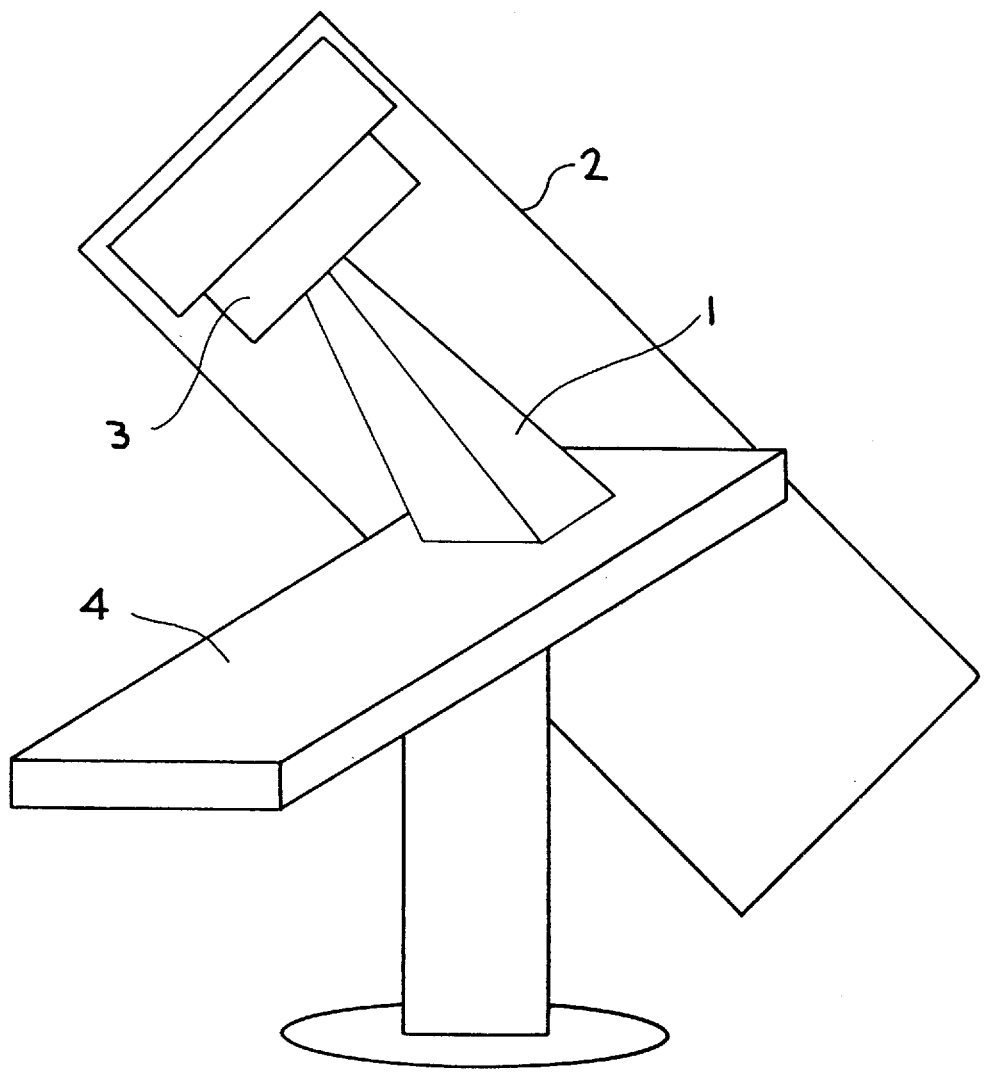
FIG. 1A shows the relationship between the gantry, collimator, table, and radiation beam for external beam radiation therapy delivery.
Figure 1B:
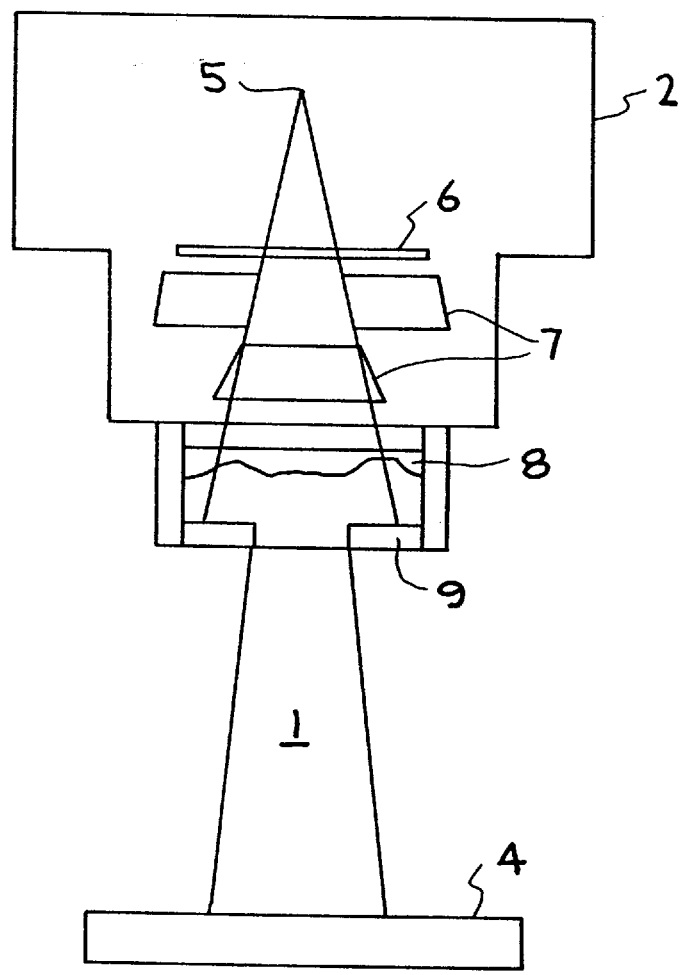
FIG. 1B shows the relationship between the source, collimator, and beam definition plane.
Figure 2:
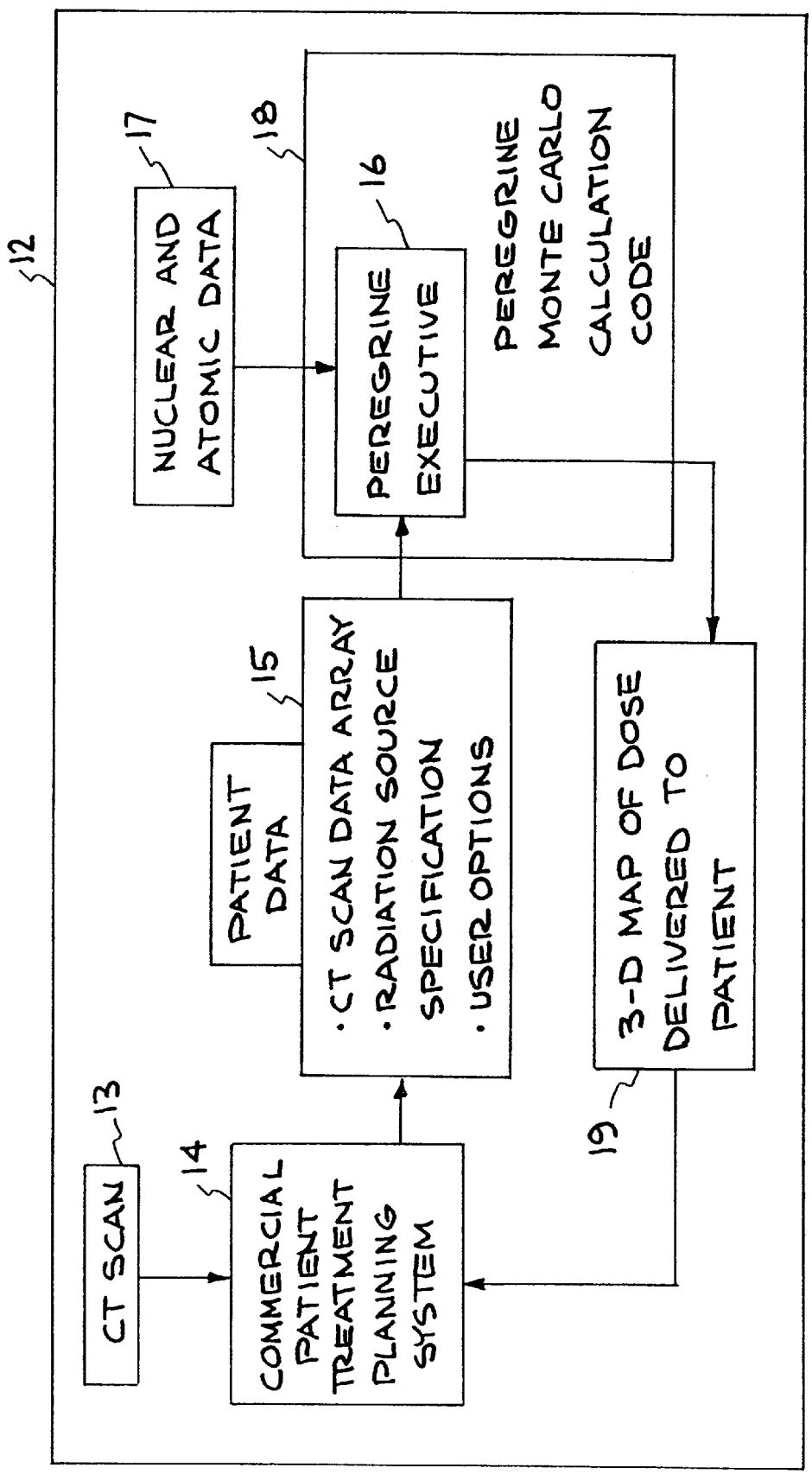
FIG. 2 shows a top-level view of the process flow of the present invention.

FIG. 2 shows a top-level view (12) of the process and the invention. A Cartesian transport mesh is defined either manually or from a computed tomography (CT) scan (13) and input into a commercial patient treatment planning system (14). Additional data about the patient, the radiation source prescribed, and other user options are included with the CT data (15) and passed to the executive (16). In addition, nuclear and atomic data (17), are input into the Executive program (16), which manages the Monte Carlo dose calculations process (18) and returns to the Planning System (14) a 3-D map (19) of the dose delivered to the patient.

Figure 3B:
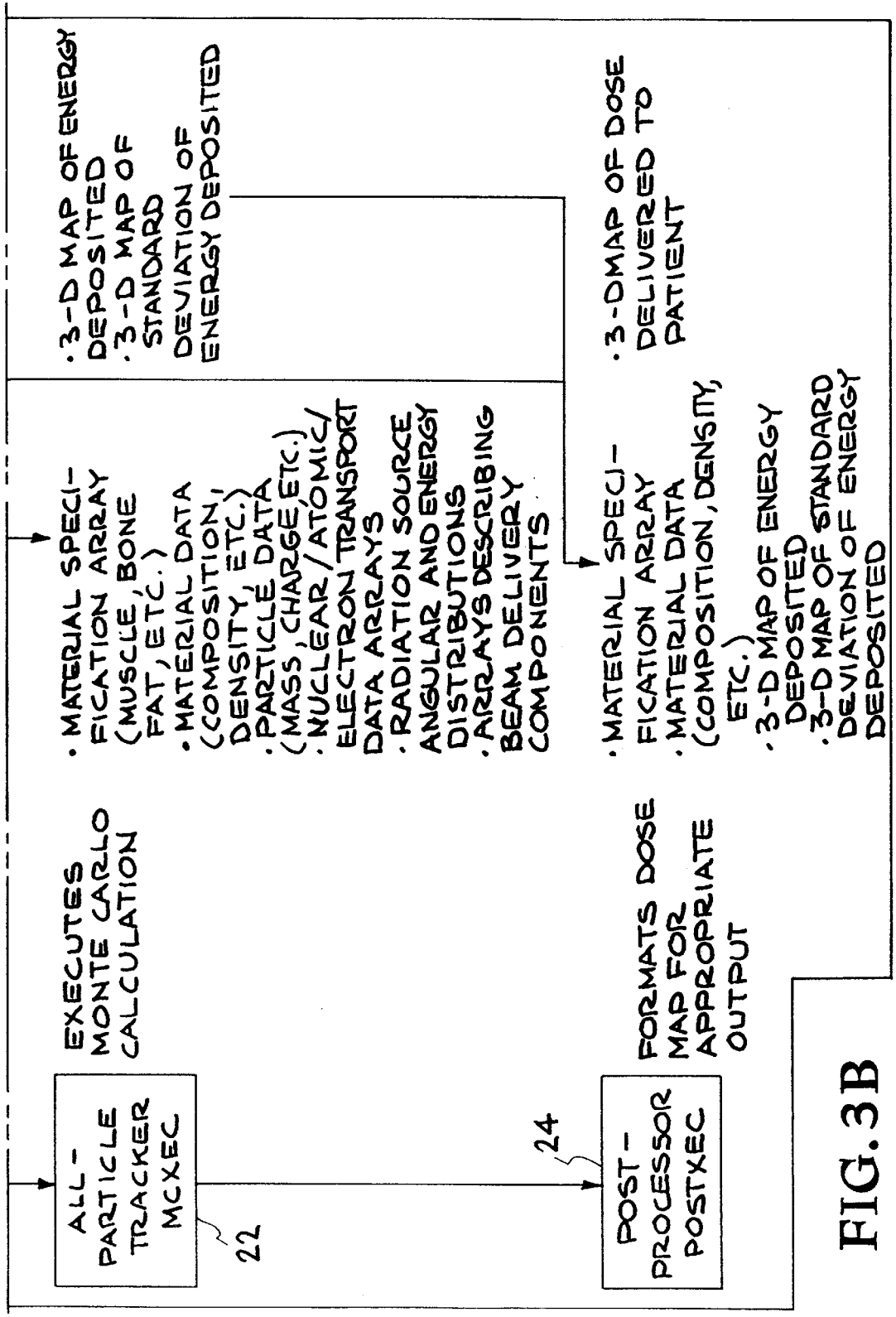
FIG. 3 shows the code at its highest level.

FIG. 3 is a structure diagram of the code at its highest level. The executive process, PGXEC (16) manages three major functions: (i) the generation process (Generator 20 called GENXEC) which sets up all the patient data, radiation source data, and physics data needed to do the dose calculation, (ii) the All Particle Monte Carlo physics dose calculation (All Particle Tracker 22 called MCXEC), and (iii) the final process of formatting the dose calculation and passing it back for viewing (Post Processor 24 called POSTXEC. The generator (20), all-particle tracker (22) and post-processor (24) are all controlled by the executive program (16).

Referring to FIG. 3, the executive program 16 manages the three highest level subroutines; the generator (20), the all-particle tracker (22) and the post-processor (24). Input to the generator (20) includes: (i) a CT scan data array, (ii) nuclear/atomic/electron data, (iii) the radiation source specification and (iv) user options. The output from the generator (20) includes: (i) a material specification array (muscle, bone, fat, etc.), (ii) material data (composition, density, etc.), (iii) particle data (mass, charge, etc.), (iv) a nuclear and atomic transport data array, (v) radiation source angular and energy distributions; and (vi) arrays describing beam delivery components. The output from generator (20) is input to the all-particle tracker (22) which executes the Monte Carlo calculation and provides output as a 3D map of energy deposited and a 3D map of standard deviation of energy deposited. The output from the all-particle tracker is provided as input to the post-processor 24, which formats a dose map for the appropriate output. Some of the output from Generator (20) is also provided as input to post-processor 24 in the form of a material specification array and material data (composition, density, etc.). The output from post-processor 24 is a 3D map of the dose that has been delivered to the patient.

Figure 4A:
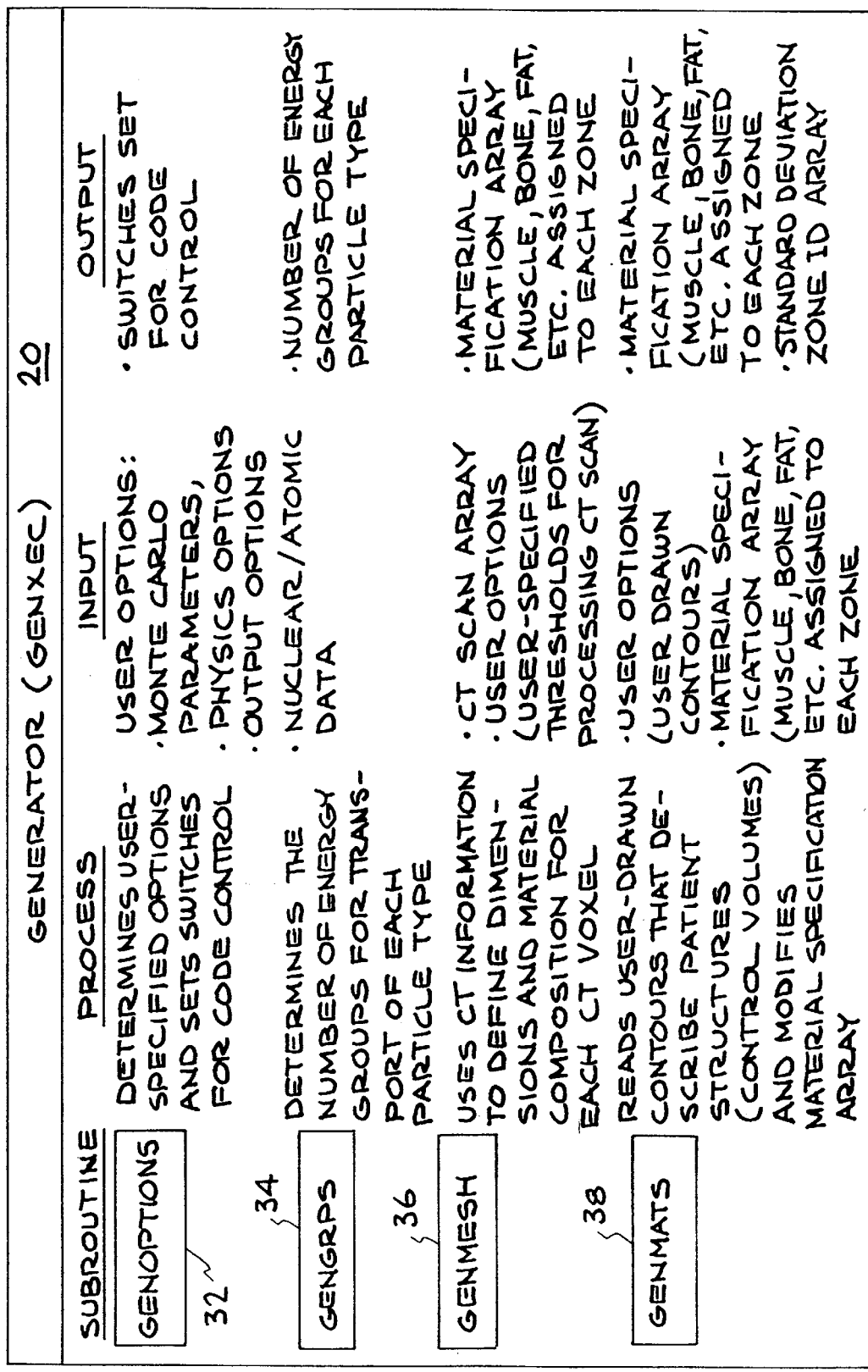
FIGS. 4A and 4B describe the subroutines that make up Generator 20.
Figure 4B:
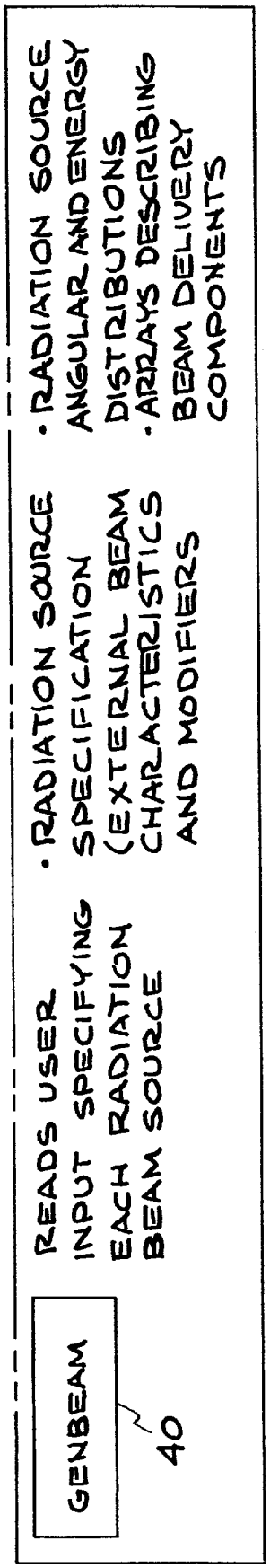
Figure 4C:
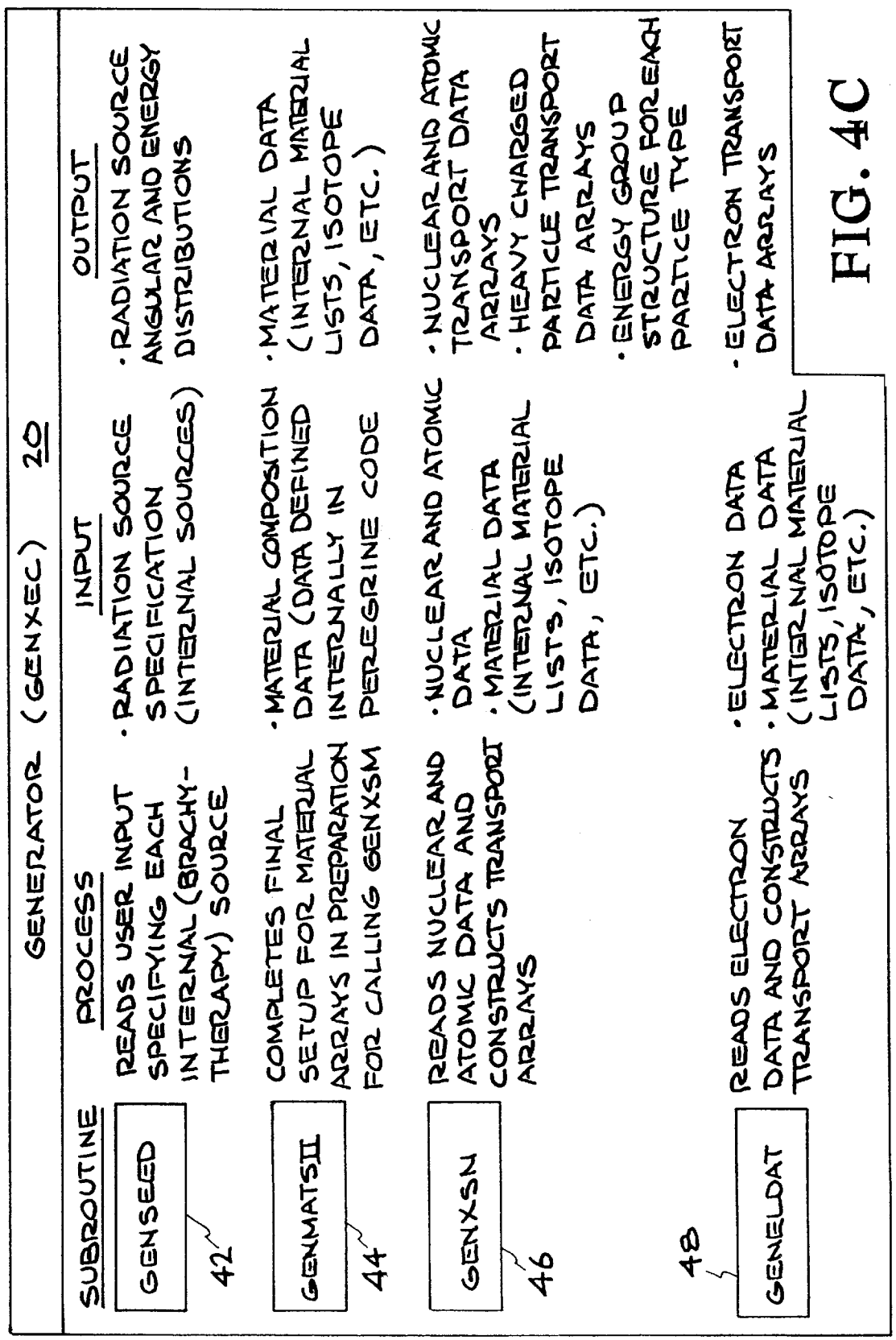

FIGS. 4A and 4B describe the subroutines that make up Generator 20. GENOPTIONS (32) determines user-specific options and sets switches for code control. Referring to FIG. 4A, input to GENOPTIONS (32) include user options: (i) Monte Carlo parameters, (ii) physics options and (iii) output options. The output of GENOPTIONS (32) sets the switches for code control. GENGRPS (34) determines the number of energy groups for transport of each particle type. Input to GENGRPS (34) is nuclear/atomic data. GENMESH (36) uses CT information to define dimensions and material composition for each CT voxel. The input to GENMESH (36) is a CT scan array and user options (user-specified thresholds for processing CT scan). The output from GENMESH (36) is a material specification array (muscle, bone, fat, etc. assigned to each zone). GENMATS (38) reads user-drawn contours that describe patient structures (control volumes) and modifies the material specification array. User options (user-drawn contours) and a material specification array (muscle, bone, fat, etc., assigned to each zone) are input into GENMATS (38). The output of GENMATS (38) is a modified material specification array and the standard deviation zone ID array. GENBEAM (40) reads user radiation source specification input specifying each radiation beam source. The output of GENBEAM (40) is the radiation source angular and energy distributions and arrays describing beam delivery components.

Referring now to FIG. 4B, GENSEED (42) reads user input specifying each internal (brachytherapy) source (if specified). The input to GENSEED (42) is the radiation source specification (internal sources). The output of GENSEED (42) is radiation source angular and energy distributions. GENMATSII (44) completes the final setup for the material arrays in preparation for calling the subroutine 46. Its input is material composition data which is data defined internally in the software. The output from 44 is material data such as internal material lists, isotope data, etc. GENXSN (46) reads nuclear and atomic data and material and isotope data, and constructs arrays needed to do the physics of the transport. The output from GENXSN (46) is nuclear and atomic transport data arrays, heavy charged particle transport data arrays and an energy group structure for each particle type. GENELDAT (48) reads electron data and constructs transport arrays. Input to GENELDAT (48) includes electron data and material data and the output from the subroutine is electron transport data arrays.

Figure 5A:
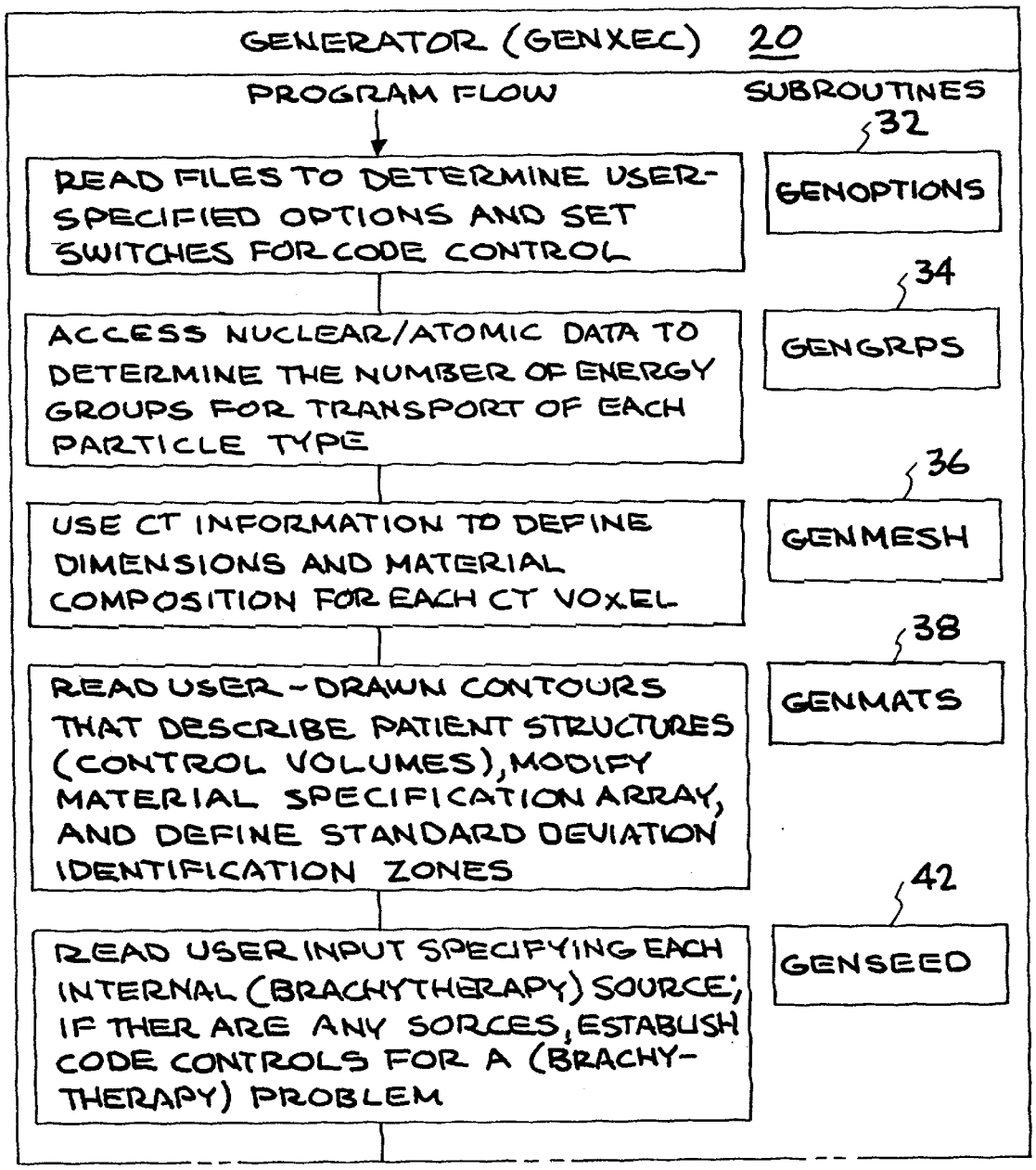
FIG. 5 shows the program flow that makes up Generator 20.
Figure 5B:
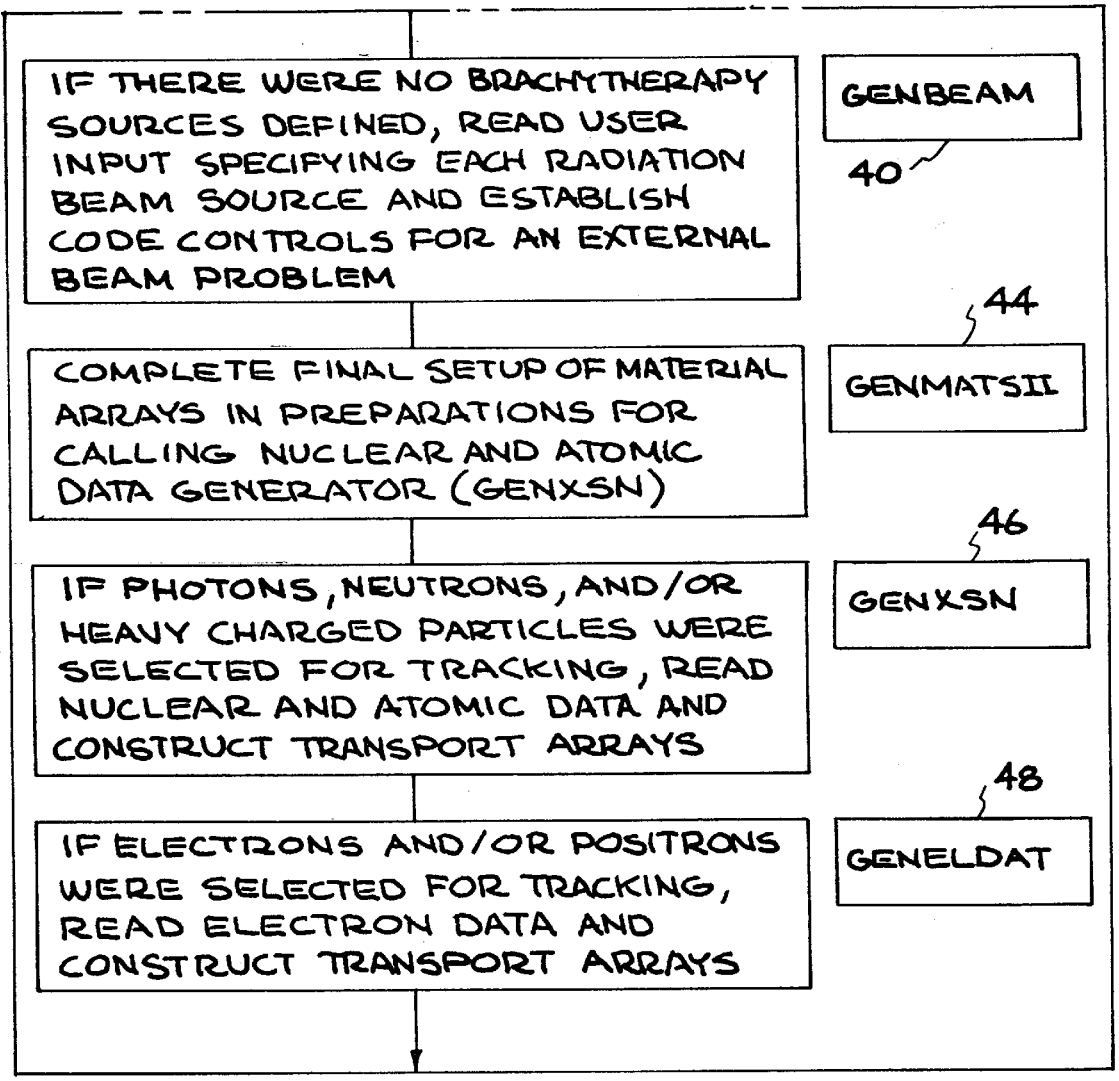

FIG. 5 shows the program flow that makes up Generator (20). GENOPTIONS (32) reads files to determine user-specified options and to set switches for code control. GENGRPS (34) accesses nuclear and atomic data to determine the number of energy groups for transport of each particle type. GENMESH (36) uses CT information to define dimensions and material composition for each CT voxel. GENMATS (38) reads user-drawn contours that describe patient structures such as control volumes, modifies the material specification array, and defines standard deviation identification zones. GENSEED (42) reads user input specifying each internal brachytherapy source; and if there are any sources, establishes code controls for a brachytherapy problem. If there were no brachytherapy sources defined in GENSEED (42), GENBEAM (40) reads user input specifying each radiation beam source and establishes code controls for an external problem. GENMATSII (44) completes the final setup for the material arrays in preparation for calling the nuclear and atomic data generator GENXSN (46). If photons, neutrons, and/or heavy charged particles were selected for tracking, GENXSN (46) reads nuclear and atomic data and constructs transport arrays. If electrons and/or positrons were selected for tracking, GENELDAT (48) reads electron data and constructs transport arrays.

Figure 6A:
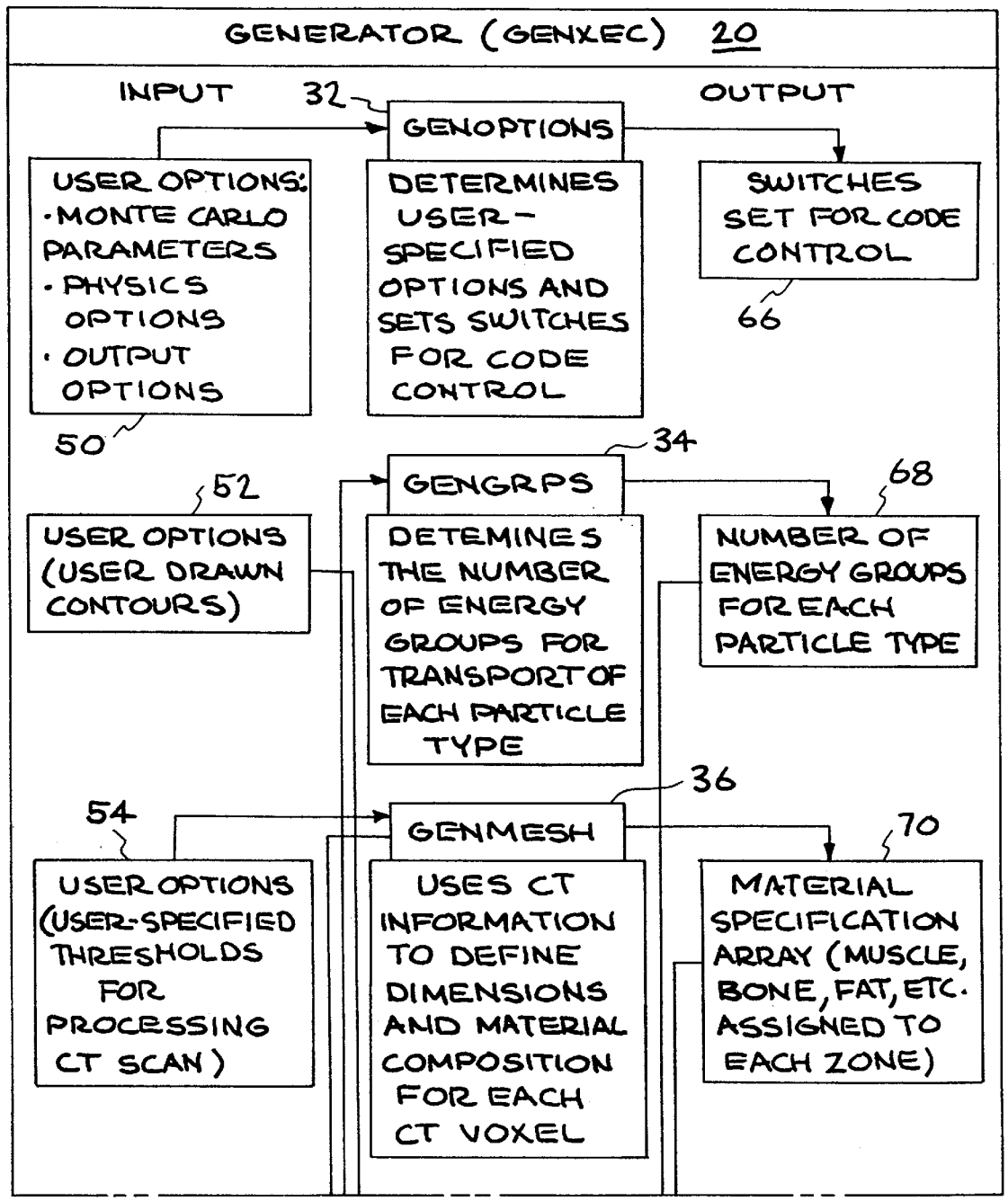
FIG. 6 shows another view of the program flow, data structure, output and subroutine functions of Generator 20.
Figure 6B:
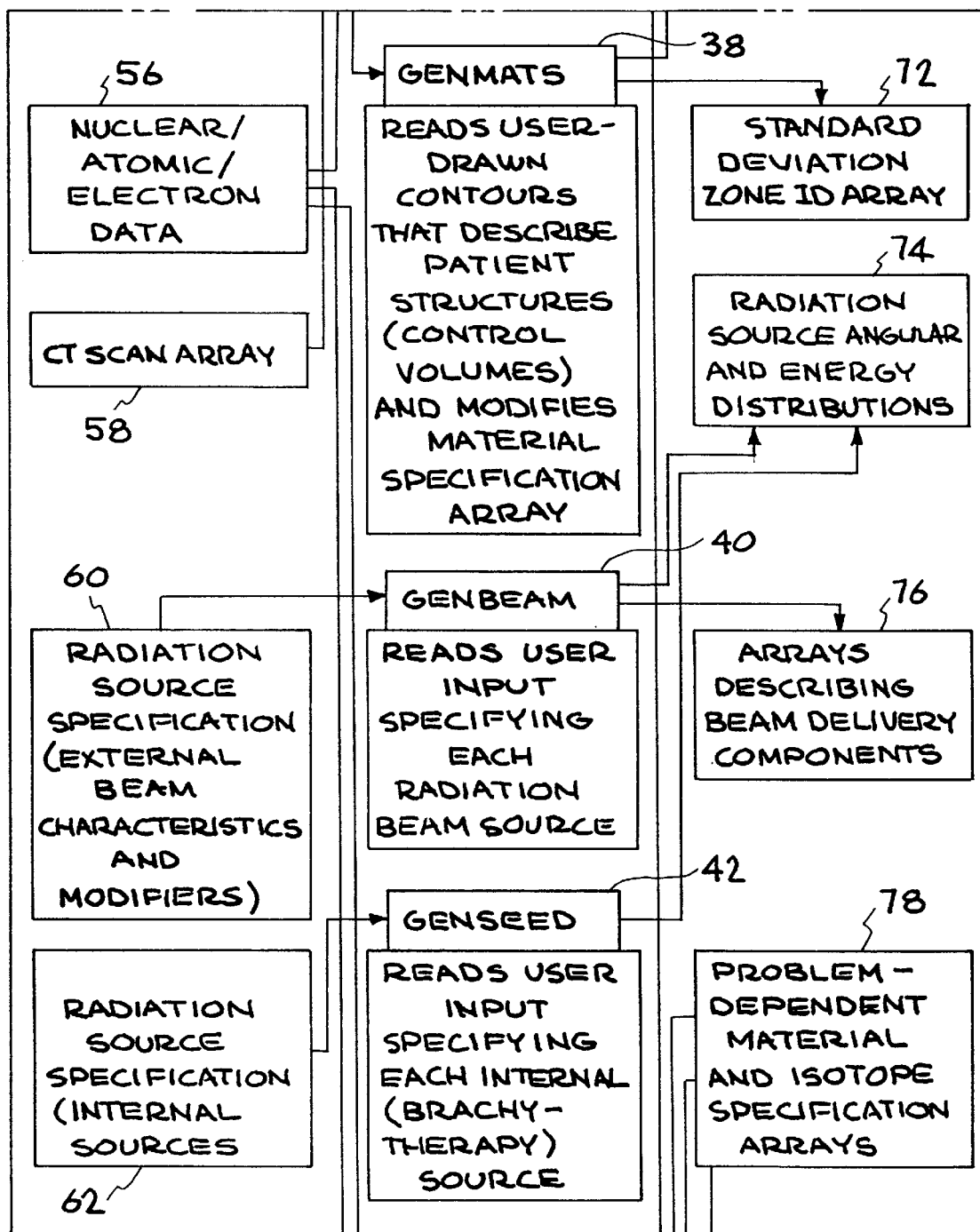
Figure 6C:
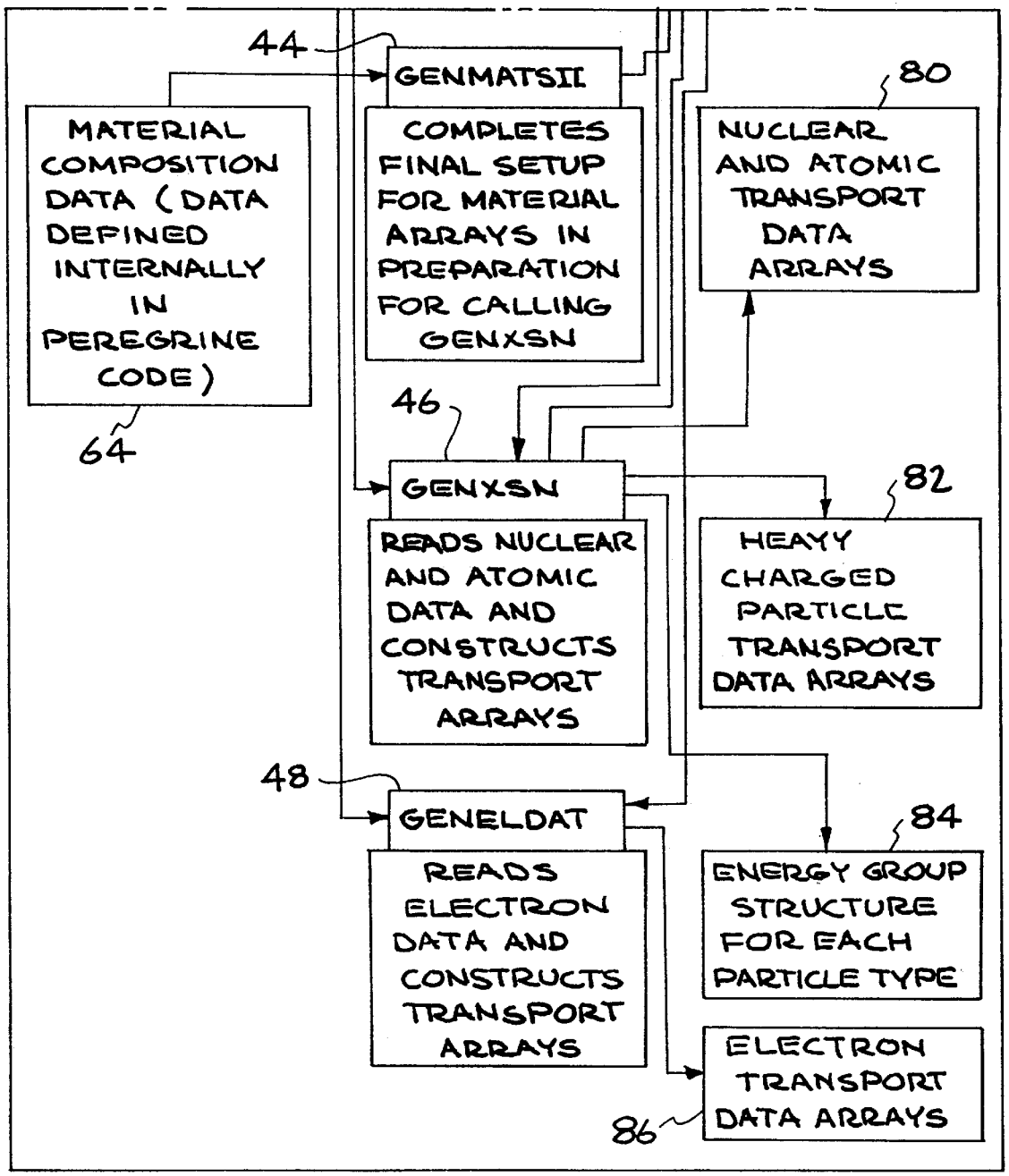

Still another view of the program flow, data structure, data output and subroutine functions of GENERATOR (20) are shown in FIG. 6. Input 50, comprising Monte Carlo parameters, physics options and output options is fed into GENOPTIONS (32), which determines user-specified options and sets switches for code control to produce output 66, which sets the switches for code control. Input 52, comprising user options such as user-drawn contours, is fed into GENMATS (38), which reads user-drawn contours that describe patient structures (control volumes) and modifies the material specification array to provide output 70, comprising a material specification array, and output 72 comprising a standard deviation zone ID array. Input 54, consisting of user options (user-specified thresholds for processing CT scan), is fed into GENMESH (36) which uses CT information to define dimensions and material compositions for each CT voxel. GENMESH (36) provides output 70 consisting of a material specification array (muscle, bone, fat, etc. assigned to each zone). Input 56 comprising nuclear/atomic/electron data is fed into GENGRPS (34), GENXSN (46) and GENELDAT (48). GENGRPS (34) determines the number of energy groups for transport of the particle type and provides the output 68 of the number of energy groups for each particle type. Output 68 is also fed into GENXSN (46) which reads nuclear and atomic data and constructs transport arrays. GENXSN (46) produces output 80, 82 and 84. Output 80 consists of nuclear and atomic transport data arrays. Output 82 consists of heavy-charged particle transport data arrays. Output 84 consists of an energy group structure for each particle type. Input 56, also fed into GENELDAT (48), produces output 86 which comprises electron transport data arrays. Input 58, comprising a CT scan array is also fed into GENMESH (36) along with input 54. Input 60 comprising radiation source specification (external beam characteristics and modifiers) is fed into GENBEAM (40) which reads user input specifying each radiation beam source to produce the output 74 and 76. Output 74 consists of radiation source angular and energy distributions and output 76 consists of arrays describing beam delivery components. Input 62 comprising radiation source specification (internal sources) is fed into GENSEED (42) and produces output 74 consisting of radiation source angular and energy distributions. Input 64 consisting of material composition data (data defined internally in this code) is fed into GENMATSII (44) which completes the final setup for material arrays in preparation for calling GENXSN (46). Output 78 from GENMATSII (44) comprises problem-dependent material and isotope specification arrays and is fed into GENXSN (46) and GENELDAT (48).

Figure 7:
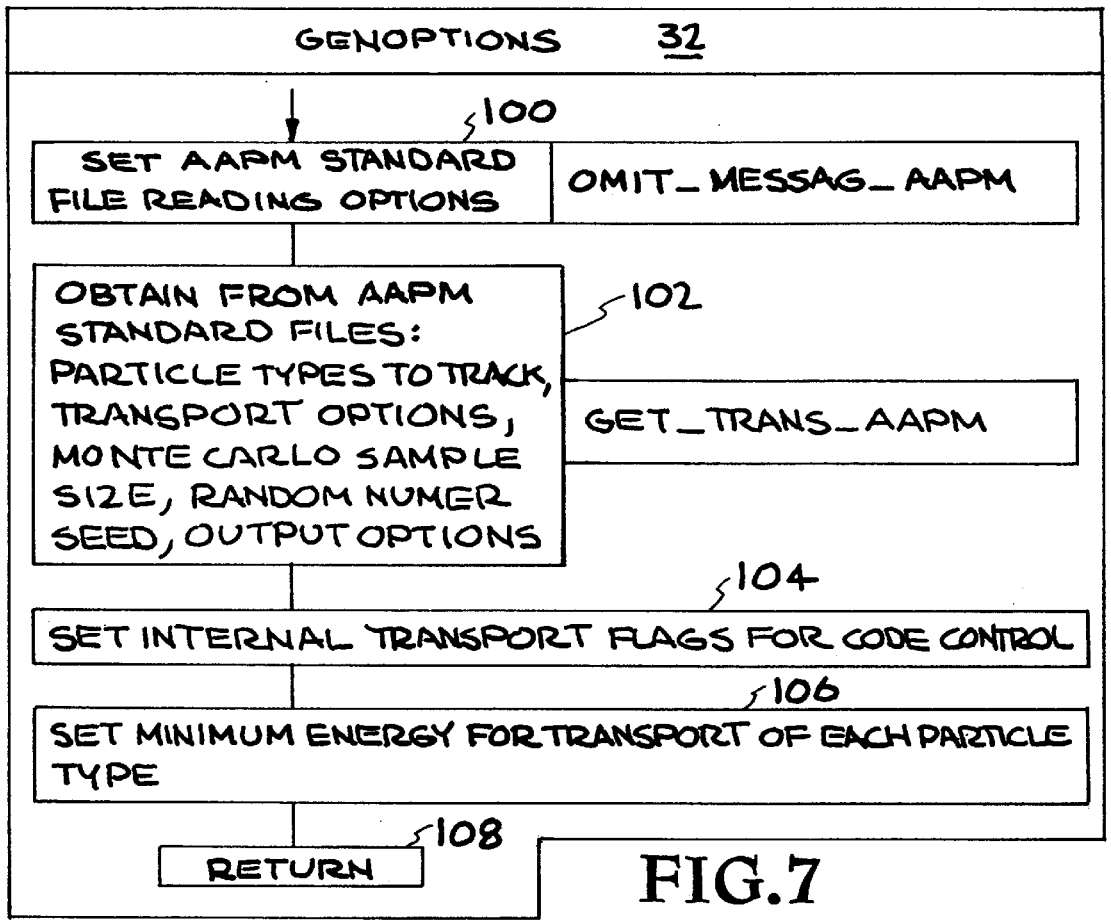
FIGS. 7 through 15 show detailed views of the program flow of each subroutine of Generator 20.
Figure 8:
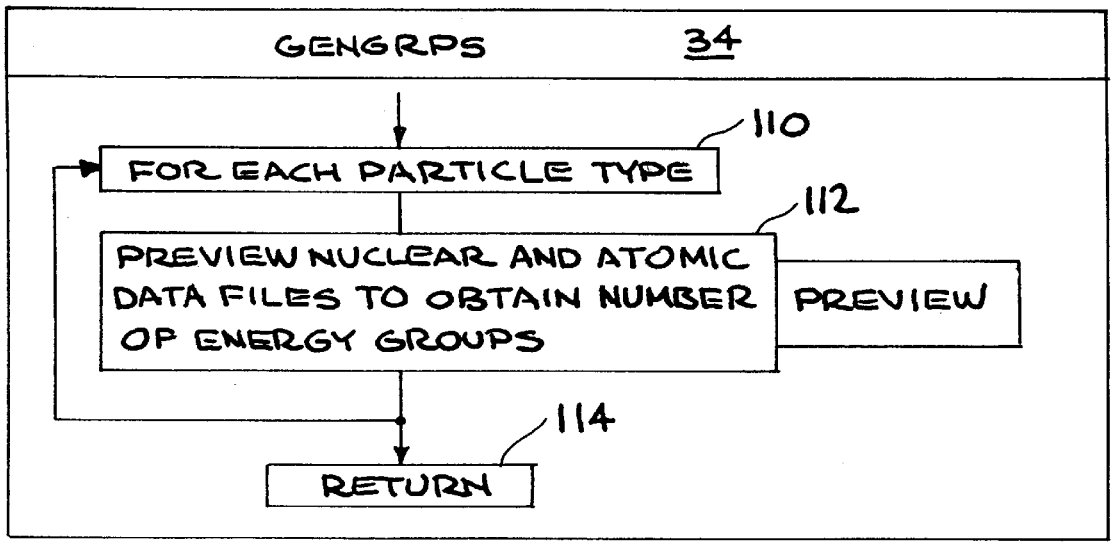
Figure 9:
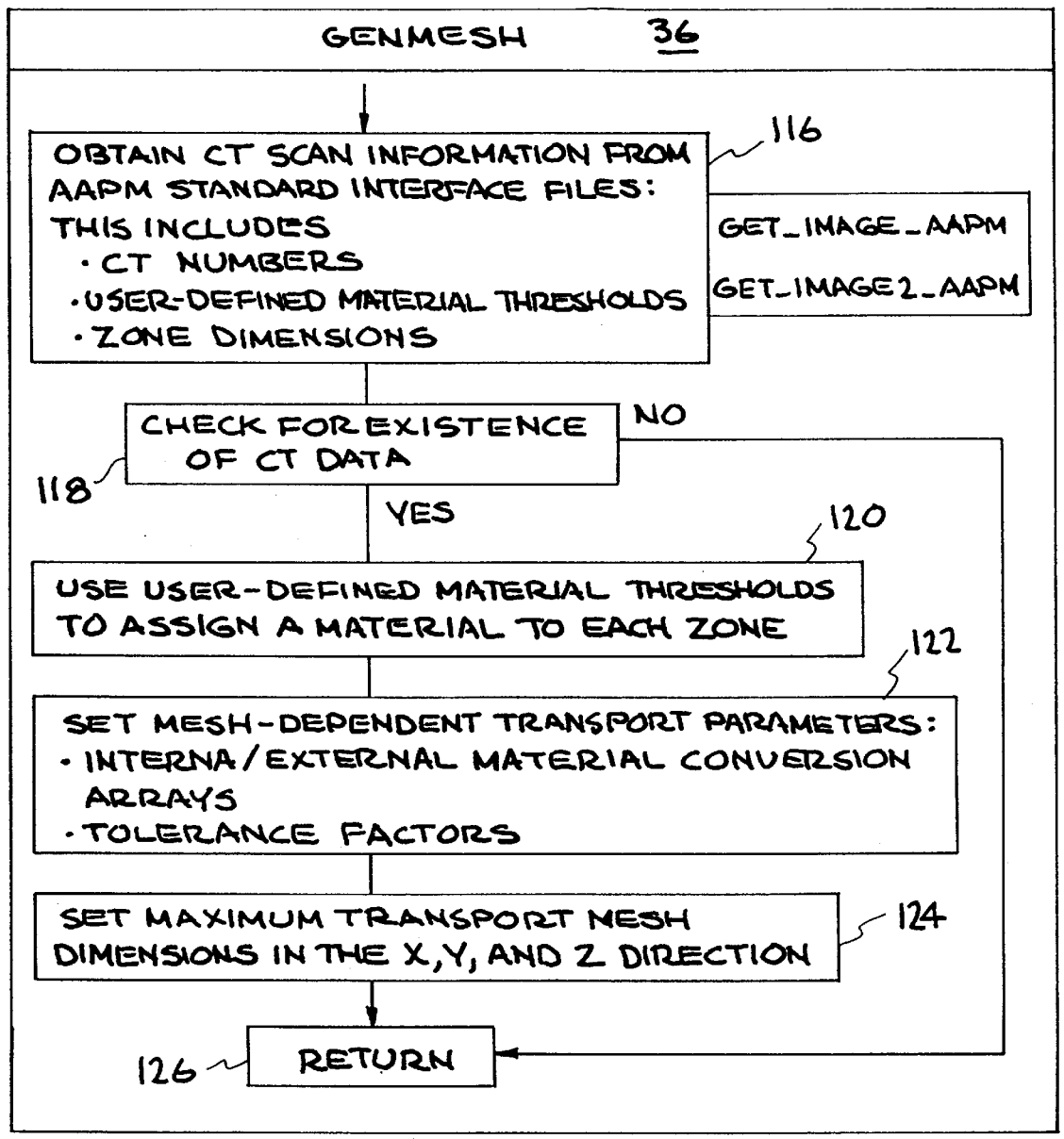

Detailed views of the program flow of each subroutine of the Generator 20 are shown in FIGS. 7 through 15. As shown in FIG. 7, GENOPTIONS (32) begins by setting the AAPM standard file reading options (100). Next (102), the following items are obtained from AAPM standard files: particle types to track, transport options, Monte Carlo sample size, random number seed and output options. The internal transport flags are then set for code control (104). The minimum energy is then set for transport of each particle type (106). The program flow then returns (108) to the calling routine (Generator 20). In FIG. 8, GENGRPS (34) previews nuclear and atomic data files (112) for each particle type (110) to obtain the number of energy groups. After each particle type has been previewed, the flow of the program returns (114) to the calling routine. Referring to FIG. 9, subroutine GENMESH (36) obtains CT scan information (116) from AAPM Standard Interface files, which includes the CT numbers, user-defined material thresholds and zone dimensions. The existence of CT data is checked (118) and if there is no CT data, the program returns (126) to the calling routine (Generator 20). If there is CT data, user-defined material thresholds are used (120) to assign a material to each zone. Mesh-dependent transport parameters including internal/external material conversion arrays and tolerance factors are then set (122). Next, maximum transport mesh dimensions in the x, y, and z direction are set (124). The program flow then returns (126) to the calling routine.

Figure 10:
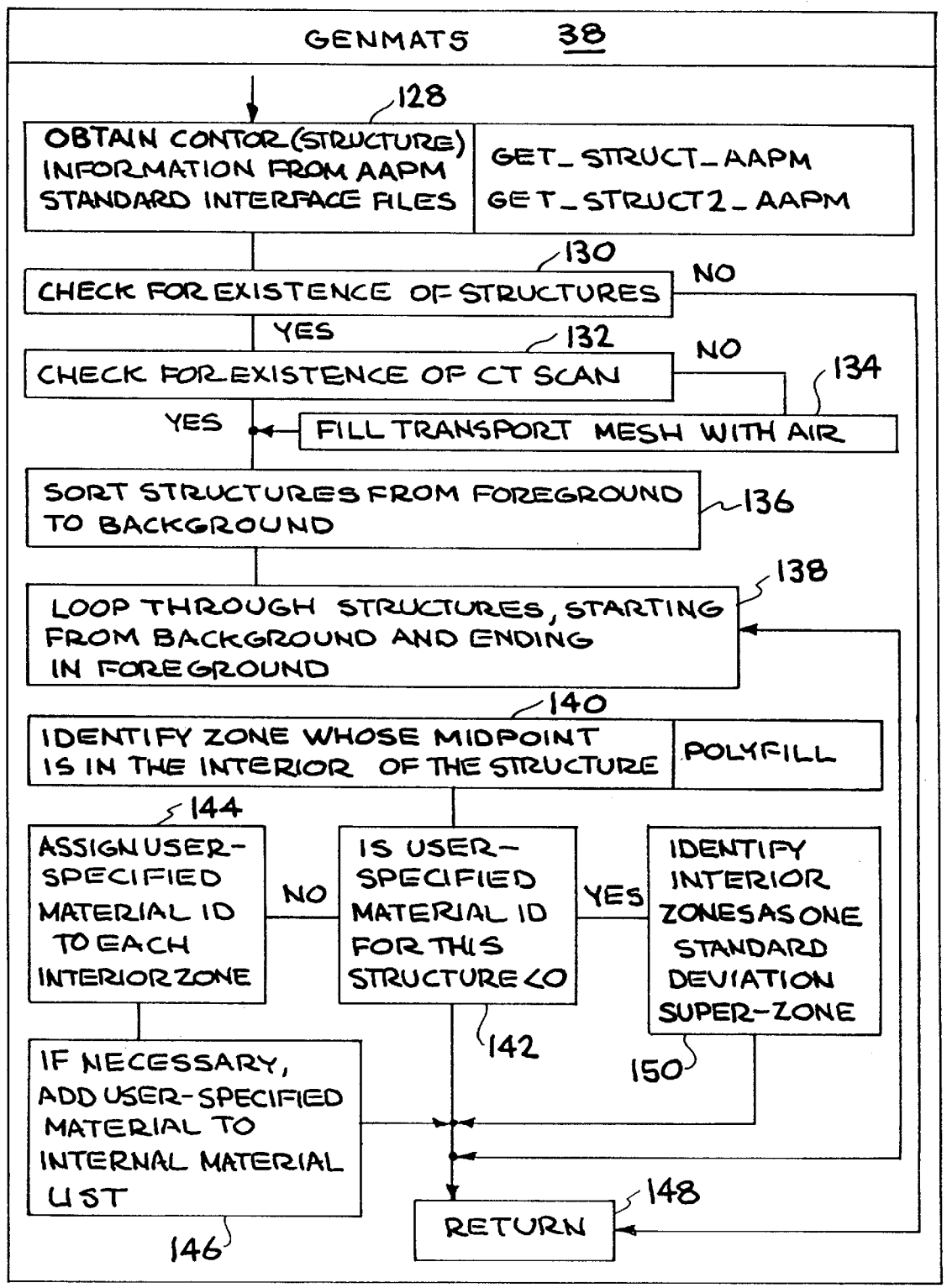

Referring to FIG. 10, GENMATS (38) obtains contour (structure) information from AAPM Standard Interface files (128). The program then checks (130) for the existence of structures and if there are no structures, the program returns (148) to the calling routine (Generator 20). If structures exist, then GENMATS (38) checks (132) for the existence of a CT scan. If there is no CT scan, the transport mesh is first filled with air (134). Next the structures (136) are sorted from the foreground to the background. The routine then loops (138) through the structures, starting from background and ending in foreground. In this loop, the zone whose midpoint is the interior of the structure is identified. It is determined if user-specified material identification for this structure is less than 0 (142). If the number is not less than 0, a user-specified material ID is assigned (144) to each interior zone. Then, the user-specified material is added (146) to the internal material list if necessary. The program then returns to loop through the structures (138). If the user-specified material ID for the structure is less than 0, the interior zones are identified (150) as one standard deviation super-zone. The program flow then returns to loop through the structures (138). After looping through the structures, starting from the background to the foreground, until all the structures have been processed, GENMATS 38 returns (148) to the calling routine (Generator 20).

Figure 11A:
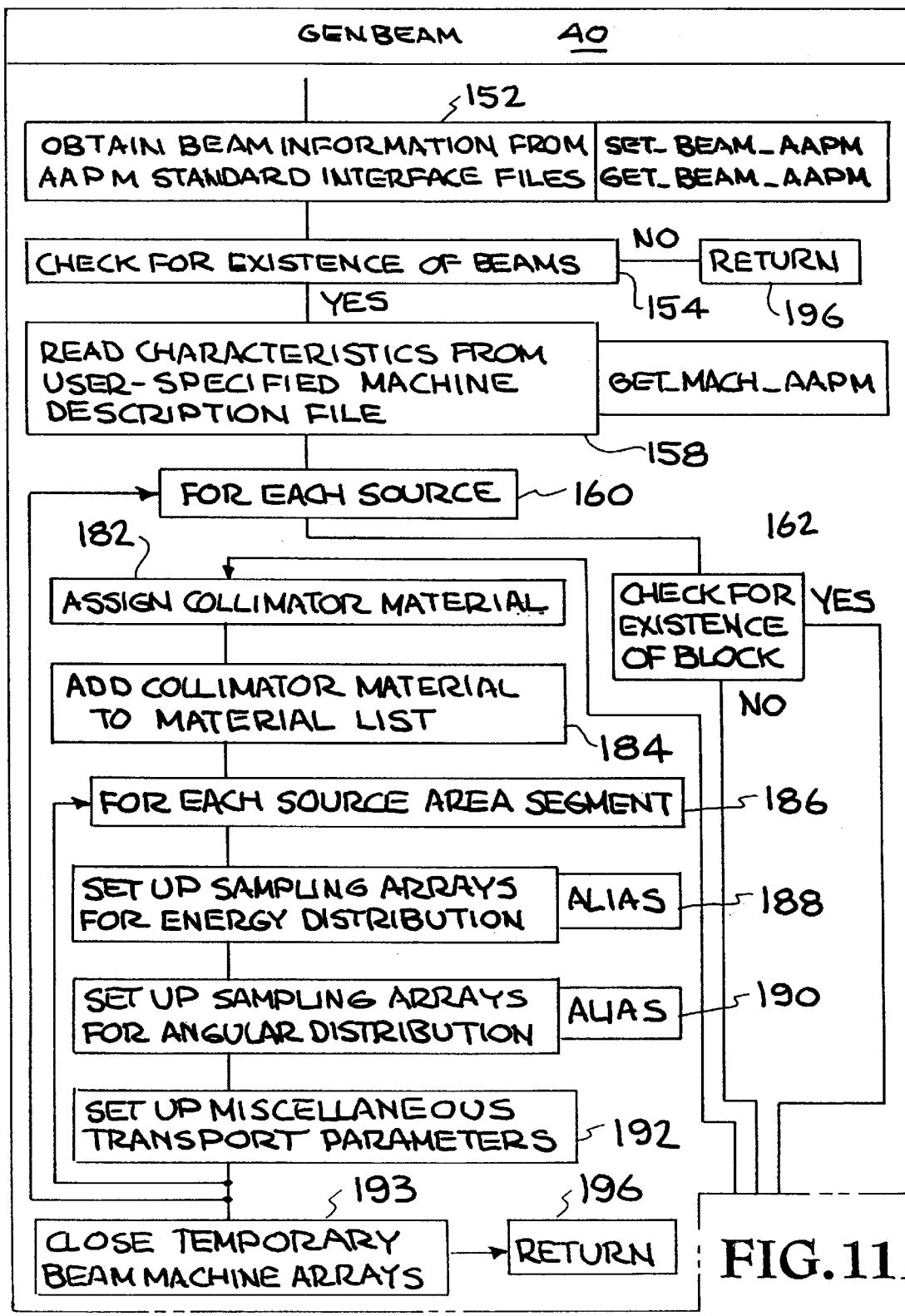
Figure 11B:
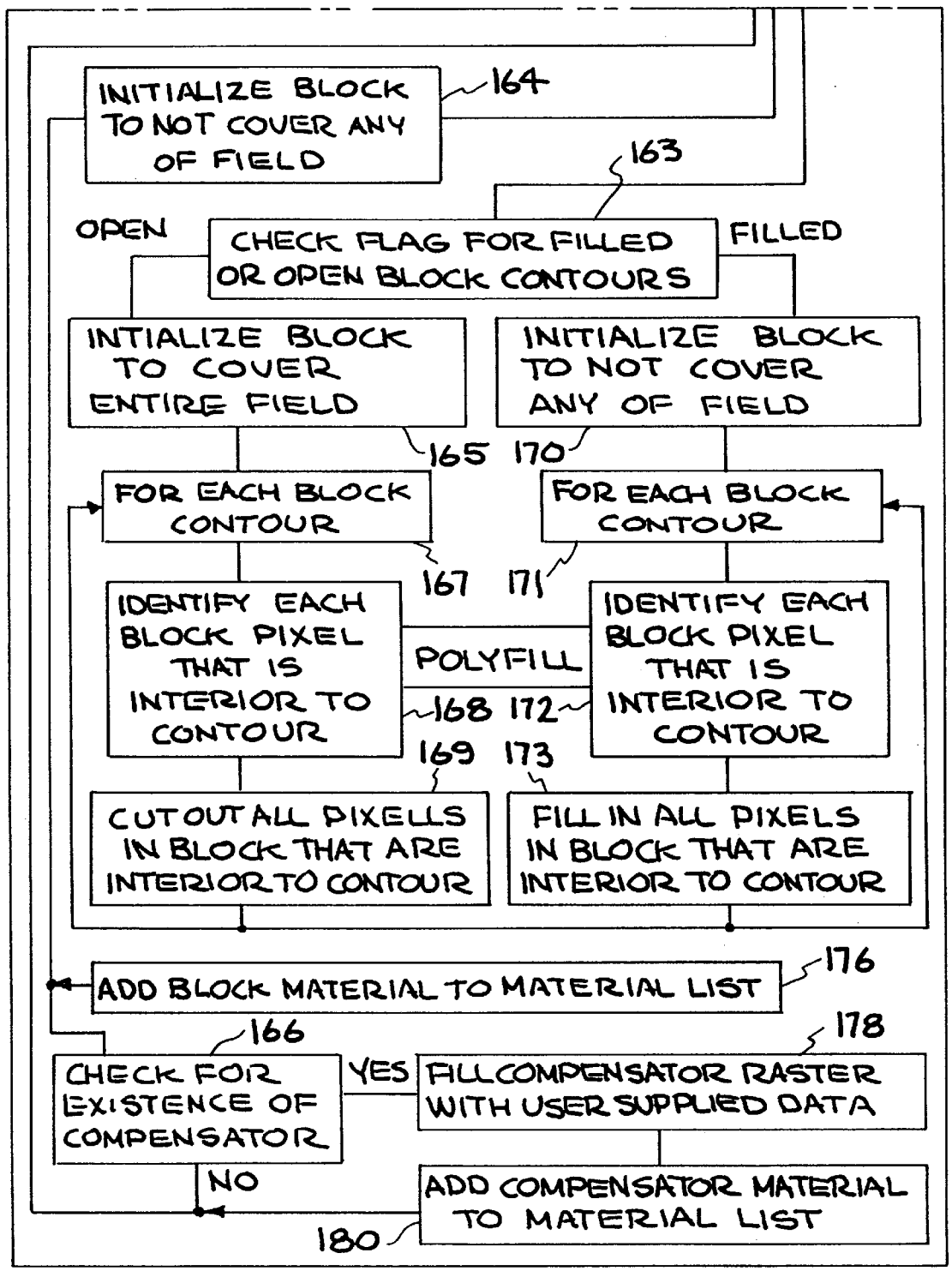

Referring now to FIG. 11, GENBEAM (40) begins (152) by obtaining beam information from AAPM Standard Interface files. The existence of beams is determined (154) and if there are none, the routine returns (196) to the calling routine. If beams do exist, characteristics are read (158) from a user-specified machine description file. For each source at 160, it is determined if a block exists (162). If no block exists, a block is initialized (164) to not cover any part of the field. The existence of a compensator is then checked (166). If a block exists (162), a control flag is checked for filled or open block contours (163). If open contours are specified, the block is initialized (165) to cover the entire field. For each block contour (167), each block pixel that is interior to the contour is identified (168). All pixels that are in the block that are interior to the contour are cut out (169). If filled contours are specified (163), the block is initialized (170) to not cover any of the field. For each block contour (171), each block pixel that is interior to the contour is identified (172). All pixels that are in the block that are interior to the contour are filled (173). Block material is then added (176) to the material list. The existence of the compensator is checked (166). The compensator raster is then filled (178) with user-supplied data, which specifies the thickness of the compensator at each pixel in the raster. Compensator material is added (180) to the material list. Collimator jaw material is assigned (182) and added to the material list (184). For each source area segment (186), sampling arrays are set up for the energy distribution (188) and angular distribution (190). Miscellaneous transport parameters are then set up (192). When all source area segments are looped, then flow returns to (160) for additional sources. After all characterization of all beams is complete, temporary beam/machine arrays are closed (193) and the program flow returns (196).

Figure 12:
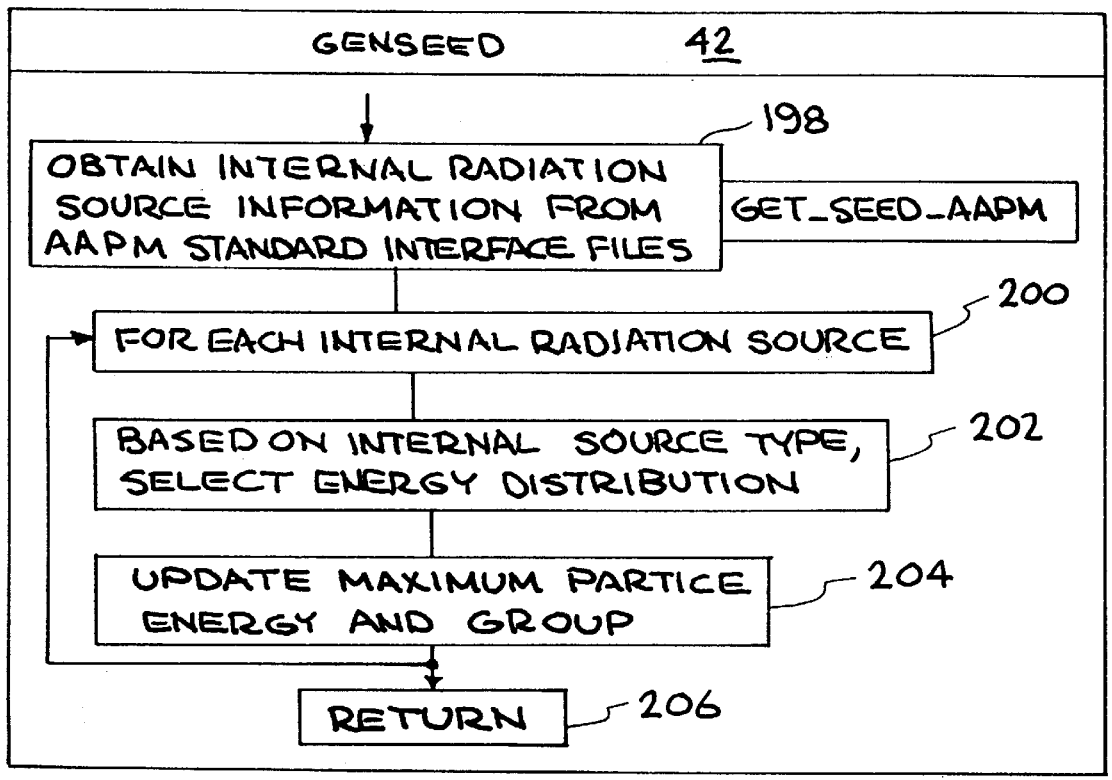

Referring now to FIG. 12, GENSEED (42) begins by obtaining internal radiation source information from AAPM Standard Interface files (198). For each radiation source (200), the energy distribution is selected (202) based on the internal source type. The maximum particle energy and group is then updated (204). Program flow then returns to step 200 for each internal radiation source until exhausted and then returns (206) to the calling routine.

Figure 13:
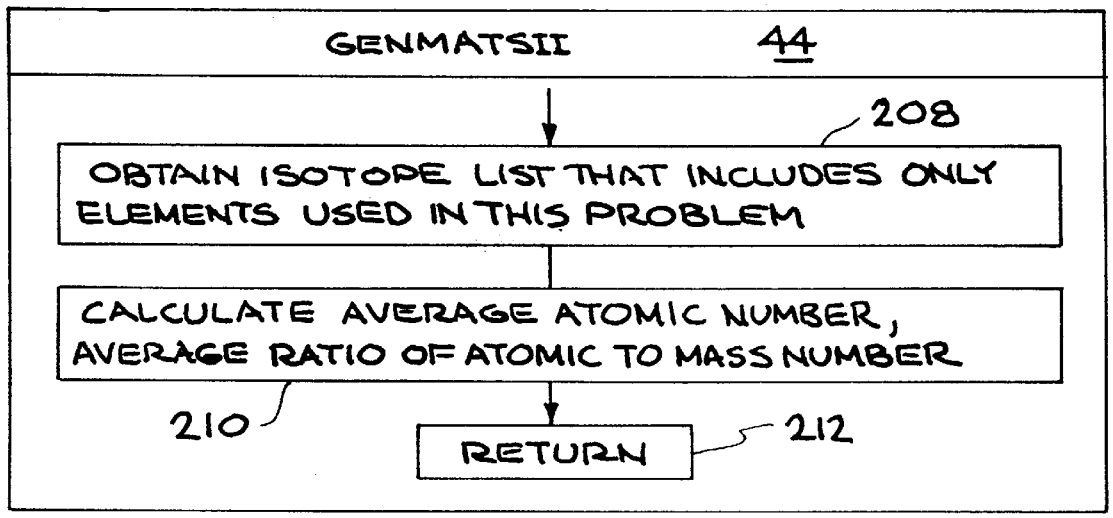

Referring to FIG. 13, GENMATSII (44) obtains isotope lists that include only elements used in this problem (208). The average atomic number and the average ratio of atomic to mass number are then calculated (210), and the program flow returns (212) to the calling routine.

Figure 14A:
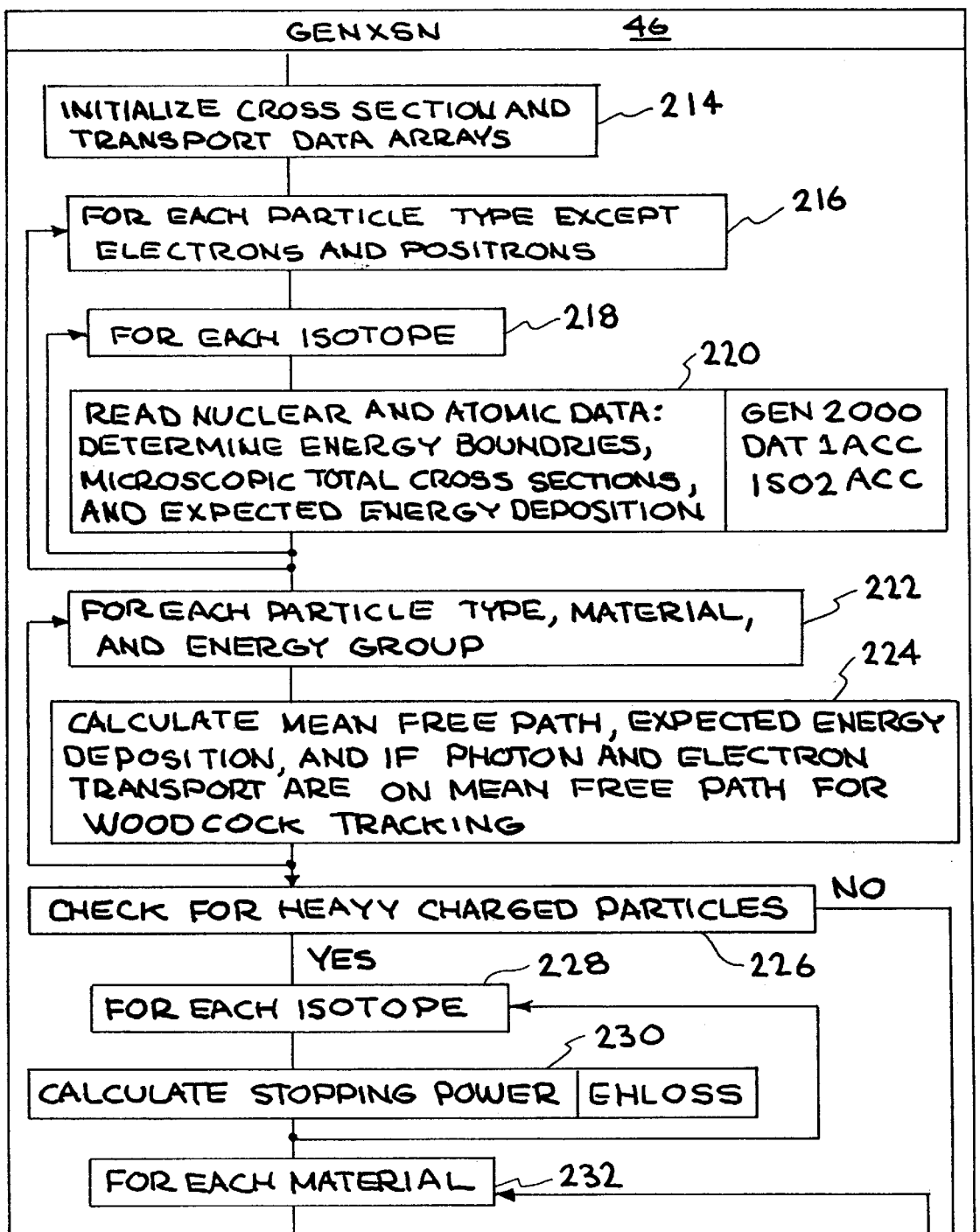
Figure 14B:
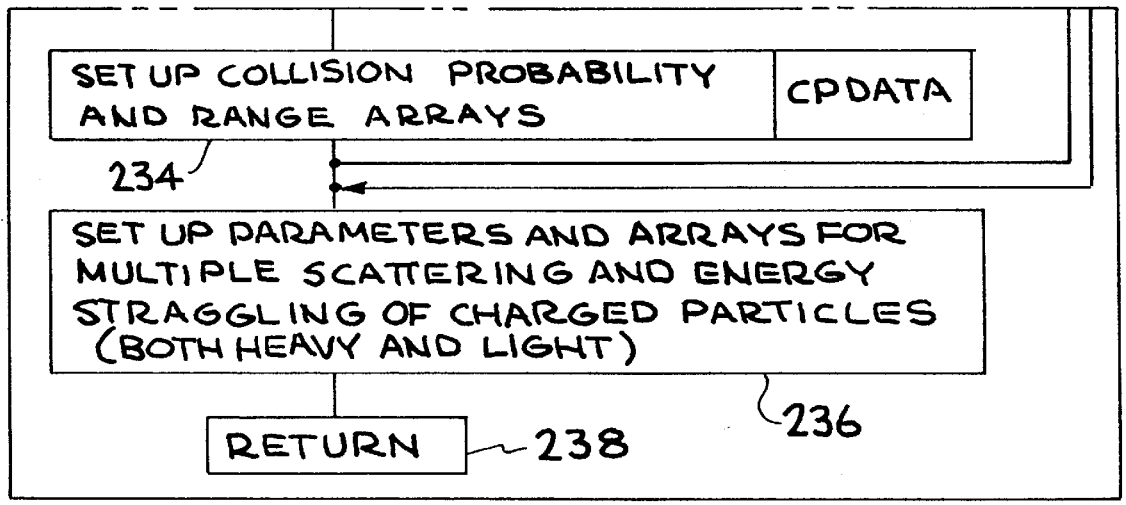

Referring now to FIG. 14, GENXSN (46) begins (214) by initializing the cross sections and transport data arrays. At step 216 for each particle type except electrons and positrons, for each isotope at step 218, step 220 reads nuclear and atomic data, determines energy boundaries, microscopic total cross sections, and expected energy depositions. Step 220 returns to step 216 for each particle type except electrons and positrons and also returns to step 218 for each isotope. Step 224 for each particle type material and energy group identified at step 222, calculates the mean free path, expected energy deposition, and, if photon and electron transport are on, the mean free path for Woodcock tracking. At step 226 a check is made for heavy charged particles and if none exist the routine continues with step 236. If charged particles do exist, the stopping power is calculated at step 230 for each isotope identified at step 228. At step 234 collision probability and range arrays are set up for each material identified at step 232. Step 236 sets up parameters and arrays for multiple scattering and energy straggling of charged particles (both heavy and light). The program returns to the calling routine (Generator 20) at step 238.

Figure 15A:
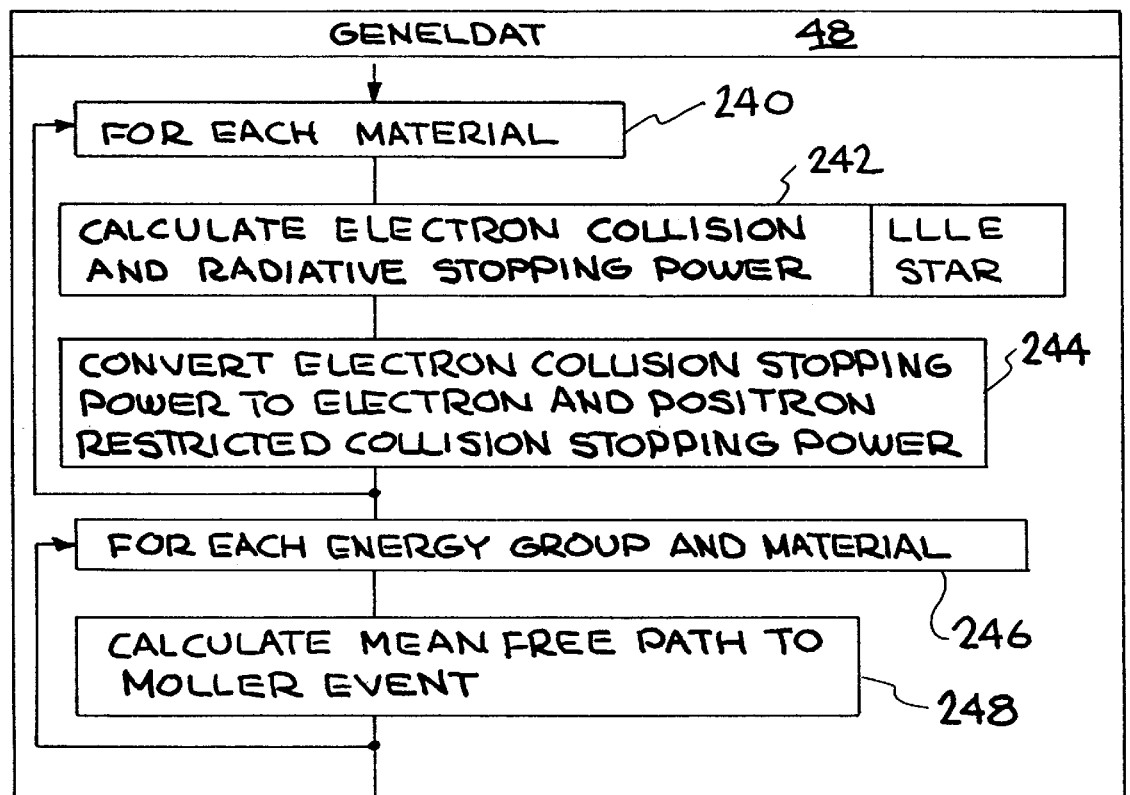
Figure 15B:
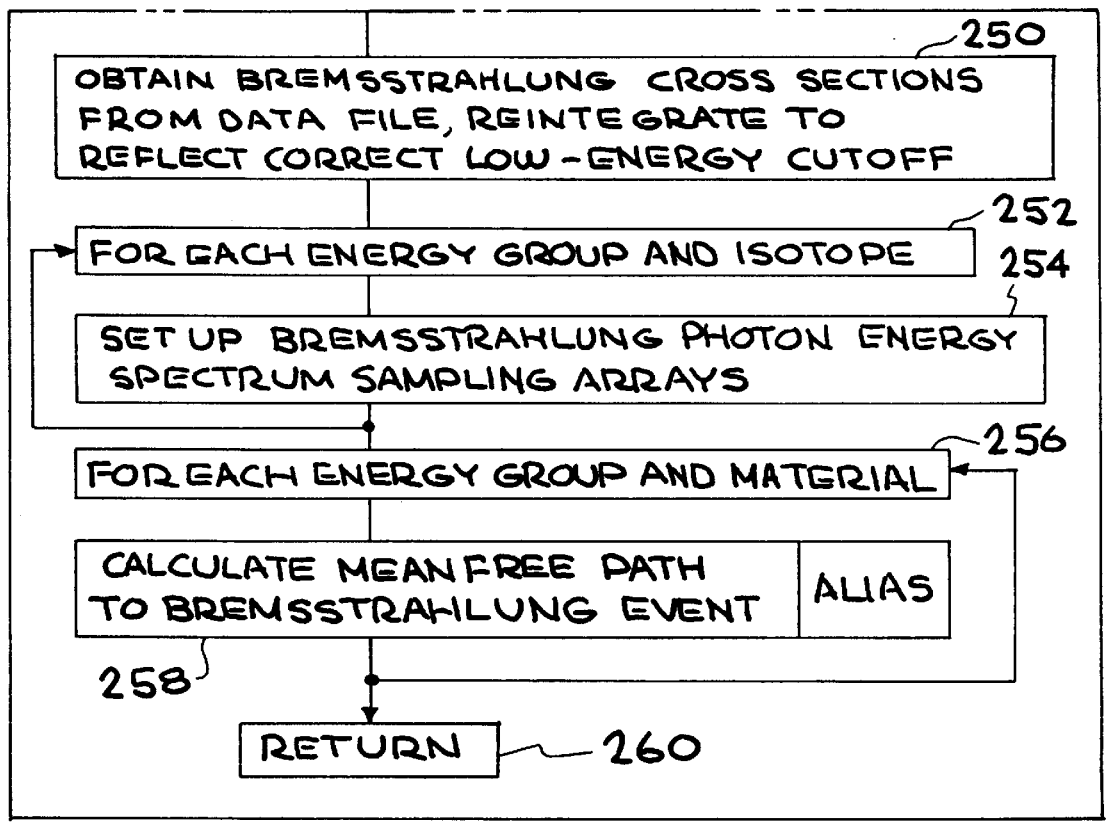

Referring now to FIG. 15, the subroutine GENELDAT (48) calculates the electron collision and radiative stopping power (step 242), converts (step 244) the electron collision stopping power to electron and positron restricted collision stopping power, for each identified material (step 240). Step 248 calculates the mean free path to Moller event at step 246 for each energy group and material. Step 250 obtains bremsstrahlung cross sections from the data file, and reintegrates them to reflect the correct the low-energy cutoff. Step 254 sets up bremsstrahlung photon energy spectrum sampling arrays for each energy group isotope identified at step 252. Step 258 calculates the mean free path to bremsstrahlung event for each energy group and material identified at step 256 and then returns to the calling routine at step 260.

At this point the generator phase of the process (Generator 20) is complete. Now the transport physics process (All Particle Tracker 22) is to be described.

Figure 16B:
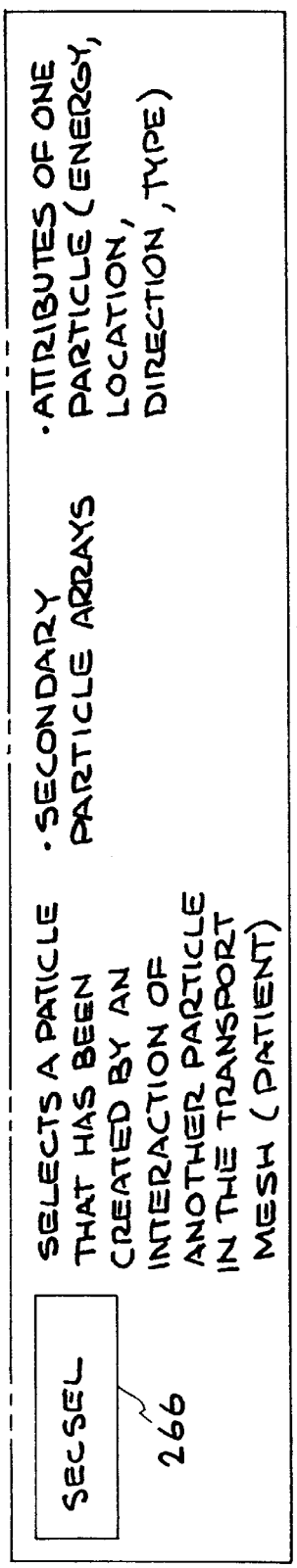

FIGS. 16 through 19 describe the subroutines that make up the All-Particle Tracker 22 (MCXEC). Referring now to FIG. 16, BEAMSEL (262) selects particle attributes for a primary particle arising from an external radiation beam. The input to this routine comprises (i) radiation source angular and energy distributions for external sources, (ii) arrays describing beam delivery components, (iii) material data (internal material lists, isotope data, etc.), (iv) nuclear and atomic transport data arrays and (v) number and energy group structure for each particle type. The output from this routine provides attributes of one particle (energy, location, direction, type). The subroutine BRACHYSEL (264) selects particle attributes for a primary particle arising from an internal (brachytherapy) radiation source. The input to this subroutine is radiation source angular and energy distributions for internal sources. The subroutine output provides attributes of one particle (energy, location, direction, type). The subroutine SECSEL (266) selects a particle that has been previously created and stored by an interaction of another particle in the transport calculation, from an input of secondary particle arrays to provide an output of the attributes of one particle.

Figure 17A:
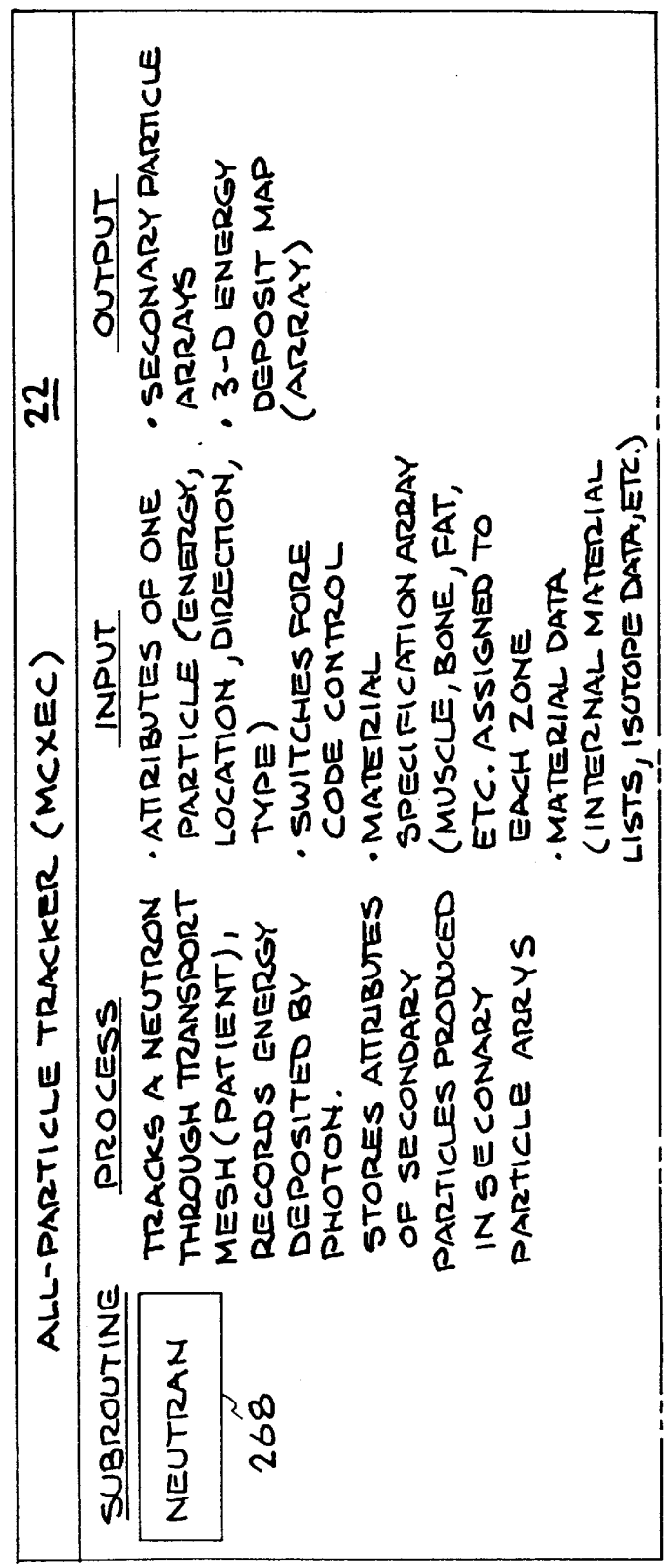

Referring to FIG. 17, NEUTRAN (268) tracks a neutron through a mesh (patient), and records the energy deposited by the neutron and stores the attributes of secondary particles produced in secondary particle arrays. The input to this routine comprises (i) attributes of one particle, (ii) switches for code control, (iii) material specification array, (iv) material data, (v) nuclear transport data arrays and (vi) number and energy group structure for neutrons. The output of NEUTRAN (268) is secondary particle arrays and a 3-D energy deposit map (array). PHOTRAN (270) tracks the photon through the transport mesh and records the energy deposited by the photon. It also stores the attributes of secondary particles produced in secondary particle arrays. The input to PHOTRAN (270) comprises (i) the attributes of one particle, (ii) switches for code control, (iii) material specification array, (iv) material data, (v) atomic transport data arrays and (vi) number and energy group structure for photons. Secondary particle arrays and 3-D energy deposit map are output from PHOTRAN (270).

Referring to FIG. 18, CPTRAN (272) tracks a heavy charged particle through the patient transport mesh and records energy deposited by the heavy charged particle. CPTRAN (272) also stores attributes of secondary particles produced in secondary particle arrays. The input to CPTRAN (272) comprises (i) switches for code control, (ii) a material specification array, (iii) material data, (iv) nuclear transport data arrays, (v) heavy charged particle transport data arrays, and (vi) the number and energy group structure for heavy charged particles. The output from this subroutine is secondary particle arrays and a 3-D energy deposit map (array). ELTRAN (274) tracks a primary electron through the patient transport mesh, records energy deposited recorded by the electron and stores the attributes of secondary particles produced in secondary particle arrays. A primary electron is defined as an electron originating in a radiation source (created by BEAMSEL or BRAYCHYSEL). The input to ELTRAN (274) consists of (i) attributes of one particle which is energy, location, direction, type, (ii) switches for code control, (iii) material specification arrays, (iv) material data, (v) electron transport data arrays, and (vi) number and energy group structure for electrons. ELTRAN (274) outputs secondary particle arrays and a 3-D energy deposit map (array). ELTRANI (276) tracks a secondary electron through the transport mesh of the patient, records energy deposited by the electron and stores attributes of secondary particles produced in secondary particle arrays. The input to ELTRANI (276) is (i) attributes of one particle, (ii) switches for code control, (iii) a material specification array, (iv) material data, (v) electron transport data array, and (vi) number and energy group structure for electrons. ELTRANI (276) outputs secondary particle arrays and a 3-D energy deposit map (array).

Referring to FIG. 19, UPDATE (278) adds a 3-D energy deposit map calculated over batch to a 3-D energy deposit map for the problem. The input to this subroutine is a 3-D energy deposit map calculated for a single batch. The output of this subroutine is an integral 3-D energy deposit map (array). STDDEV (280) updates arrays necessary for a standard deviation calculation with energy deposit information determined from each batch. The input is a 3-D energy deposit map and standard deviation zone ID array. The output from STDDEV (280) is standard deviation precalculation arrays. STDDEVX (282) calculates the standard deviation from standard deviation precalculation arrays to produce standard deviation arrays.

Figure 20:
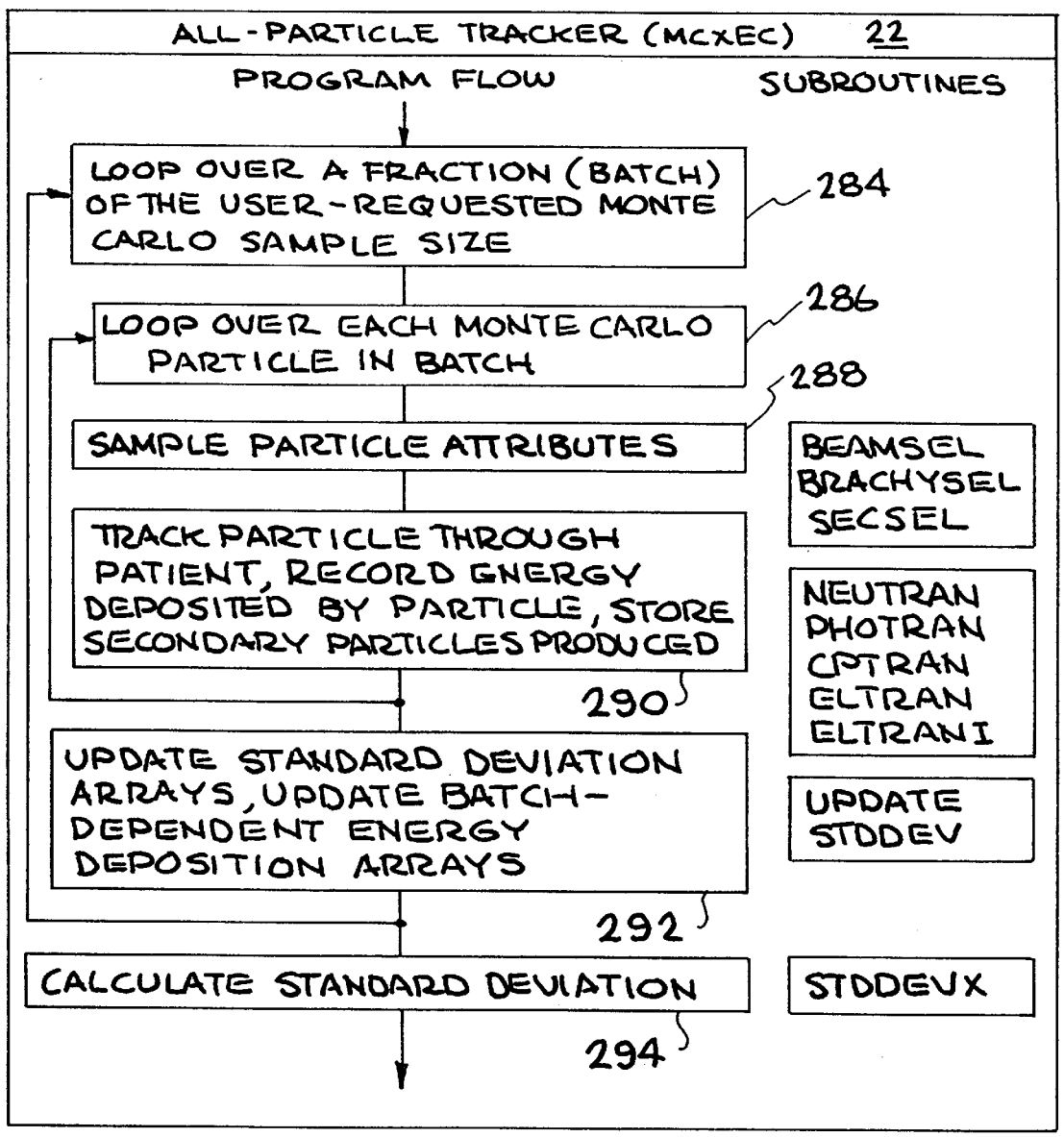
FIG. 20 shows the program flow of the All-Particle Tracker 22.

FIG. 20 shows the program flow of the All-Particle Tracker 22. Step 288 samples particle attributes and step 290 tracks the particle through the patient, records the energy deposited by the particle, and stores the secondary particle produced. Step 286 loops over each Monte Carlo particle in the batch. Step 292 updates the standard deviation arrays and batch-dependent energy deposit arrays before looping back to step 284 to continue the next batch of Monte Carlo particles. When all batches are complete the standard deviation is calculated at step 294.

Figure 21A:
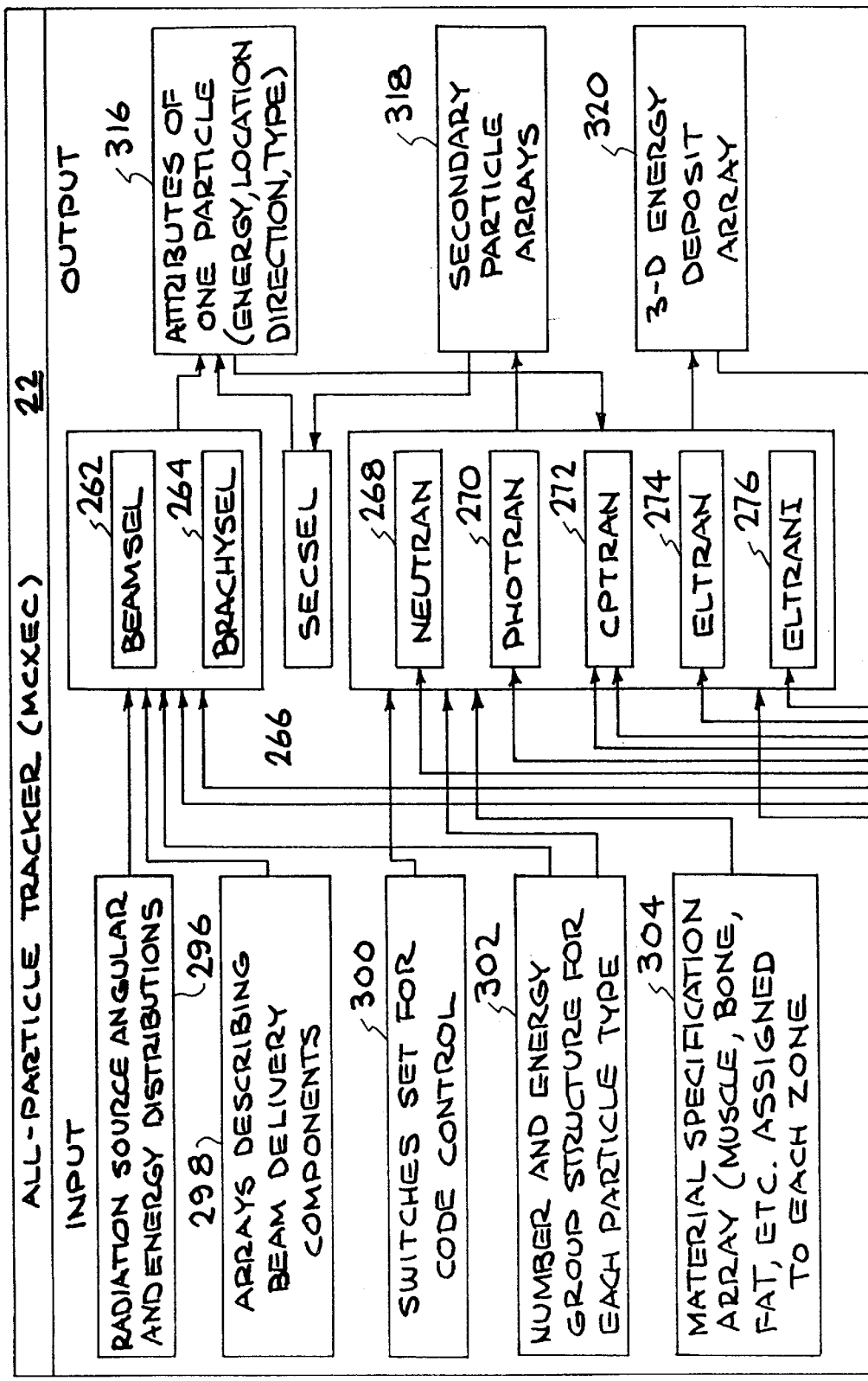
FIG. 21 shows another view of the overall flow, data input, output and subroutine functions of the All-Particle Tracker 22.
Figure 21B:
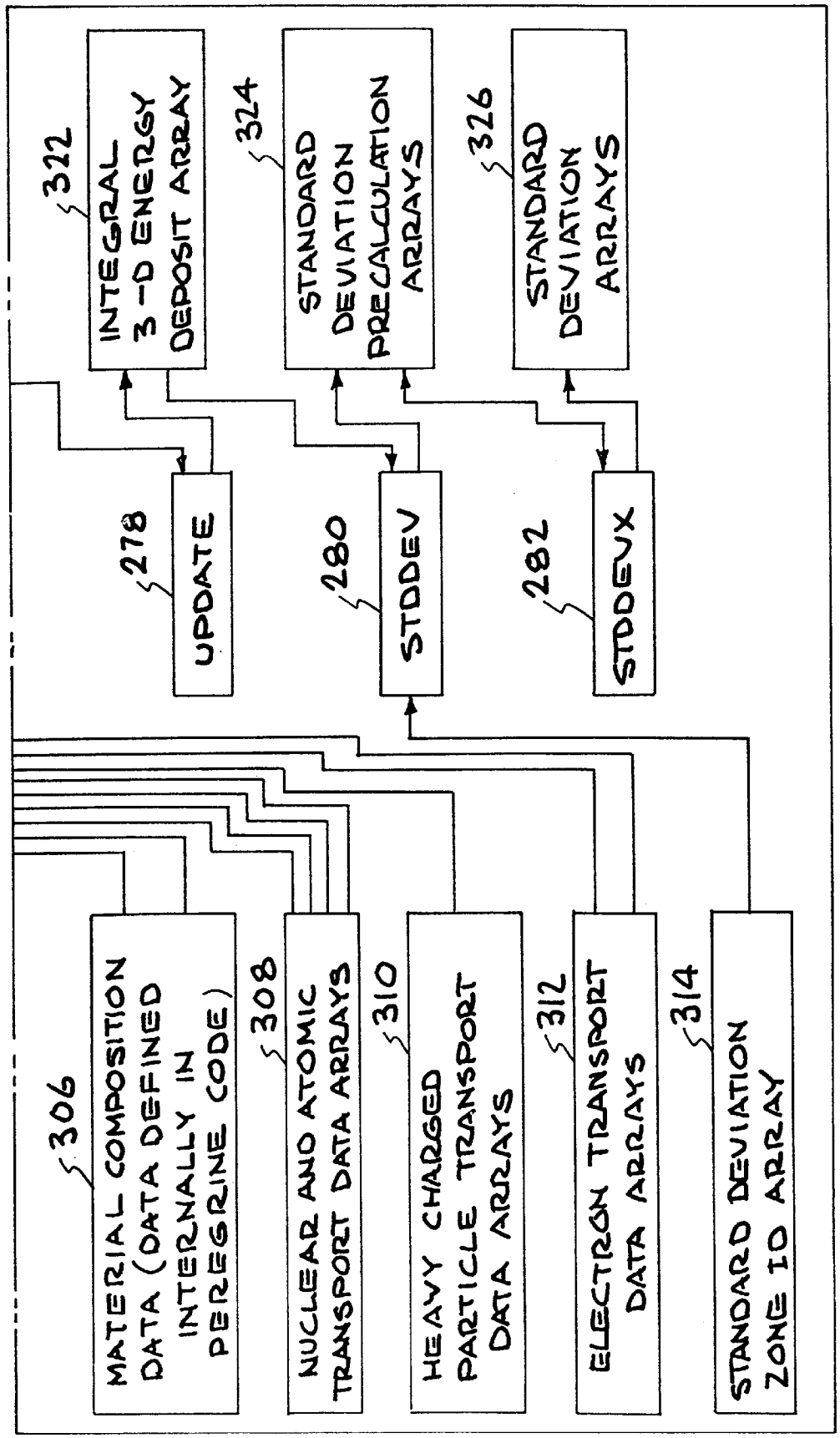

Still another view of the flow, data input, output and subroutine functions are shown in FIG. 21. The inputs for the subroutines that make up the All-Particle Tracker are shown at 296, 298, 300, 302, 304, 306, 308, 310, 312 and 314 and comprise respectively radiation source angular and energy distributions, arrays describing beam delivery components, setting switches for code control, number and energy group structure for each particle type, material specification array, material composition data, nuclear and atomic transport data arrays, heavy charged particle transport data arrays, electron transport data arrays and a standard deviation zone ID array. Output 316 provides attributes of one particle. Secondary particle arrays are provided by output 318. Output 320 shows the 3-D energy deposit array and 322 comprises the integral 3-D energy deposit array. Output 324 is a standard deviation precalculation array. Output 326 provides the standard deviation arrays. FIGS. 16 through 19 describe (supra) the subroutines that make up the All-Particle Tracker (MCXEC (22)).

Figure 22A:
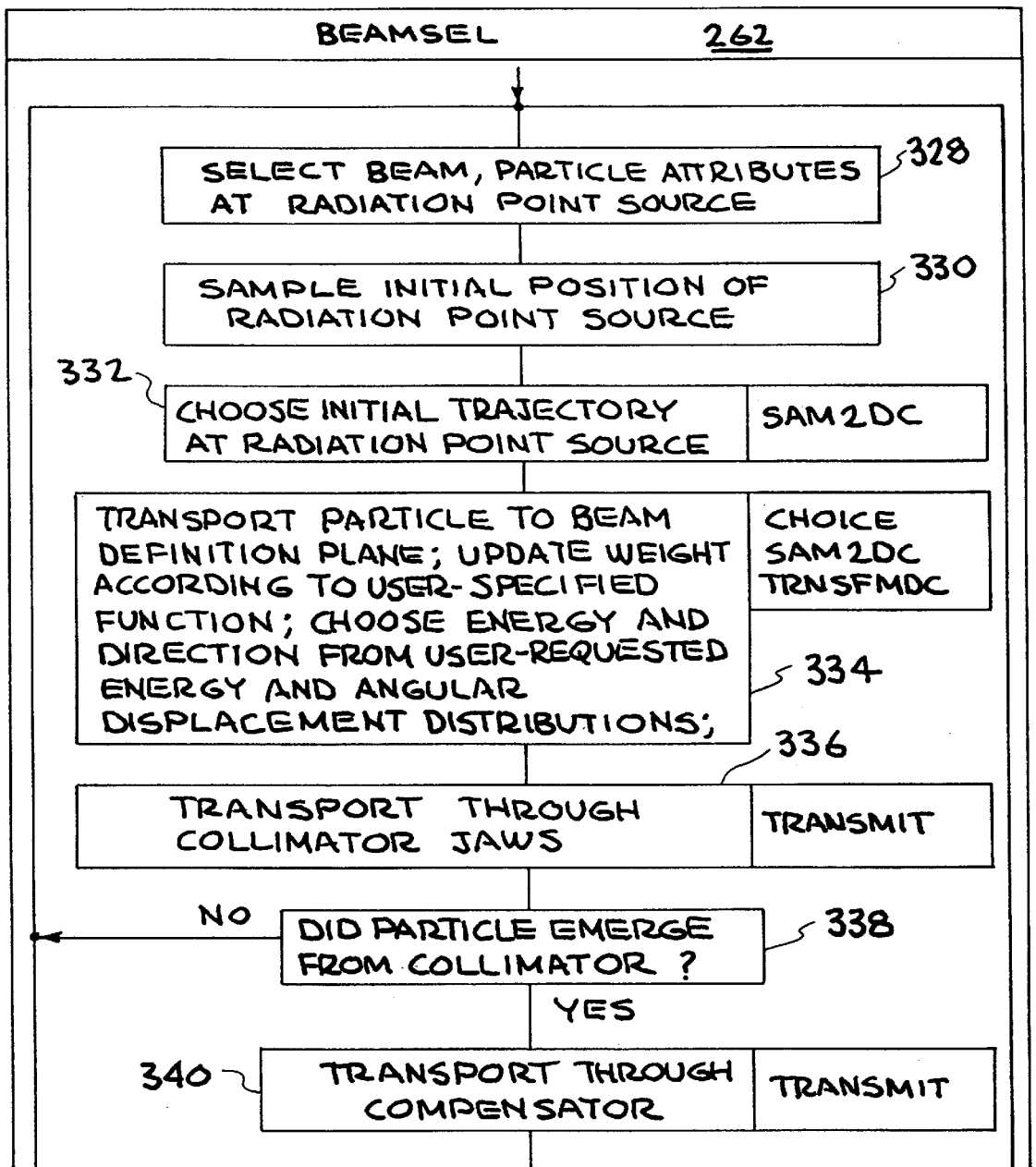
Figure 22B:
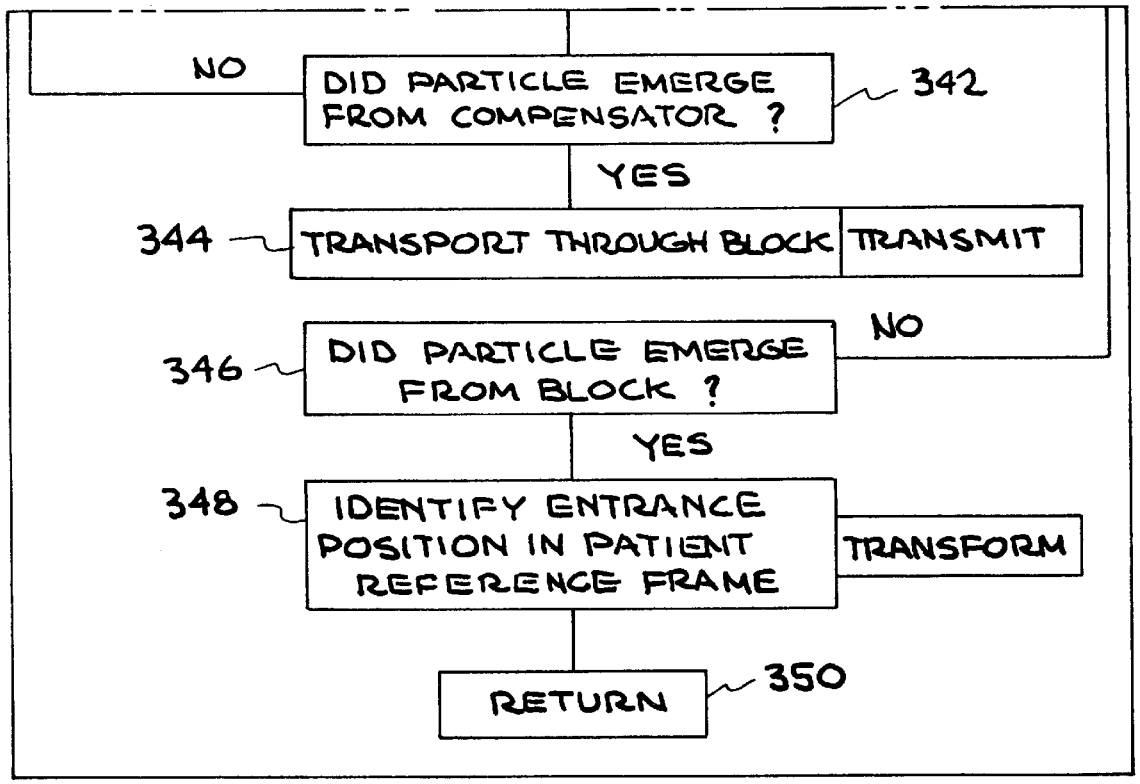

Detailed views of the program flow of each subroutine of the All-Particle Tracker 22 are shown in FIGS. 22 through 31. Referring now to FIG. 22, a flow diagram of BEAMSEL (262), step 328 selects the beam and particle attributes at the radiation point source. The initial position point source is sampled at step 330. The initial trajectory at the radiation point source is chosen at step 332. Step 334 performs the following functions: (i) transport the particle to the beam definition plane, (ii) update the weight according to user-specified function and (iii) choose energy and direction from user-requested energy and angular displacement distributions. Step 336 transport a particle through the collimator jaws. Step 338 questions whether the particle emerged from the collimator, and if it did not, then the program flow returns to step 328, but if it did, step 340 determines the transport through the compensator. Step 342 questions whether the particle emerged from the compensator and if it did not, the program flow returns again to step 328, but if it did, then a particle is transported through the block at step 334. Step 346 questions whether the particle emerged from the block and if it did not, the program flow returns to step 328, but if it did, step 348 identifies the entrance position in the patient reference frame and step 350 returns to the calling routine (All-Particle Tracker 22).

Figure 23:
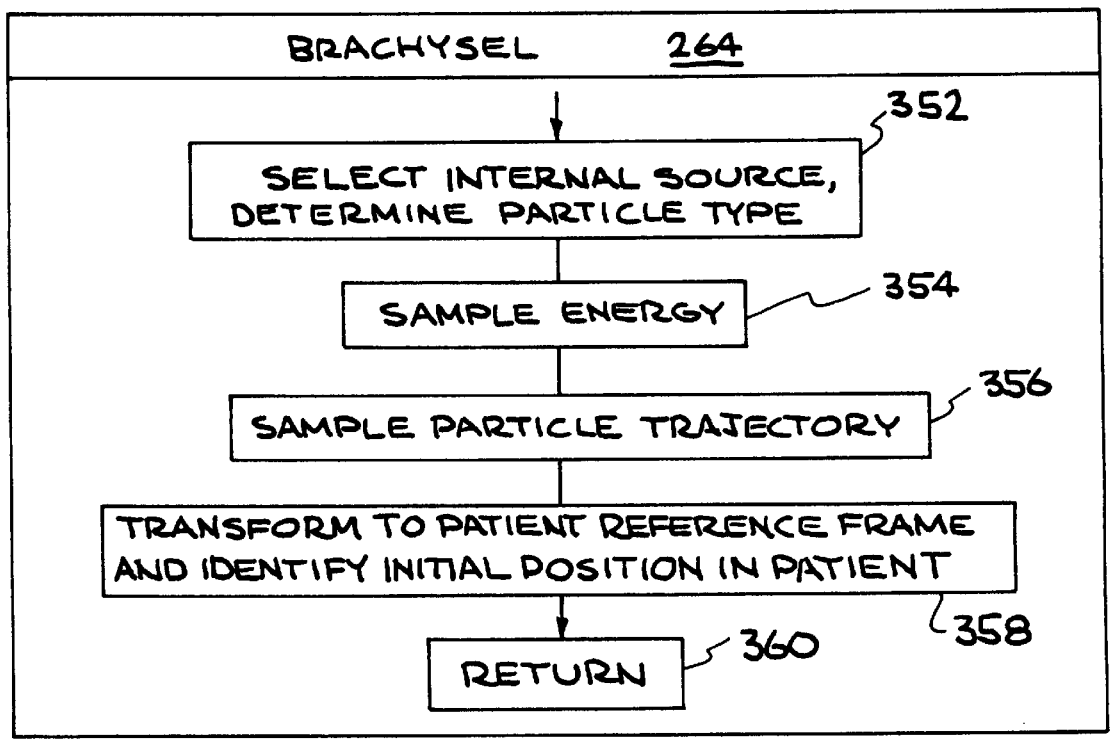

FIG. 23 shows the program flow for BRACHYSEL 264 and begins with step 352 to select the internal source and determine the particle type. Step 354 samples the energy and step 356 samples the particle trajectory. The patient reference frame is transformed and the initial position is identified in the patient at step 358. The program flow returns to the calling routine at step 360.

Figure 24:
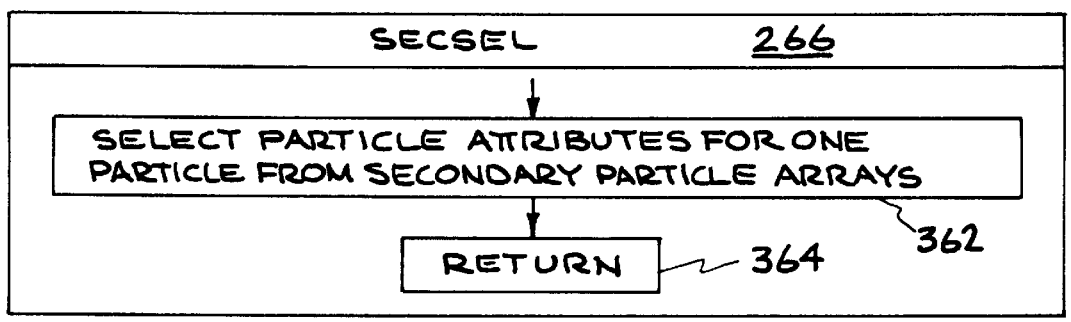
FIGS. 22 through 31 show detailed views of the program flow of each subroutine of the All-Particle Tracker 22.

Subroutine SECSEL 266 is shown in FIG. 24 with step 362 selecting the particle attributes for one particle from secondary particle arrays and returning to the calling routine at step 364.

Figure 25A:
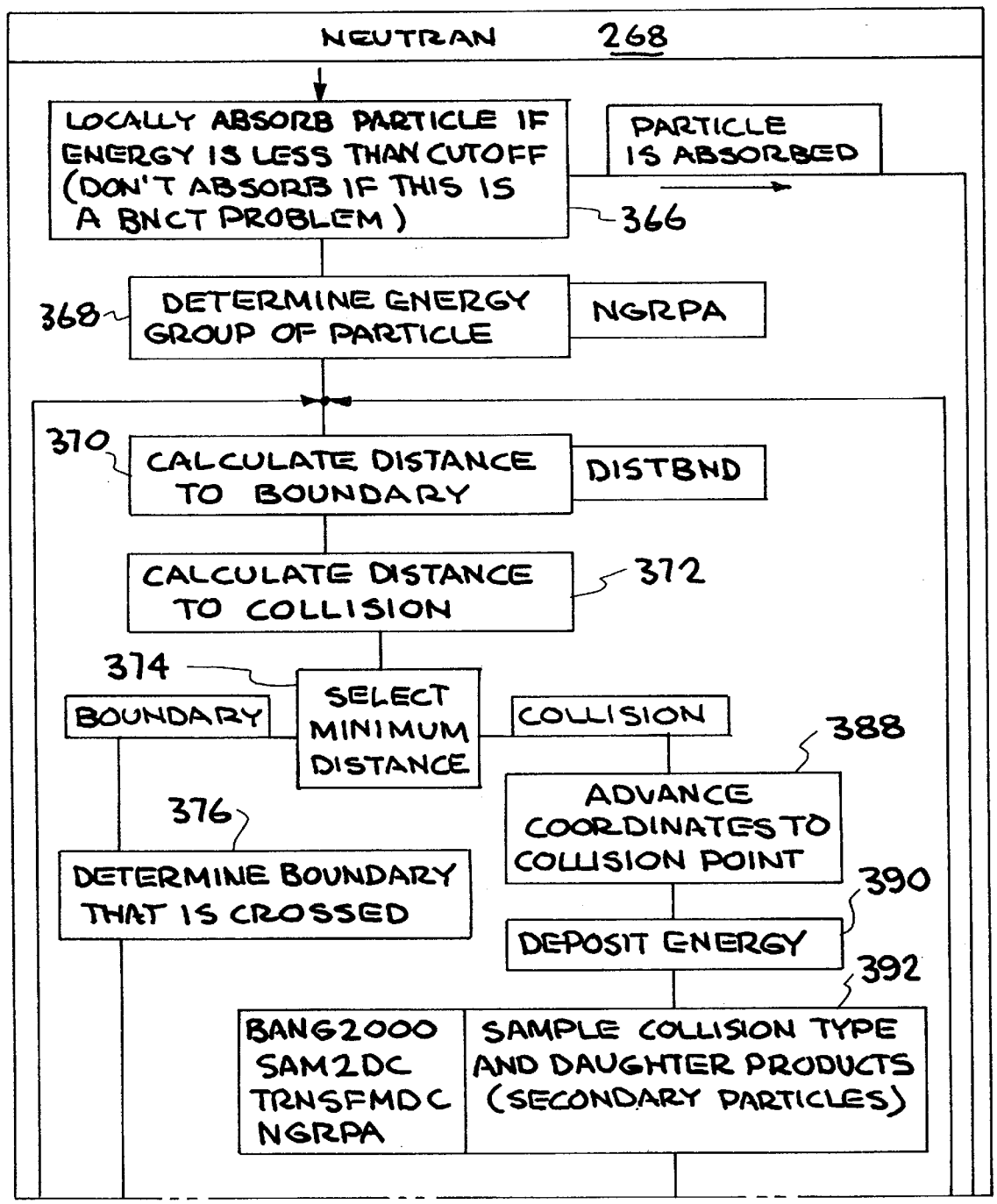
Figure 25B:
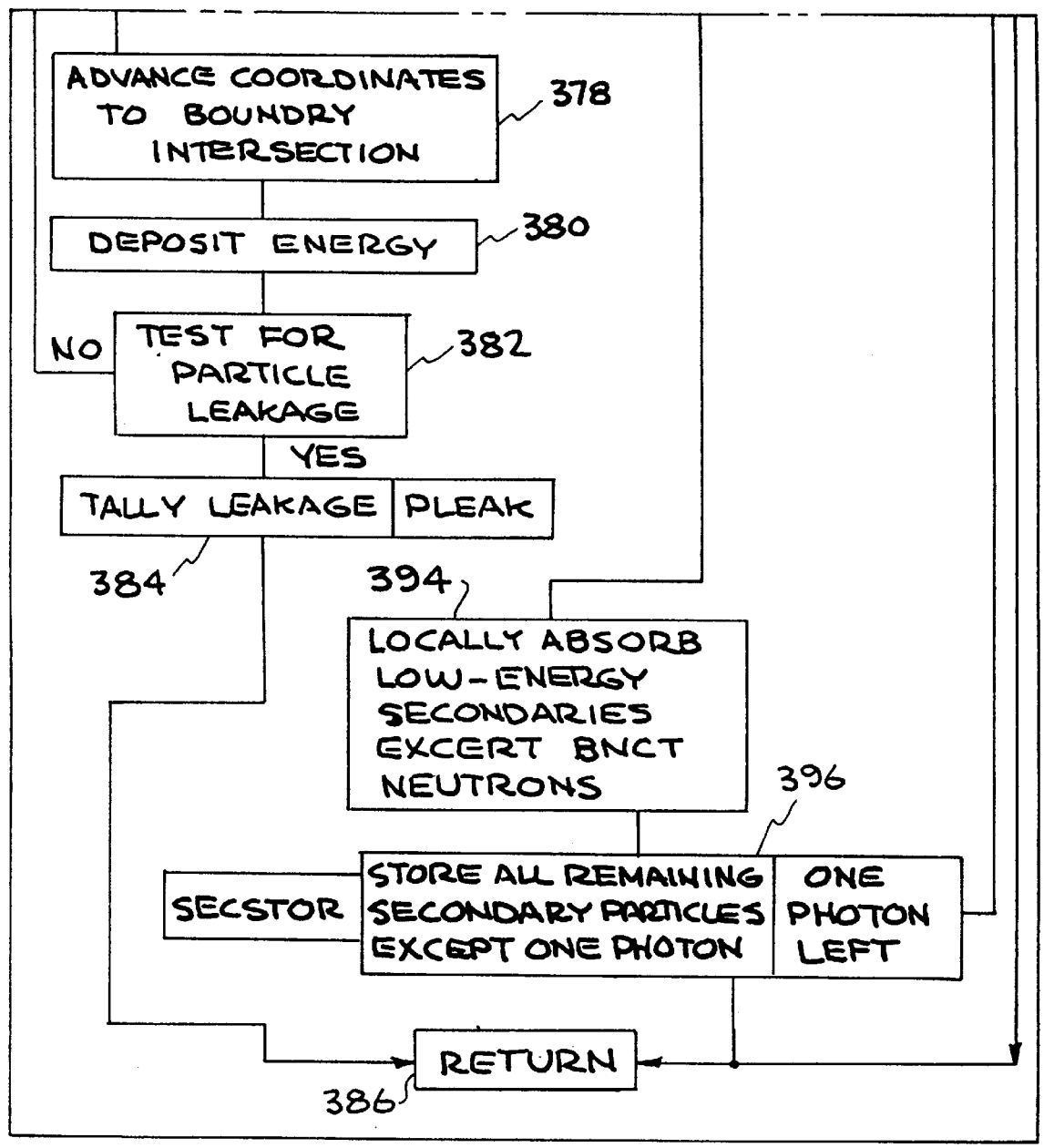

Referring to FIG. 25, the subroutine NEUTRAN (268) begins with step 366 to locally absorb a particle if its energy is less than a cutoff energy and not absorb the particle if this is a BNCT calculation. If the particle is absorbed, the program flow moves to step 386, and returns to the calling routine. If the particle is not absorbed, step 368 determines the energy group of the particle and step 370 calculates the distance to the boundary. Step 372 calculates the distance to collision and step 374 selects the minimum distance of the boundary and the collision. If the minimum distance was a boundary step 376 determines the boundary that is crossed and step 378 advances the coordinates to the boundary intersection. Energy deposited is determined at step 380 and particle leakage is then tested at step 382. If there is no particle leakage, then the program flow returns to step 370. If step 374 has selected the minimum distance as a collision, step 388 advances the coordinates to the collision point and the energy deposited is determined at step 390. Step 392 samples the collision type and daughter products (secondary particles). Step 394 locally absorbs low-energy secondaries except BNCT neutrons. Step 396 stores all remaining secondary particles except one neutron before returning to the calling routine at 386.

Figure 26A:
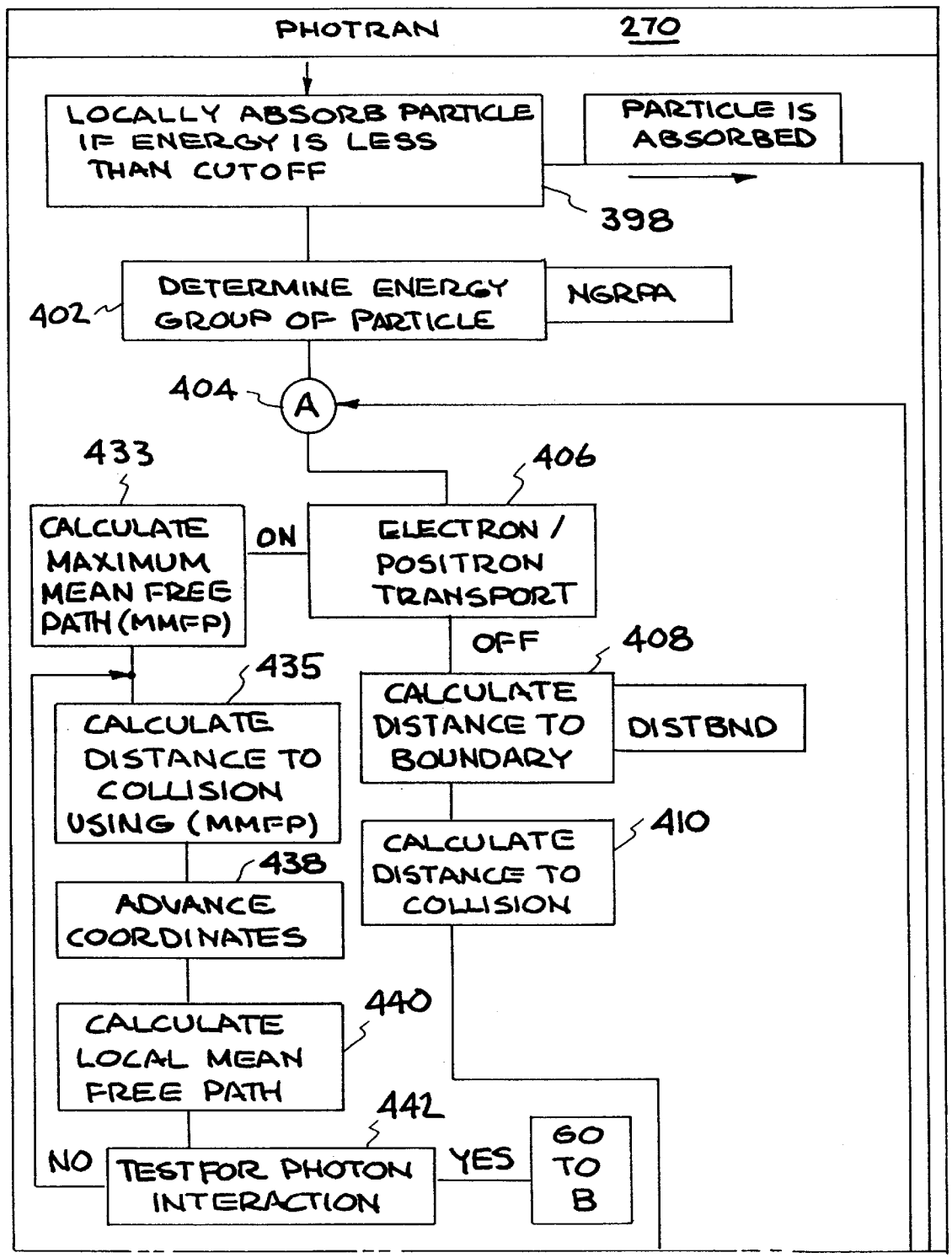
Figure 26B:
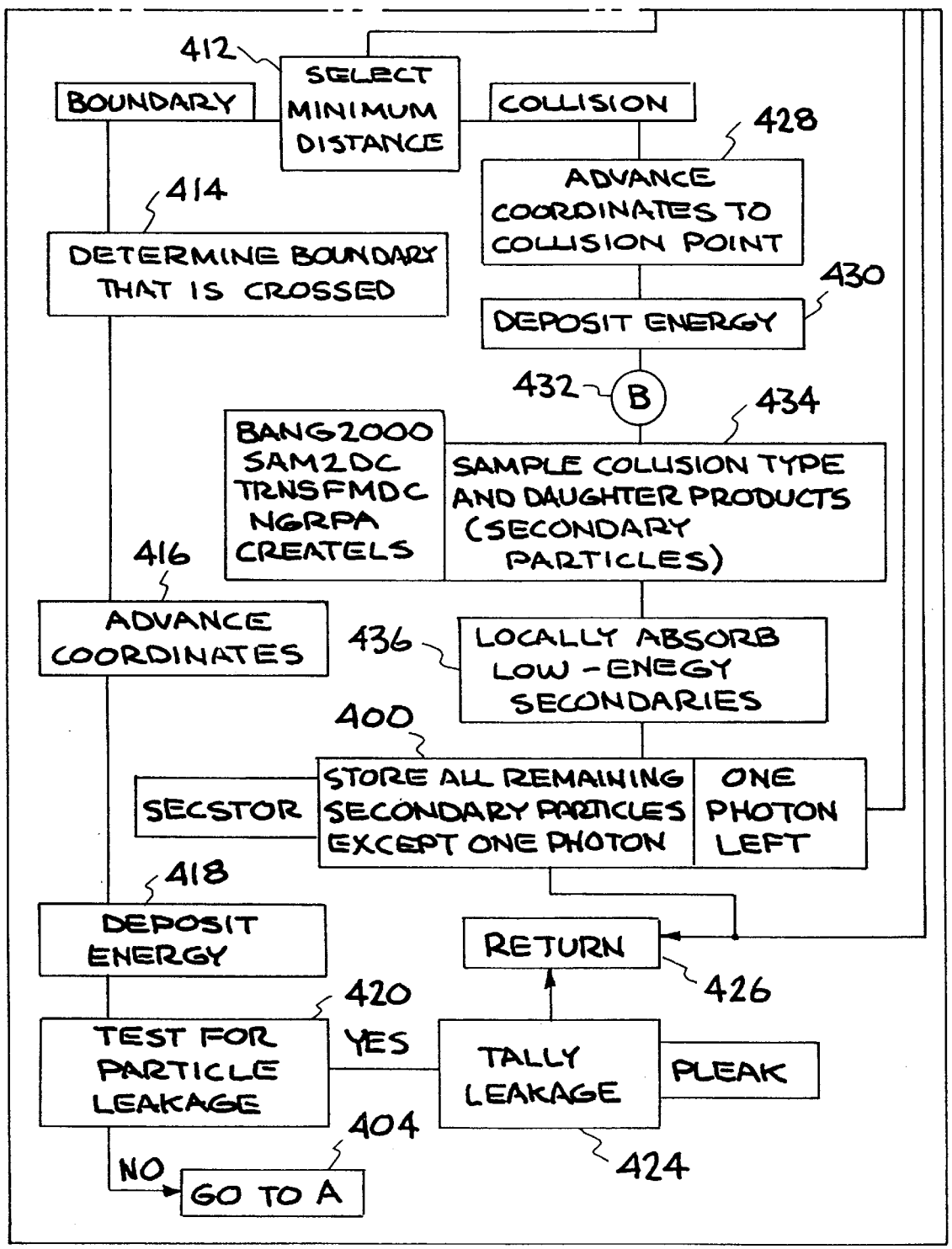

Referring to FIG. 26, the subroutine PHOTRAN (270) begins with step 398 which locally absorbs a particle if the energy of that particle is less than the cutoff. If the particle is absorbed, this routine returns to the calling routine at step 426. If the particle is not absorbed at step 398, step 402 determines the energy group of the particle and moves through step A at step 404 to begin at step 406 to test if electron/positron transport is needed. If the transport is off, then step 408 calculates the distance to boundary and the distance to the collision is determined at step 410. Step 412 selects the minimum distance of the boundary and the collision. If the minimum distance was a boundary then step 414 determines the boundary that is crossed. The coordinates are advanced in step 416. Energy is deposited in step 418. The particle is tested for leakage at step 420. If there is no leakage, the program flow returns to step 404, but if there is particle leakage, the leakage is tallied at step 424 before returning to the calling routine at step 426. If the minimum distance was a collision then step 428 advances coordinates to the collision distance. Step 430 deposits energy. Collision type and daughter products (secondary particles) are sampled at step 434. Low energy secondaries are locally absorbed at step 436 and all remaining secondary particles except photons are stored at step 400. If the electron/positron transport is determined to be on at 406, step 433 calculates the maximum mean free path. The distance to collision is calculated at step 435 using the problem maximum mean free path. Coordinates are advanced at step 438 and the local mean free path is calculated at step 440. Photon interaction tests occur at step 442 and if no photon interaction has occurred, the program flow returns to step 436, and if photon interaction has occurred, the program flow moves to step 432, which has been described above and leads to the calling routine at step 426.

Figure 27A:
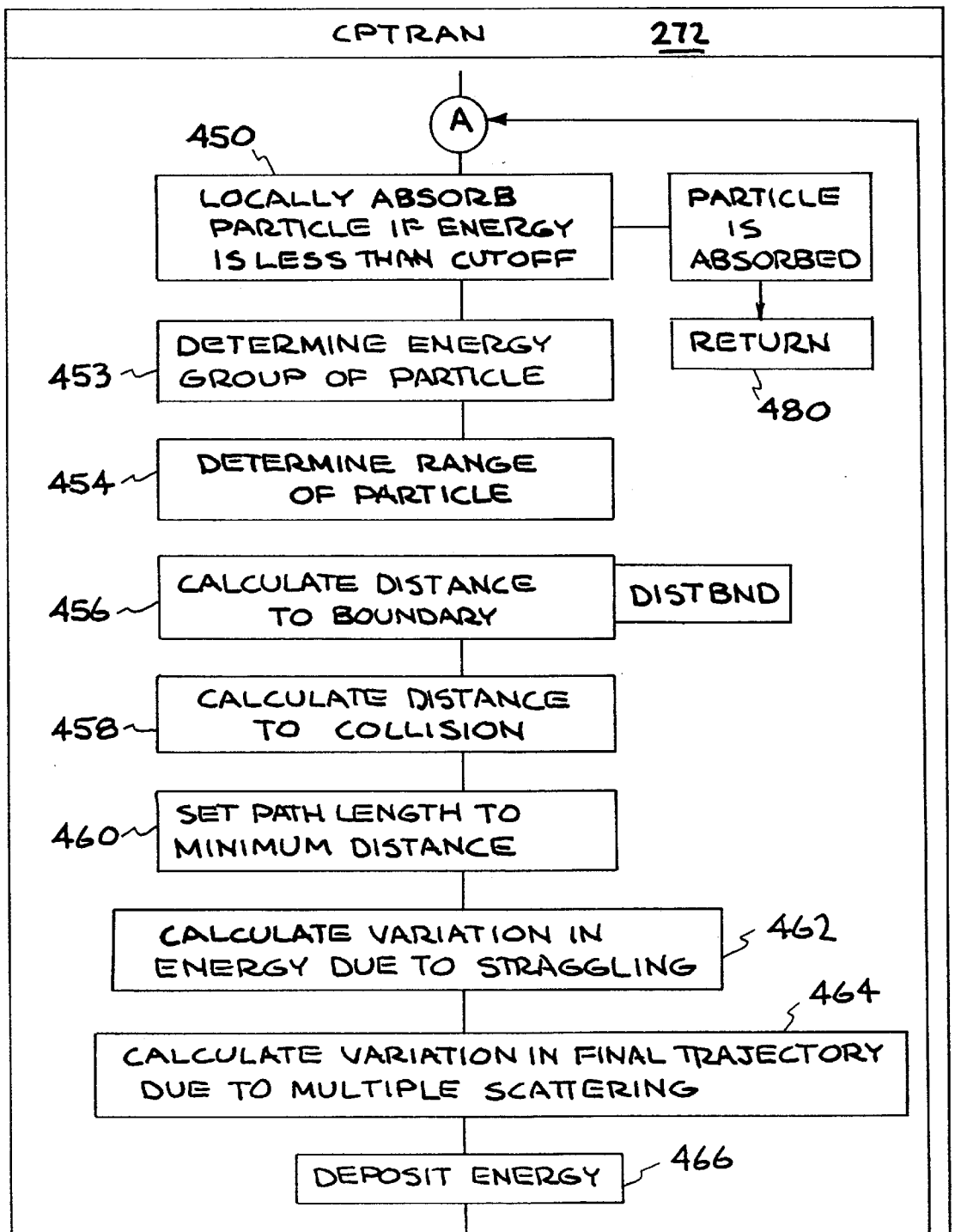
Figure 27B:
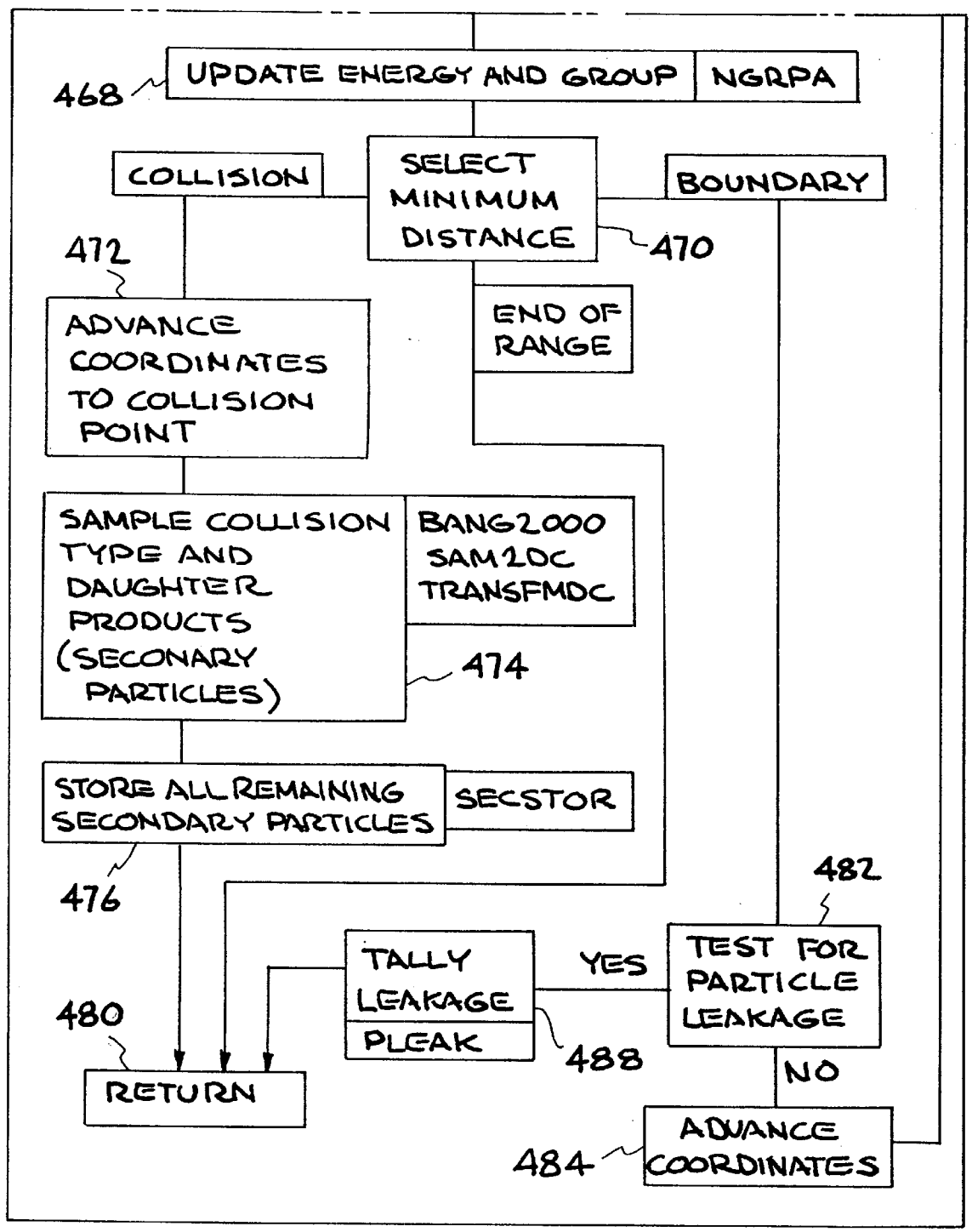

Referring to FIG. 27, CPTRAN (272) begins with step 450 where a particle is locally absorbed if its energy is less than the cutoff energy, and if the particle is absorbed, the program flow returns to the calling routine at step 480. If the particle is not absorbed, at steps 453, 454, 456, and 458 respectively, the program determines the energy group of the particle, determines the range of the particle, calculates the distance to the boundary and calculates the distance to collision. Step 460 sets minimum pathlength to minimum distance. Next, the variation in energy due to straggling is calculated at step 462. The variation in final trajectory due to multiple scattering is then calculated at step 464, and the energy deposit is made at step 466. Step 468 updates the energy and the group and step 470 selects the minimum distance of the collision and the boundary. At step 470 if the minimum distance is the collision then step 472 advances the coordinates and 474 samples the collision type and daughter products. All remaining secondary particles are stored at 476 and the program flow returns to the calling routine at step 480. At step 470 if the minimum distance was the boundary then step 482 tests for particle leakage and if there is none, advances the coordinates at step 484 and returns to step 486. If particle leakage has occurred, step 488 tallies the leakage and the program flow returns to the calling routine at step 480.

Figure 28A:
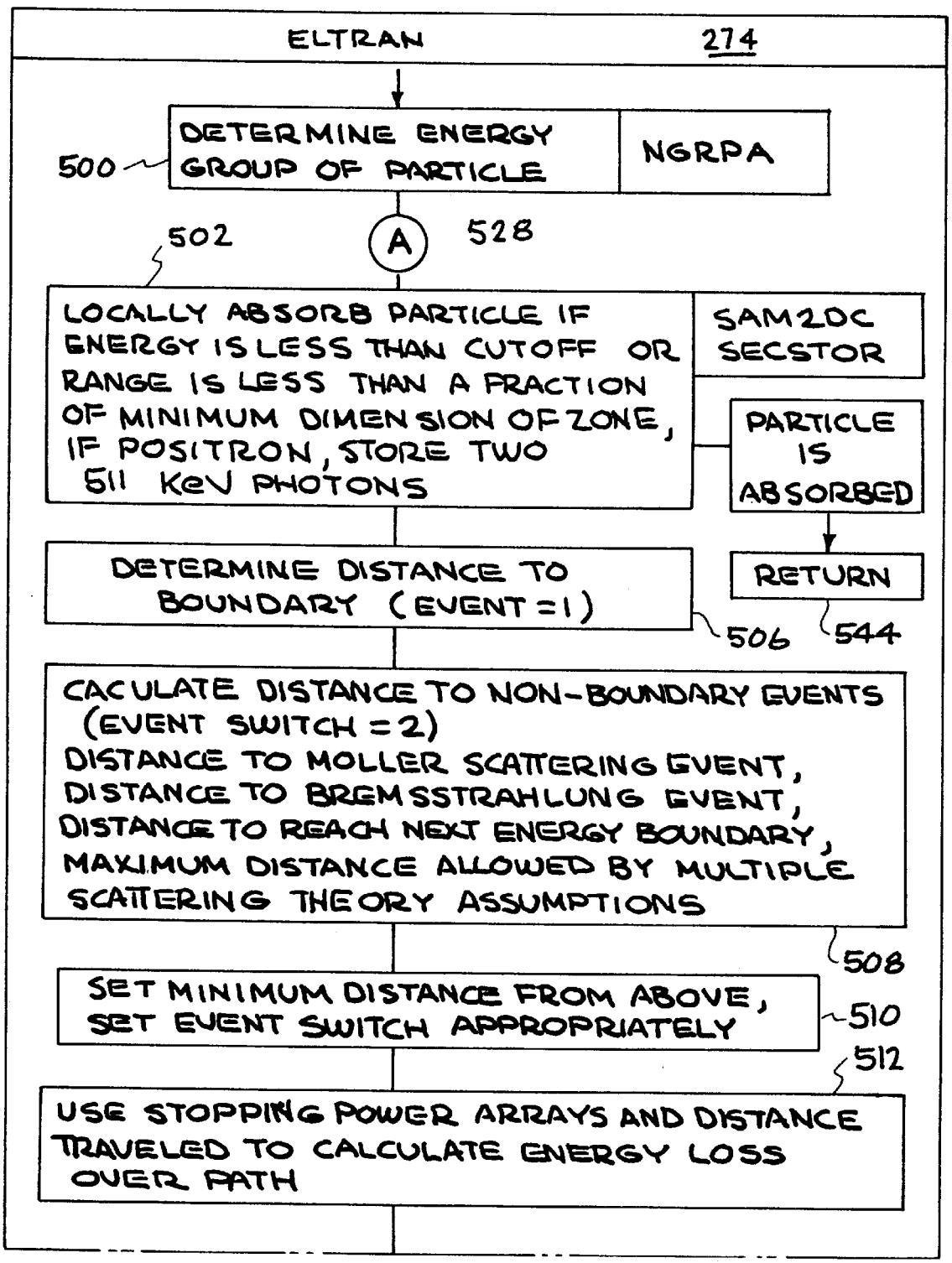

ELTRAN (274), shown in FIG. 28A, begins with step 500 which determines the energy group of a particle. Step 502 locally absorbs the particle if its energy is less than the cutoff energy or its range is less than a fraction of the minimum dimension of the zone. If the particle is a positron, two 511 keV photons are stored. If the particle is absorbed, the program flow returns to the calling routine at 544. Otherwise, the distance to boundary is determined at step 506 (event=1). Step 508 calculates the distance to a Moller scattering event, distance to bremsstrahlung event, distance to reach the next lowest energy boundary, and the maximum distance allowed by multiple scattering theory assumptions (all of these non-boundary crossing events: event=2). Step 510 sets the distance traveled to the minimum distance and sets the event switch. Step 512 uses stopping power arrays and the distance traveled to calculate the energy loss over the path. Step 514 calculates the variation in final trajectory due to multiple scattering. Step 516 is the energy deposit calculation. The energy of the particle is updated at step 518, and the event switch at 520 determines if the event is equal to two where there is no boundary crossing or if the event is equal to one where there is a boundary crossing. If the event switch equals two, step 522 corrects for the path curvature and advances coordinates. A Moller scattering event is then tested for in step 524 and if their is none, a bremsstrahlung event is tested for at 526. If the event test answer is no, then the program flow goes to A at step 528, and if the bremsstrahlung event answer is yes at step 526, then a photon is stored and electron tracking will continue in step 534. Step 536 determines the energy group of the electron before returning to A at step 528. If the answer is yes when the Moller scattering event is tested at 524, step 530 stores a lower-energy electron and the routine continues tracking the higher-energy electron. The energy group of the electron is determined at step 532 before returning to A at step 528. When the event equals one at the event switch 520, particle leakage is tested at step 538. If particle leakage did not occur, coordinates are advanced at step 540 and the program flow goes to A at step 528. If particle leakage has occurred as determined at step 538, the leakage is tallied at step 542 and the program flow returns to the calling routine at step 544.

Figure 28B:
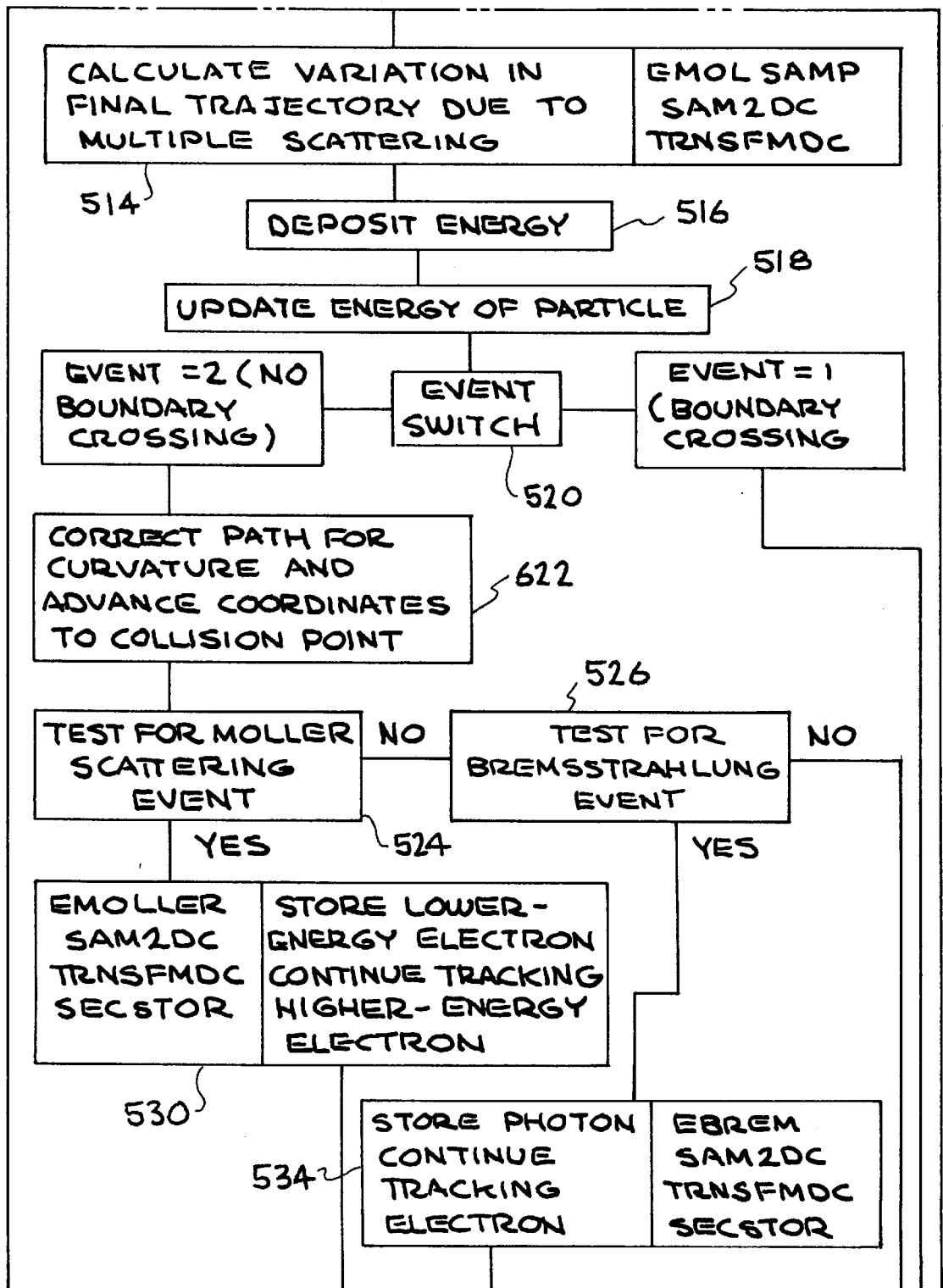
Figure 28C:
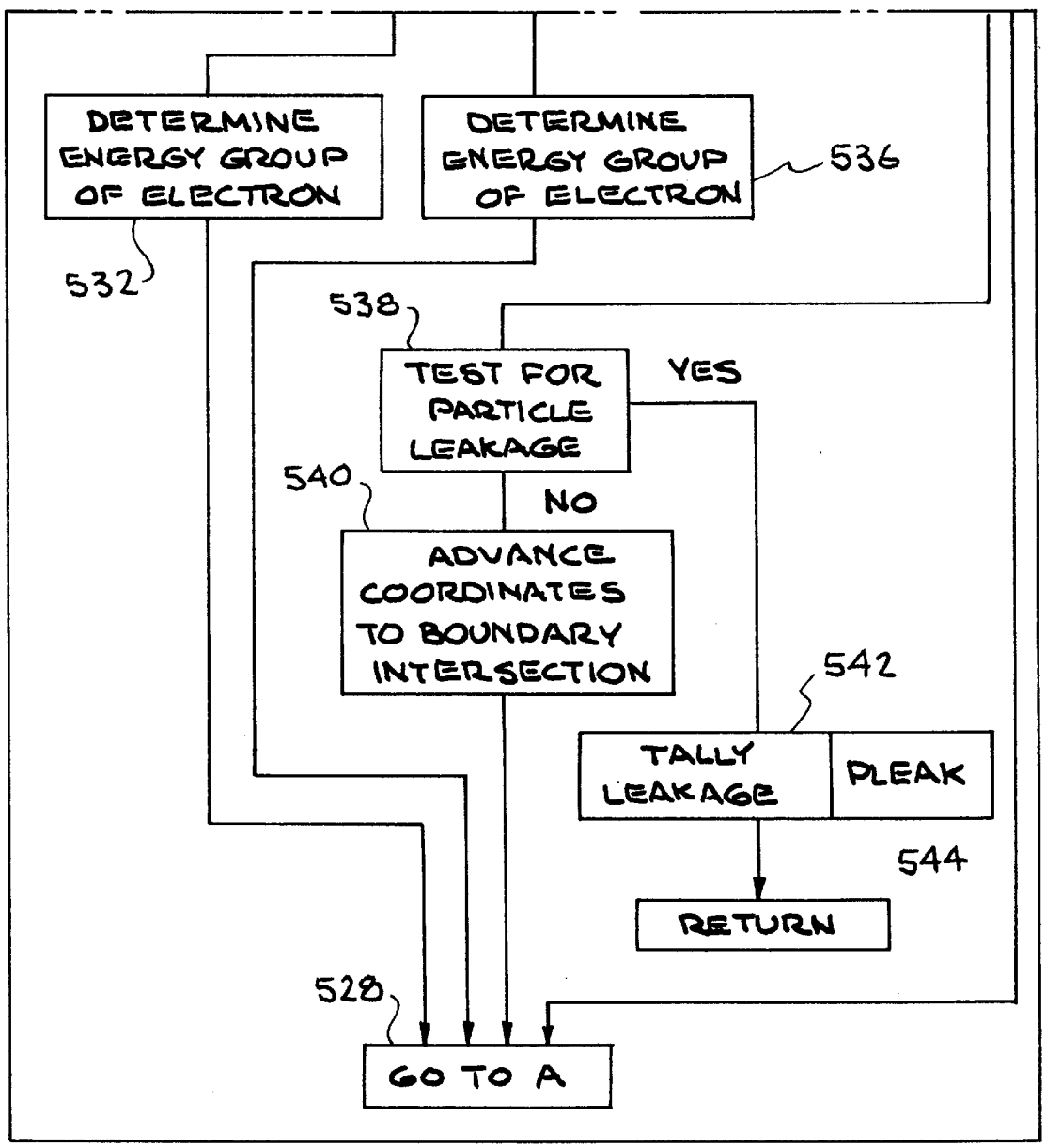
Figure 28D:
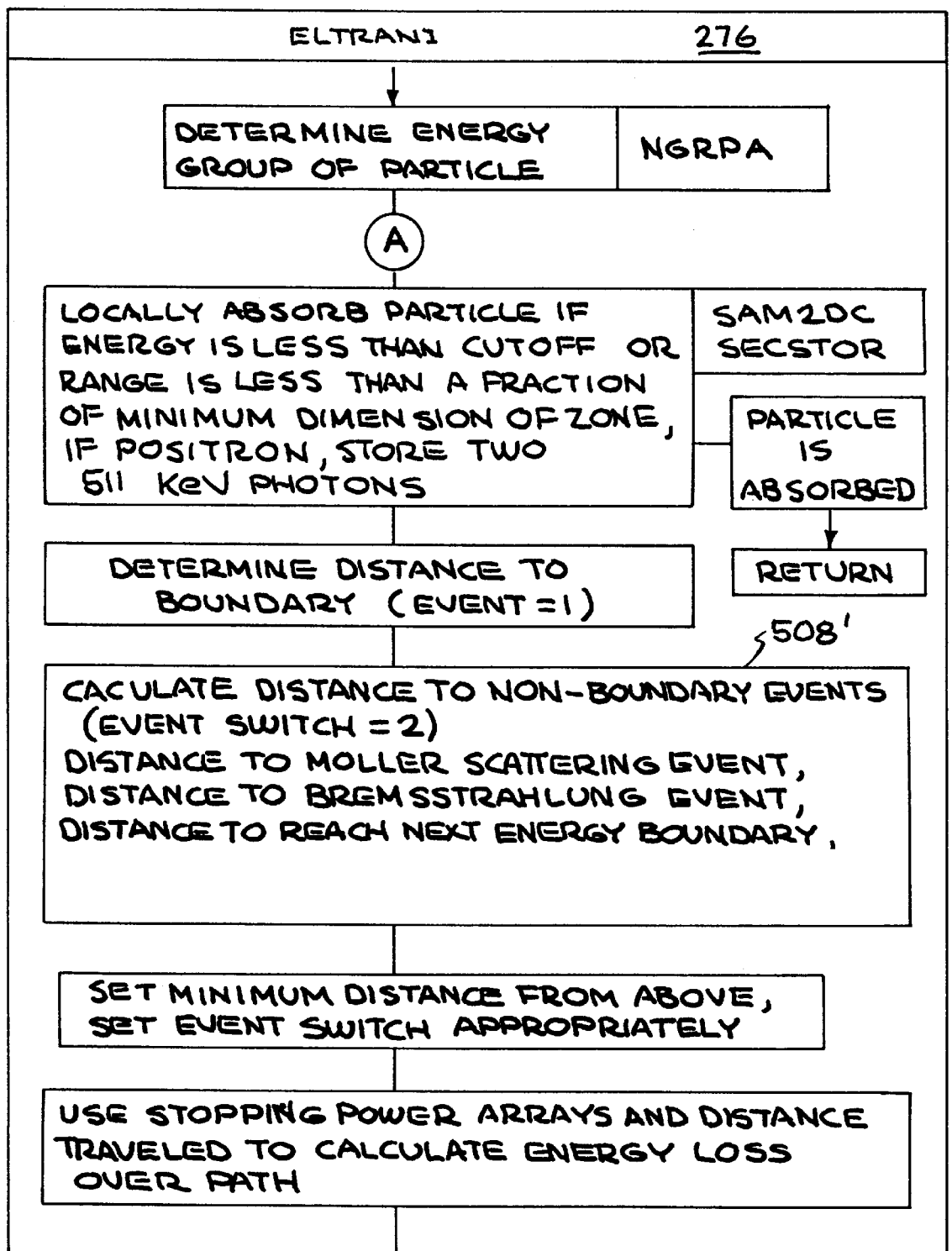
Figure 28E:
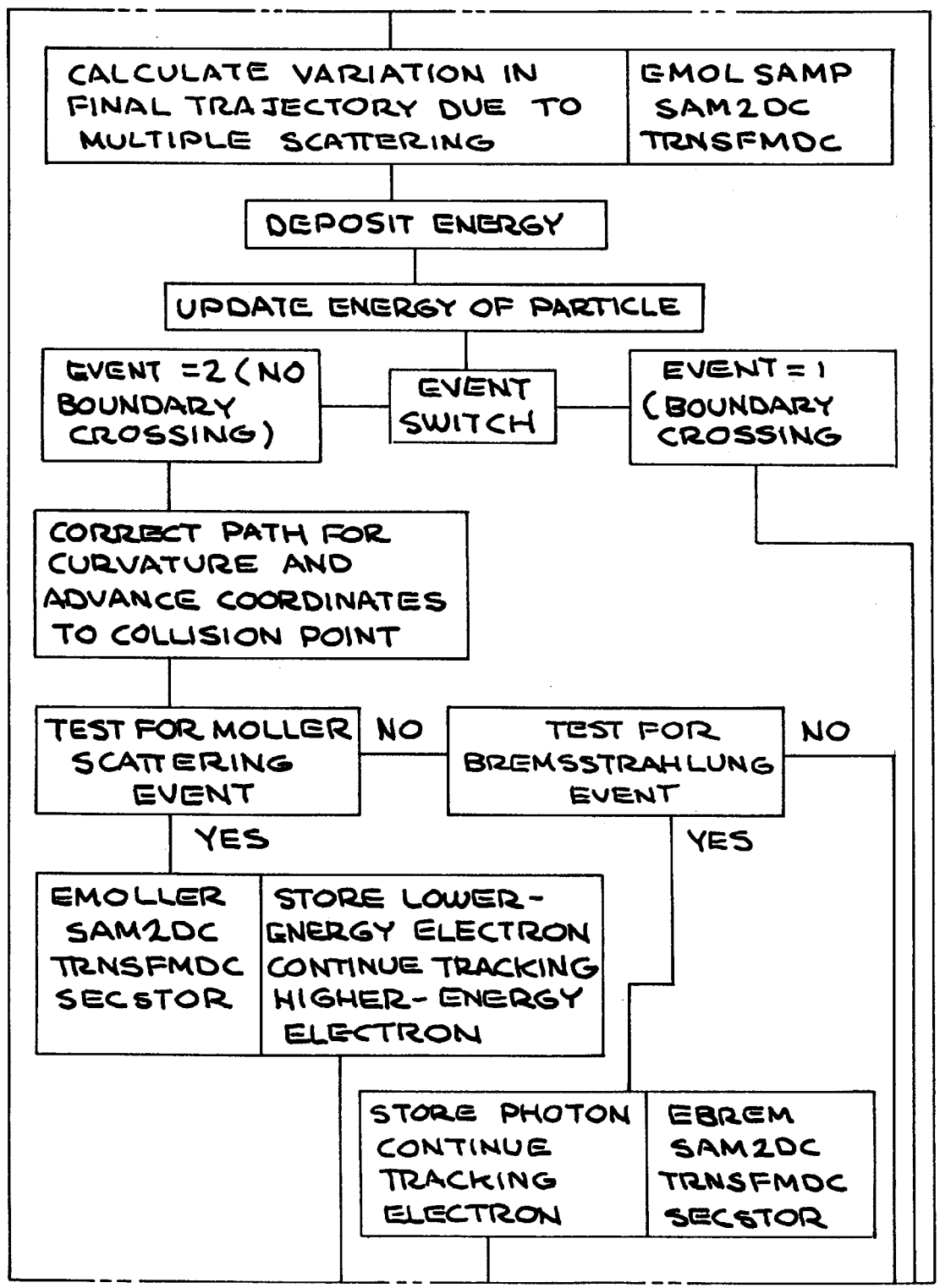
Figure 28F:
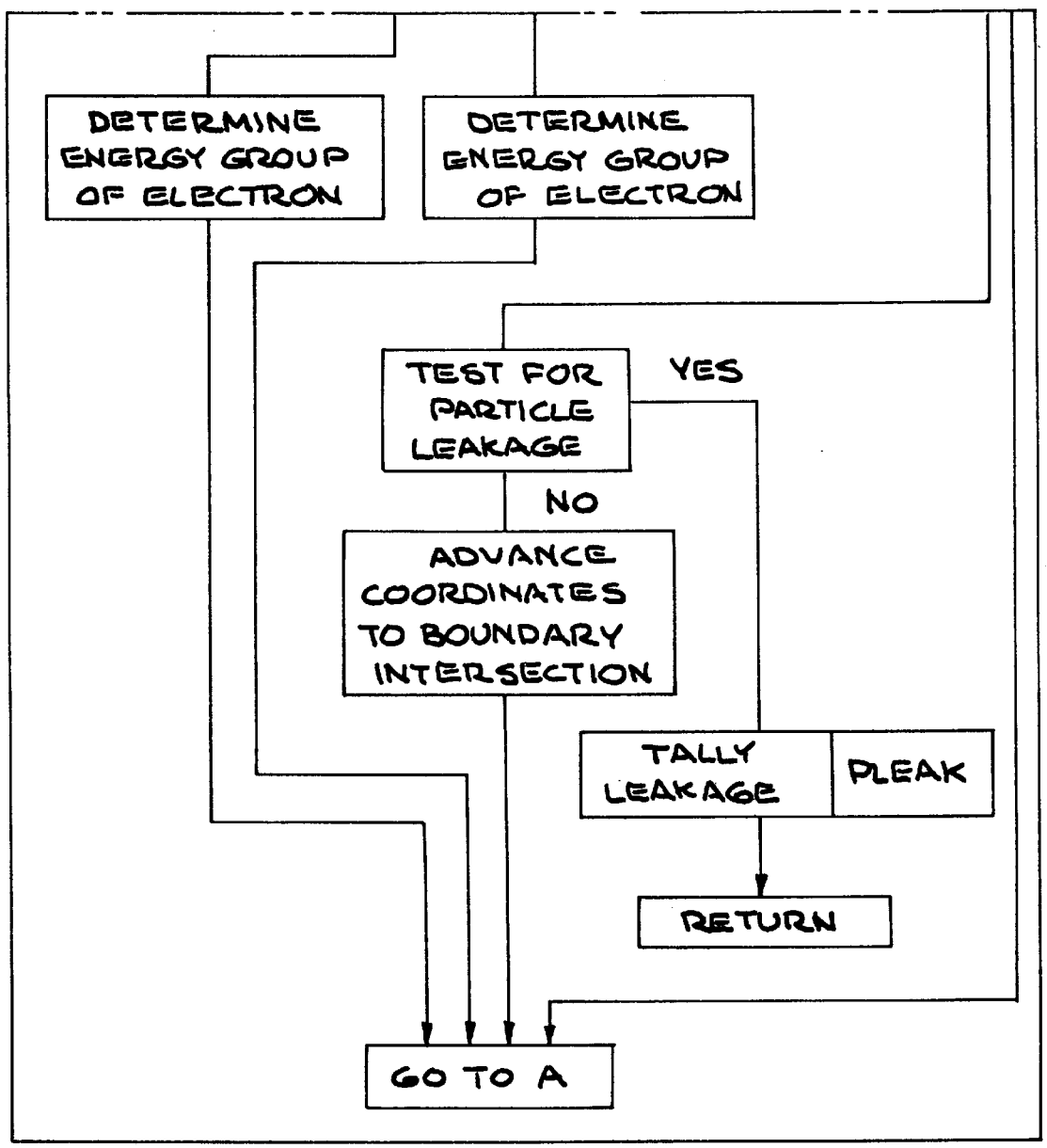

The flow ELTRANI (276), shown in FIG. 28B, is equivalent to ELTRAN (274), shown in FIG. 28A, except that step 508' does not calculate the maximum distance allowed by multiple scattering theory assumptions.

Figure 29:
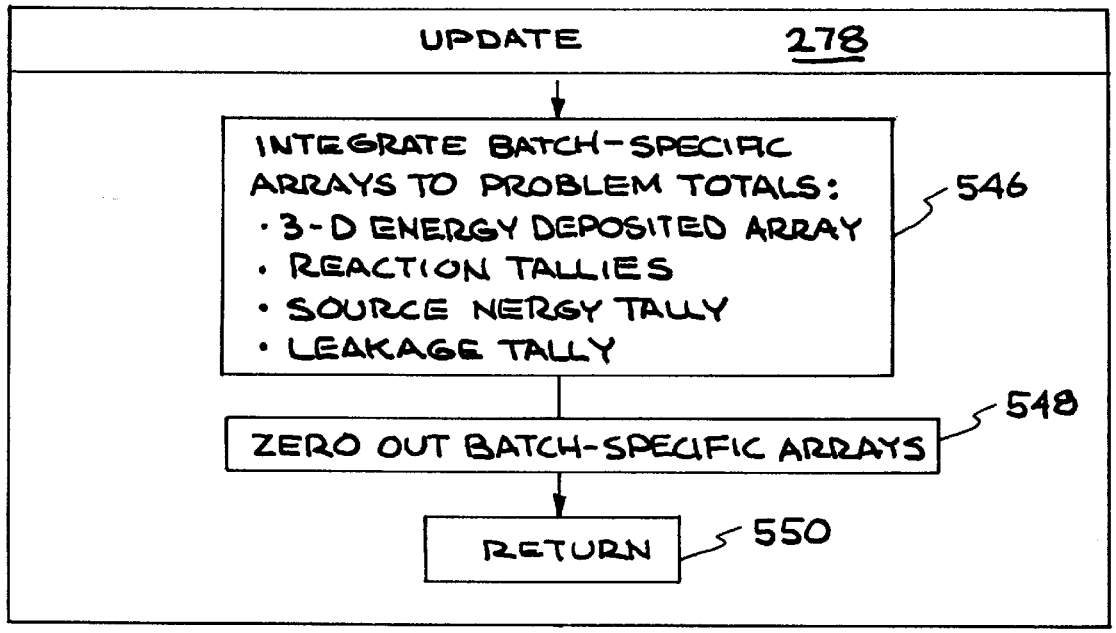

Referring to FIG. 29, UPDATE (278) integrates batch-specific arrays to problem totals including (i) a 3-D energy deposited array, (ii) reaction tallies, (iii) a source energy tally, and (iv) a leakage tally, all at step 546. Batch-specific arrays are zeroed out at step 548 and the program flow returns to the calling routine at step 550.

Figure 30:
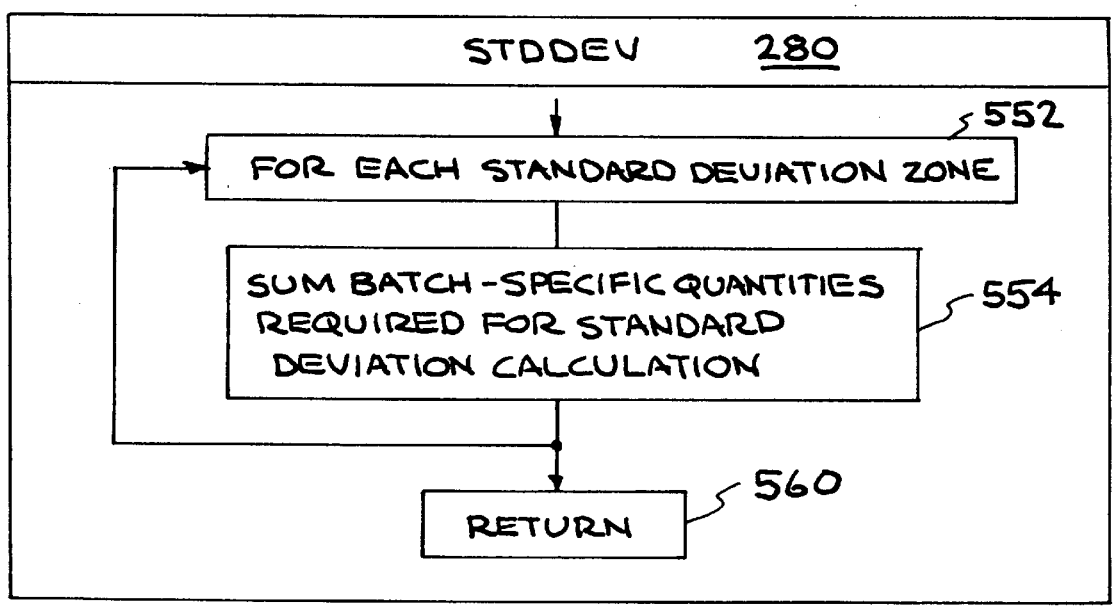
Figure 31:
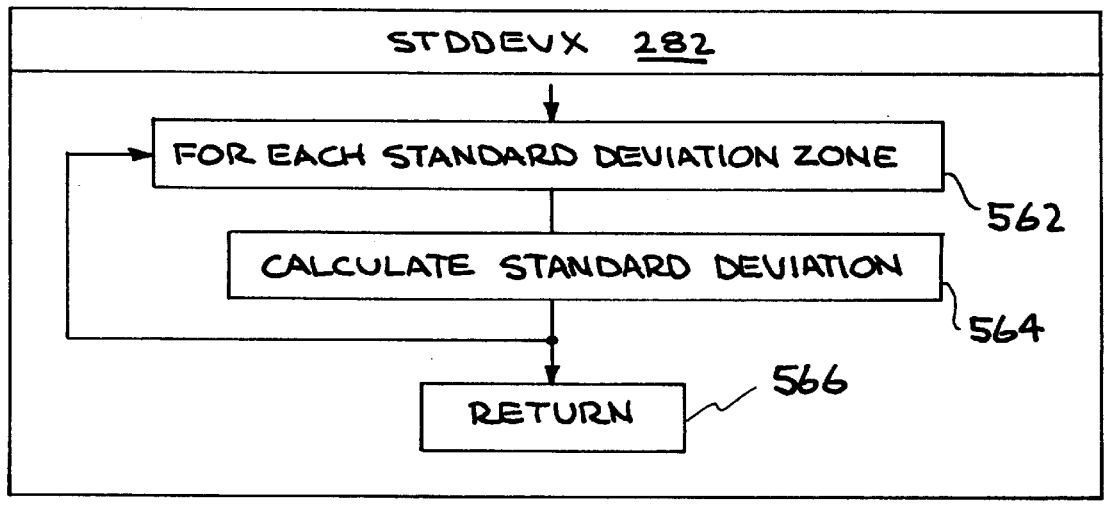

Referring to FIG. 30, STDDEV (280) sums batch-specific quantities for standard deviation calculations at 554 for each standard deviation zone at step 552 and returns to the calling routine at step 560. STDDEVX (282) calculates the standard deviation zone at step 564 for each standard deviation zone at 562 before returning to the calling routine at step 566 as shown in FIG. 31.

Figure 32:
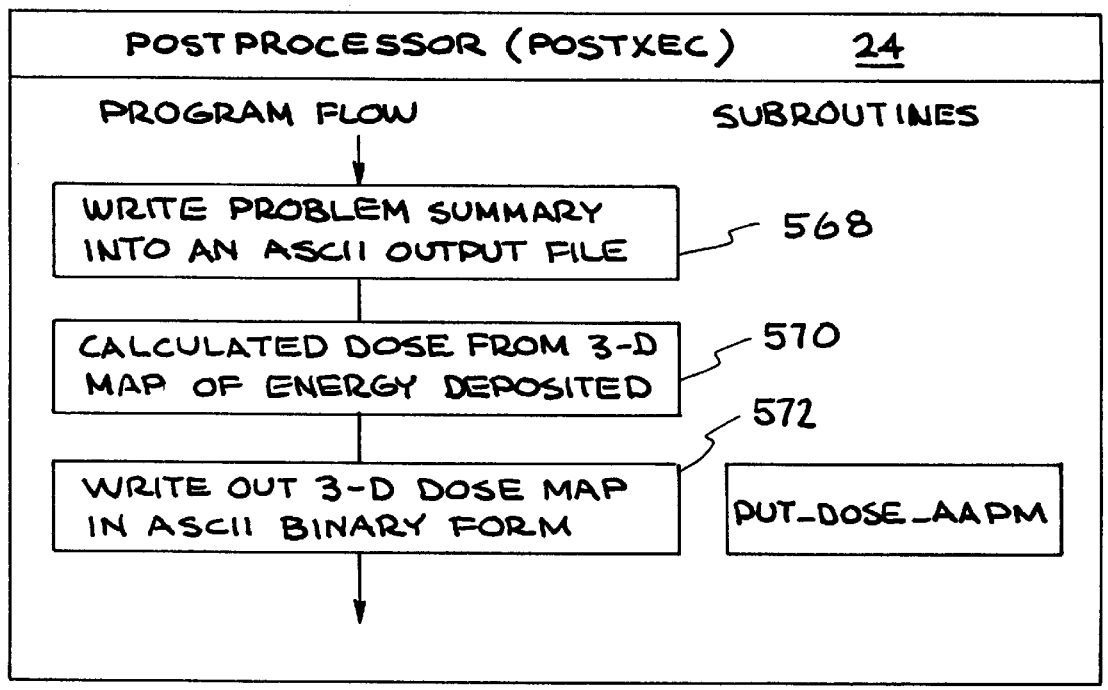
FIG. 32 shows the program flow of the postprocessor 24.

Postprocessor (POSTXEC) 24 as shown in FIG. 32 begins with step 568 by writing the problem summary into an ASCII output file. Step 570 calculates the dose from 3-D map of energy deposited and writes out a 3-D dose map in ASCII or binary form at step 572.

Figure 33:
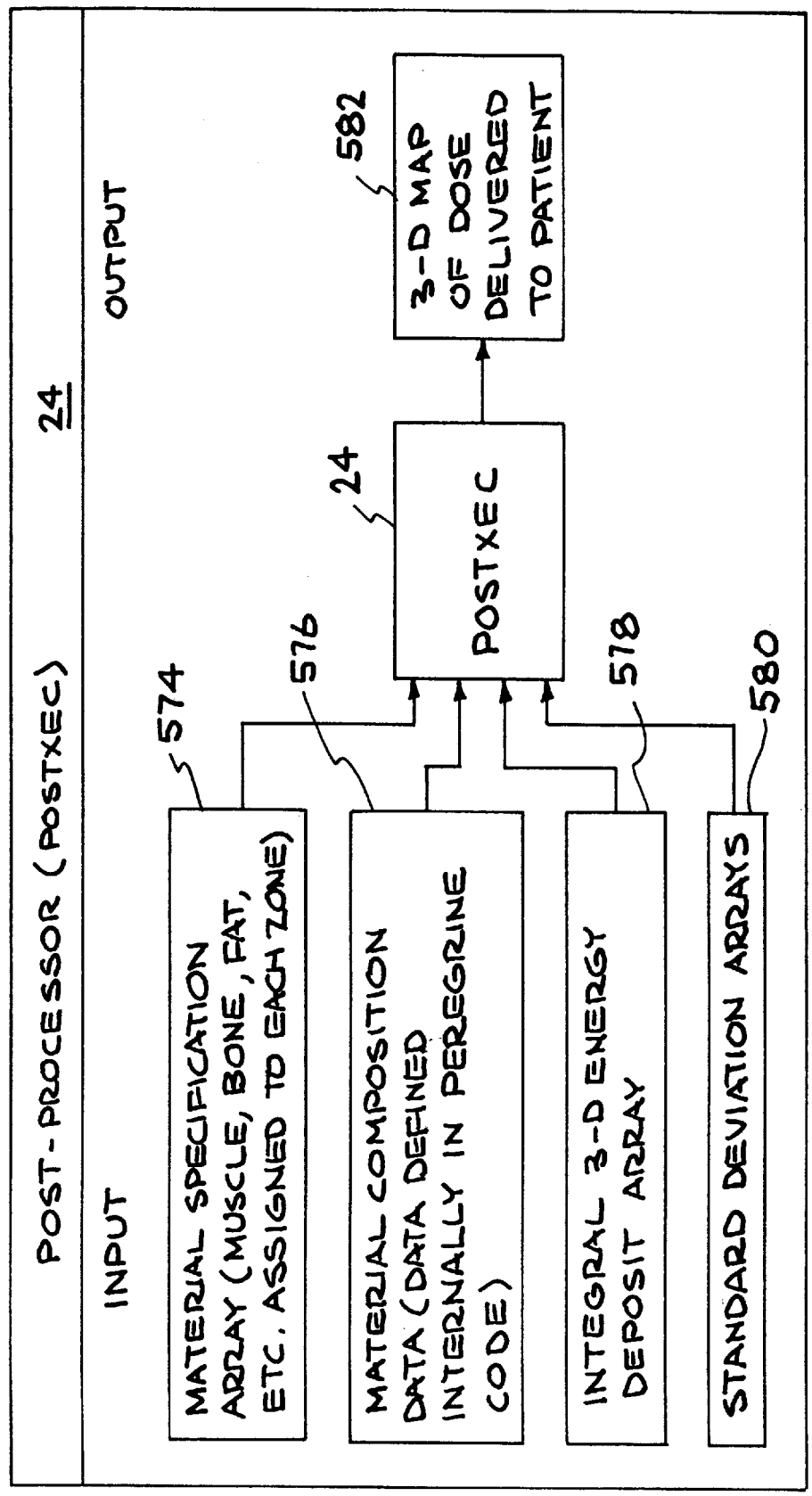
FIG. 33 shows the data flow for the postprocessor 24.

FIG. 33 is a data flow diagram of POSTXEC (24). Inputs (574, 576, 578, 580) comprising the material array, material composition data, the integral 3-D energy deposit array, and the standard deviation arrays are passed to the post-processor, POSTXEC (24). The output of POSTXEC (24) is a 3-D map of dose delivered to the patient (582).

Changes and modifications in the specifically described embodiments can be carried out without departing from the scope of the invention, which is intended to be limited by the scope of the appended claims.

We claim:

1. An apparatus, comprising:
  a computer readable memory; and
  a computer program loaded into said computer readable memory, wherein said computer program comprises means for producing a 3-dimensional map of a radiation dose delivered to a patient, said means for producing a 3-dimensional map comprising a computer implemented process for producing a 3-dimensional map of a radiation dose delivered to a patient, comprising:
    constructing patient-dependent information necessary for a Monte-Carlo transport calculation, wherein the step of constructing patient dependent-information comprises:
    determining user-specified options from an input of (i) Monte Carlo parameters, (ii) physics options and (iii) output options, to set switches for code control;
    determining the number of energy groups for transport of each particle type from nuclear/atomic/electron data to provide the number of energy groups for each particle type;
    using computed tomography (CT) information to define dimensions and material composition for each CT voxel from an input of (i) user options comprising user-specified thresholds for processing CT scans and (ii) a CT scan array to contribute to the production of a material specification array;
    reading user-drawn contours that describe patient structures and modifying said material specification arrays from an input of a second set of user options comprising user-drawn contours, to complete the production of said material specification array and to provide a standard deviation zone identification array;

reading user input specifying each radiation beam source from an input of radiation source specifications comprising external beam characteristics and modifiers to provide radiation source angular and energy distributions and arrays describing beam delivery components;

reading user input specifying each internal (brachytherapy) source from an input of an internal radiation source specification to provide radiation source angular and energy distributions;

completing the final setup for material arrays from an input of material composition data which is defined internally within the code to provide problem dependent material and isotope specification arrays;

reading nuclear and atomic data and constructing transport arrays from an input of (i) said nuclear/atomic/electron data, (ii) said number of energy groups for each particle type and (iii) said problem-dependent material and isotope specification arrays to provide (i) nuclear and atomic transport data arrays, (ii) heavy charged particle transport data arrays and (iii) energy group structure for each particle type; and reading electron data and constructing transport arrays from an input of (i) said nuclear/atomic/electron data and (ii) said problem-dependent material and isotope specification arrays to produce electron transport data arrays;

executing said Monte-Carlo transport calculation, wherein the step of executing the Monte Carlo transport calculation comprises:

selecting particle attributes for a primary particle arising from an external radiation beam from an input of (i) radiation source angular and energy distributions, (ii) arrays describing beam delivery components, (iii) material data, (iv) nuclear and atomic transport data arrays and (v) number and energy group structure for each particle type, and to contribute a first portion to the provision of attributes of one particle, wherein said attributes comprise energy, location, direction and type;

selecting particle attributes for a primary particle arising from an internal radiation source from an input of radiation source angular and energy distributions to contribute a second portion to the provision of said attributes of one particle;

selecting a particle that has been created by an interaction of another particle in a transport mesh from an input of secondary particle arrays to provide a third portion to and complete the provision of said attributes of one particle;

(i) tracking a neutron through said transport mesh, (ii) recording energy deposited by said neutron and (iii) storing attributes of secondary particles produced in a secondary particle array from an input of (i) attributes of one particle (said neutron), (ii) switches set for code control, (iii) a material specification array, (iv) material data, (v) nuclear transport data arrays, and (vi) the number and energy group structure for said neutrons, to provide secondary particle arrays for neutrons and a 3-D energy deposit map for neutrons;

(i) tracking a photon through said transport mesh, (ii) recording energy deposited by said photon and (iii) storing attributes of secondary particles produced in secondary particle arrays for photons from an input of (i) attributes of one photon particle, (ii) said switches set for code control, (iii) said material specification arrays, (iv) said material data, (v) said atomic transport data arrays, and (vi) number and energy group structure for photons, to provide secondary particle arrays for photons and a 3-D energy deposit map for photons;

(i) tracking a heavy charged particle through said transport mesh, (ii) recording the energy deposited by said heavy charged particle and (iii) storing the attributes of secondary particles produced in secondary particle arrays for heavy charged particles from an input of (i) said switch settings for code control, (ii) said material specification array, (iii) said material data, (iv) said nuclear transport data arrays, (v) heavy charged particle transport data arrays and (vi) the number and energy group structure for heavy charged particles to provide secondary particle arrays for heavy charged particles and a 3-D deposit map for heavy charged particles;

(i) tracking a primary electron through said transport mesh, (ii) recording the energy deposited by said electron and (iii) storing the attributes of secondary particles produced in secondary particle arrays for primary electrons from an input of (i) the attributes of one particle (primary electron), (ii) said switch settings for code control, (iii) said material specification array, (iv) said material data, (v) electron transport data arrays and (vi) said number and energy group structure for said electrons to provide secondary particle arrays for primary electrons and a 3-D energy deposit map for primary electrons;

(i) tracking secondary electrons through said transport mesh, (ii) recording the energy deposited by said secondary electron and (iii) storing the attributes of secondary particles produced (secondary electrons) in secondary particle arrays for secondary electrons from an input of (i) the attributes of one particle (a secondary electron), (ii) said switch settings for code control, (iii) said material specification array, (iv) said material data, (v) said electron transport data arrays and (vi) said number and energy group structure for electrons to provide said secondary particle arrays for secondary electrons and a 3-D energy deposit map for secondary electrons;

adding all 3-D energy deposit maps calculated over a batch to a 3-D energy deposit map for the problem from an input of a 3-D energy deposit map calculated for a single batch to provide an integral 3-D energy deposit map;

updating the arrays necessary for a standard deviation calculation with energy deposit information determined from each said batch from an input of said integral 3-D energy deposit map and a standard deviation zone ID array to provide standard deviation precalculation arrays; and calculating standard deviation from an input of said standard deviation precalculation arrays to provide standard deviation arrays; and producing, from said patient-dependent information and said Monte-Carlo transport calculation, a 3-dimensional map of the dose delivered to said patient.

2. The apparatus of claim 1, wherein said means for producing a 3-dimensional map of a radiation dose delivered to a patient comprise:

means for constructing patient-dependent information comprising:

a material specification array including information on tissue classification;

material data including material composition and density;

particle data including particle mass and charge; nuclear and atomic transport data arrays;

radiation source angular and energy distributions; and arrays describing beam delivery components; means for producing from said patient-dependent information;

a 3-dimensional map of the energy that has been deposited in said patient; and a 3-dimensional map of the standard deviation of the energy deposited in said patient; and means for formatting a 3-dimensional dose map from (i) said material specification array, (ii) said material data, (iii) said 3-dimensional map of the energy that has been deposited in said patient and (iv) said 3-dimensional map of the standard deviation of the energy deposited in said patient.

3. A computer implemented process for producing a 3-dimensional map of a radiation dose delivered to a patient, comprising:

constructing patient-dependent information necessary for a Monte-Carlo transport calculation, wherein the step of constructing patient dependent-information comprises:

determining user-specified options from an input of (i) Monte Carlo parameters, (ii) physics options and (iii) output options, to set switches for code control;

determining the number of energy groups for transport of each particle type from nuclear/atomic/electron data to provide the number of energy groups for each particle type;

using computed tomography (CT) information to define dimensions and material composition for each CT voxel from an input of (i) user options comprising user-specified thresholds for processing CT scans and (ii) a CT scan array to contribute to the production of a material specification array;

reading user-drawn contours that describe patient structures and modifying said material specification arrays from an input of a second set of user options comprising user-drawn contours, to complete the production of said material specification array and to provide a standard deviation zone identification array;

reading user input specifying each radiation beam source from an input of radiation source specifications comprising external beam characteristics and modifiers to provide radiation source angular and energy distributions and arrays describing beam delivery components;

reading user input specifying each internal (brachytherapy) source from an input of an internal radiation source specification to provide radiation source angular and energy distributions;

completing the final setup for material arrays from an input of material composition data which is defined internally within the code to provide problem dependent material and isotope specification arrays;

reading nuclear and atomic data and constructing transport arrays from an input of (i) said nuclear/atomic/electron data, (ii) said number of energy groups for each particle type and (iii) said problem-dependent material and isotope specification arrays to provide (i) nuclear and atomic transport data arrays, (ii) heavy charged particle transport data arrays and (iii) energy group structure for each particle type; and reading electron data and constructing transport arrays from an input of (i) said nuclear/atomic/electron data and (ii) said problem-dependent material and isotope specification arrays to produce electron transport data arrays;

executing said Monte-Carlo transport calculation, wherein the step of executing said Monte Carlo transport calculation comprises:

selecting particle attributes for a primary particle arising from an external radiation beam from an input of (i) radiation source angular and energy distributions, (ii) arrays describing beam delivery components, (iii) material data, (iv) nuclear and atomic transport data arrays and (v) number and energy group structure for each particle type, and to contribute a first portion to the provision of attributes of one particle, wherein said attributes comprise energy, location, direction and type;

selecting particle attributes for a primary particle arising from an internal radiation source from an input of radiation source angular and energy distributions to contribute a second portion to the provision of said attributes of one particle;

selecting a particle that has been created by an interaction of another particle in a transport mesh from an input of secondary particle arrays to provide a third portion to and complete the provision of said attributes of one particle;

(i) tracking a neutron through said transport mesh, (ii) recording energy deposited by said neutron and (iii) storing attributes of secondary particles produced in a secondary particle array from an input of (i) attributes of one particle (said neutron), (ii) switches set for code control, (iii) a material specification array, (iv) material data, (v) nuclear transport data arrays, and (vi) the number and energy group structure for said neutrons, to provide secondary particle arrays for neutrons and a 3-D energy deposit map for neutrons;

(i) tracking a photon through said transport mesh, (ii) recording energy deposited by said photon and (iii) storing attributes of secondary particles produced in secondary particle arrays for photons from an input of (i) attributes of one photon particle, (ii) said switches set for code control, (iii) said material specification arrays, (iv) said material data, (v) said atomic transport data arrays, and (vi) number and energy group structure for photons, to provide secondary particle arrays for photons and a 3-D energy deposit map for photons;

(i) tracking a heavy charged particle through said transport mesh, (ii) recording the energy deposited by said heavy charged particle and (iii) storing the attributes of secondary particles produced in secondary particle arrays for heavy charged particles from an input of (i) said switch settings for code control, (ii) said material specification array, (iii) said material data, (iv) said nuclear transport data arrays, (v) heavy charged particle transport data arrays and (vi) the number and energy group structure for heavy charged particles to provide secondary particle arrays for heavy charged particles and a 3-D deposit map for heavy charged particles;

(i) tracking a primary electron through said transport mesh, (ii) recording the energy deposited by said electron and (iii) storing the attributes of secondary particles produced in secondary particle arrays for primary electrons from an input of (i) the attributes of one particle (primary electron), (ii) said switch settings for code control, (iii) said material specification array, (iv) said material data, (v) electron transport data arrays and (vi) said number and energy group structure for said electrons to provide secondary particle arrays for primary electrons and a 3-D energy deposit map for primary electrons;

(i) tracking secondary electrons through said transport mesh, (ii) recording the energy deposited by said secondary electron and (iii) storing the attributes of secondary particles produced (secondary electrons) in secondary particle arrays for secondary electrons from an input of (i) the attributes of one particle (a secondary electron), (ii) said switch settings for code control, (iii) said material specification array, (iv) said material data, (v) said electron transport data arrays and (vi) said number and energy group structure for electrons to provide said secondary particle arrays for secondary electrons and a 3-D energy deposit map for secondary electrons;

adding all 3-D energy deposit maps calculated over a batch to a 3-D energy deposit map for the problem from an input of a 3-D energy deposit map calculated for a single batch to provide an integral 3-D energy deposit map;

updating the arrays necessary for a standard deviation calculation with energy deposit information determined from each said batch from an input of said integral 3-D energy deposit map and a standard deviation zone ID array to provide standard deviation precalculation arrays; and calculating standard deviation from an input of said standard deviation precalculation arrays to provide standard deviation arrays; and producing, from said patient-dependent information and said Monte-Carlo transport calculation, a 3-dimensional map of the dose delivered to said patient.

4. The method of claim 3, wherein the step of producing, from said patient dependent information and said Monte Carlo transport calculation, a 3 dimensional map of the dose delivered to said patient, comprises:

writing a problem summary into an ASCII output file;

calculating the dose from an integral 3-D map of energy deposited; and writing out a 3-D dose map from an input of said integral 3-D energy deposit array and said standard deviation 3-D arrays, wherein said 3-D dose map is written in a form selected from a group consisting of ASCII and binary.

5. A computer implemented process for producing a 3-dimensional map of a radiation dose delivered to a patient, comprising:

constructing patient-dependent information necessary for a Monte-Carlo transport calculation, wherein the step of constructing patient dependent-information comprises:

determining user-specified options from an input of (i) Monte Carlo parameters, (ii) physics options and (iii) output options, to set switches for code control;

determining the number of energy groups for transport of each particle type from nuclear/atomic/electron data to provide the number of energy groups for each particle type;

using computed tomography (CT) information to define dimensions and material composition for each CT voxel from an input of (i) user options comprising user-specified thresholds for processing CT scans and (ii) a CT scan array to contribute to the production of a material specification array;

reading user-drawn contours that describe patient structures and modifying said material specification arrays from an input of a second set of user options comprising user-drawn contours, to complete the production of said material specification array and to provide a standard deviation zone identification array;

reading user input specifying each radiation beam source from an input of radiation source specifications comprising external beam characteristics and modifiers to provide radiation source angular and energy distributions and arrays describing beam delivery components;

reading user input specifying each internal (brachytherapy) source from an input of an internal radiation source specification to provide radiation source angular and energy distributions;

completing the final setup for material arrays from an input of material composition data which is defined internally within the code to provide problem dependent material and isotope specification arrays;

reading nuclear and atomic data and constructing transport arrays from an input of (i) said nuclear/atomic/electron data, (ii) said number of energy groups for each particle type and (iii) said problem-dependent material and isotope specification arrays to provide (i) nuclear and atomic transport data arrays, (ii) heavy charged particle transport data arrays and (iii) energy group structure for each particle type; and reading electron data and constructing transport arrays from an input of (i) said nuclear/atomic/electron data and (ii) said problem-dependent material and isotope specification arrays to produce electron transport data arrays;

executing said Monte-Carlo transport calculation; and producing, from said patient-dependent information and said Monte-Carlo transport calculation, a 3-dimensional map of the dose delivered to said patient.

6. A computer implemented process for producing a 3-dimensional map of a radiation dose delivered to a patient, comprising:

constructing patient-dependent information necessary for a Monte-Carlo transport calculation;

executing said Monte-Carlo transport calculation; wherein the step of executing the Monte Carlo transport calculation comprises:

selecting particle attributes for a primary particle arising from an external radiation beam from an input of (i) radiation source angular and energy distributions, (ii) arrays describing beam delivery components, (iii) material data, (iv) nuclear and atomic transport data arrays and (v) number and energy group structure for each particle type, and to contribute a first portion to the provision of attributes of one particle, wherein said attributes comprise energy, location, direction and type;

selecting particle attributes for a primary particle arising from an internal radiation source from an input of radiation source angular and energy distributions to contribute a second portion to the provision of said attributes of one particle;

selecting a particle that has been created by an interaction of another particle in a transport mesh from an input of secondary particle arrays to provide a third portion to and complete the provision of said attributes of one particle;

(i) tracking a neutron through said transport mesh, (ii) recording energy deposited by said neutron and (iii) storing attributes of secondary particles produced in a secondary particle array from an input of (i) attributes of one particle (said neutron), (ii) switches set for code control, (iii) a material specification array, (iv) material data, (v) nuclear transport data arrays, and (vi) the number and energy group structure for said neutrons, to provide secondary particle arrays for neutrons and a 3-D energy deposit map for neutrons;

(i) tracking a photon through said transport mesh, (ii) recording energy deposited by said photon and (iii) storing attributes of secondary particles produced in secondary particle arrays for photons from an input of (i) attributes of one photon particle, (ii) said switches set for code control, (iii) said material specification arrays, (iv) said material data, (v) said atomic transport data arrays, and (vi) number and energy group structure for photons, to provide secondary particle arrays for photons and a 3-D energy deposit map for photons;

(i) tracking a heavy charged particle through said transport mesh, (ii) recording the energy deposited by said heavy charged particle and (iii) storing the attributes of secondary particles produced in secondary particle arrays for heavy charged particles from an input of (i) said switch settings for code control, (ii) said material specification array, (iii) said material data, (iv) said nuclear transport data arrays, (v) heavy charged particle transport data arrays and (vi) the number and energy group structure for heavy charged particles to provide secondary particle arrays for heavy charged particles and a 3-D deposit map for heavy charged particles;

(i) tracking a primary electron through said transport mesh, (ii) recording the energy deposited by said electron and (iii) storing the attributes of secondary particles produced in secondary particle arrays for primary electrons from an input of (i) the attributes of one particle (primary electron), (ii) said switch settings for code control, (iii) said material specification array, (iv) said material data, (v) electron transport data arrays and (vi) said number and energy group structure for said electrons to provide secondary particle arrays for primary electrons and a 3-D energy deposit map for primary electrons;

(i) tracking secondary electrons through said transport mesh, (ii) recording the energy deposited by said secondary electron and (iii) storing the attributes of secondary particles produced (secondary electrons) in secondary particle arrays for secondary electrons from an input of (i) the attributes of one particle (a secondary electron), (ii) said switch settings for code control, (iii) said material specification array, (iv) said material data, (v) said electron transport data arrays and (vi) said number and energy group structure for electrons to provide said secondary particle arrays for secondary electrons and a 3-D energy deposit map for secondary electrons;

adding all 3-D energy deposit maps calculated over a batch to a 3-D energy deposit map for the problem from an input of a 3-D energy deposit map calculated for a single batch to provide an integral 3-D energy deposit map;

updating the arrays necessary for a standard deviation calculation with energy deposit information determined from each said batch from an input of said integral 3-D energy deposit map and a standard deviation zone ID array to provide standard deviation precalculation arrays; and calculating standard deviation from an input of said standard deviation precalculation arrays to provide standard deviation arrays; and producing, from said patient-dependent information and said Monte-Carlo transport calculation, a 3-dimensional map of the dose delivered to said patient.

* * * * *